United States Patent
Butt et al.

(10) Patent No.: US 11,479,597 B2
(45) Date of Patent: Oct. 25, 2022

(54) THIOSUCCINYL-CROSSLINKED HEMOGLOBIN ANALOGS AND METHODS OF USE AND PREPARATION THEREOF

(71) Applicant: Billion King International Limited, Hong Kong (CN)

(72) Inventors: Kwok Chu Butt, Hong Kong (CN); Norman Fung-Man Wai, Vancouver (CA); Hiu Chi Chong, Hong Kong (CN); Wing Fung Wu, Hong Kong (CN); Colin Pak Fai Yeh, Hong Kong (CN); Benjamin Chi Yin Wai, Vancouver (CA)

(73) Assignee: Billion King International Limited, Hong Kong (CN)

( * ) Notice: Subject to any disclaimer, the term of this patent is extended or adjusted under 35 U.S.C. 154(b) by 0 days.

(21) Appl. No.: 16/947,993

(22) Filed: Aug. 27, 2020

(65) Prior Publication Data

US 2021/0061885 A1    Mar. 4, 2021

Related U.S. Application Data

(60) Provisional application No. 62/893,220, filed on Aug. 29, 2019.

(51) Int. Cl.
| | | |
|---|---|---|
| *C07K 14/805* | (2006.01) | |
| *C07K 1/107* | (2006.01) | |
| *A61P 1/16* | (2006.01) | |
| *A61P 7/08* | (2006.01) | |
| *A61P 13/12* | (2006.01) | |
| *A61P 25/00* | (2006.01) | |
| *A61P 35/00* | (2006.01) | |
| *A61P 9/10* | (2006.01) | |
| *A61K 38/00* | (2006.01) | |

(52) U.S. Cl.
CPC ............ *C07K 14/805* (2013.01); *A61P 1/16* (2018.01); *A61P 7/08* (2018.01); *A61P 9/10* (2018.01); *A61P 13/12* (2018.01); *A61P 25/00* (2018.01); *A61P 35/00* (2018.01); *C07K 1/1077* (2013.01); *A61K 38/00* (2013.01)

(58) Field of Classification Search
CPC ....... C07K 14/805; C07K 1/1077; A61P 1/16; A61P 7/08; A61P 9/10; A61P 13/12; A61P 25/00; A61P 35/00; A61K 38/00
See application file for complete search history.

(56) References Cited

U.S. PATENT DOCUMENTS

| | | | |
|---|---|---|---|
| 3,931,270 A * | 1/1976 | Evers | C07C 49/203 |
| | | | 558/253 |
| 5,281,579 A | 1/1994 | Estep | |
| 5,741,894 A | 4/1998 | Azari et al. | |
| 7,494,974 B2 | 2/2009 | Tye | |
| 7,504,377 B2 | 3/2009 | Tye | |
| 7,989,593 B1 | 8/2011 | Wong et al. | |
| 8,106,011 B1 * | 1/2012 | Wong | A61P 9/00 |
| | | | 514/13.5 |
| 8,129,338 B2 | 3/2012 | Tye | |

OTHER PUBLICATIONS

Zhitkovich (Chemical Research in Toxicology, 2019, 32, 1318-1319) (Year: 219).*
Habler O, Kleen M, Pape A, Meisner F, Kemming G, Messmer K. Diaspirin-crosslinked hemoglobin reduces mortality of severe hemorrhagic shock in pigs with critical coronary stenosis. Critical Care Medicine, 28(6): 1889-1898, (2000).
Figueiredo, L.F, Mathru M, Jones J.R, Solanki D & Kramer G.C. Inhaled nitric oxide reverses cell-free hemoglobin-induced pulmonary hypertension and decreased lung compliance. Critical Care, 1(3): 111-116 (1997).

* cited by examiner

*Primary Examiner* — Sudhakar Katakam
(74) *Attorney, Agent, or Firm* — Spruson & Ferguson (Hong Kong) Limited

(57) ABSTRACT

Provided herein are thiosuccinyl-crosslinked hemoglobin analogs useful as blood replacement agents, pharmaceutical compositions comprising the same and the methods of use and preparation thereof.

21 Claims, 36 Drawing Sheets

Specification includes a Sequence Listing.

HLDDLKGTFAALSELHCDK
I-CYS
MLTAEEK

| Peptide sequence | Peptide mass (g/mol) | b++ sequence number | Linker DBSF-CYS | Link position 81-1 | Score 8.652523E-10 |
|---|---|---|---|---|---|
| | | | | | b++ m/z on spectrum (with DBSF-CYS g/mol) |
| HLDDLK-MLTAEEK | 1542.76 | b6 | | | 872.40 |
| HLDDLKG-MLTAEEK | 1599.81 | b7 | | | 900.91 |
| HLDDLKGT-MLTAEEK | 1700.91 | b8 | | | 951.43 |
| HLDDLKGTF-MLTAEEK | 1848.08 | b9 | | | 1024.97 |
| HLDDLKGTFA-MLTAEEK | 1919.16 | b10 | | | 1060.49 |
| HLDDLKGTFAA-MLTAEEK | 1990.24 | b11 | | | 1096.01 |
| HLDDLKGTFAAL-MLTAEEK | 2103.40 | b12 | | | 1152.55 |

SEQUENCE LISTING

```
<160> NUMBER OF SEQ ID NOS: 9

<210> SEQ ID NO 1
<211> LENGTH: 19
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 1

His Leu Asp Asp Leu Xaa Gly Thr Phe Ala Ala Leu Ser Glu Leu His
1               5                   10                  15

Cys Asp Lys

<210> SEQ ID NO 2
<211> LENGTH: 6
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 2

His Leu Asp Asp Leu Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 3
```

His Leu Asp Asp Leu Xaa Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 4

His Leu Asp Asp Leu Xaa Gly Thr
1               5

<210> SEQ ID NO 5
<211> LENGTH: 9
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 5

His Leu Asp Asp Leu Xaa Gly Thr Phe
1               5

<210> SEQ ID NO 6
<211> LENGTH: 10
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 6

His Leu Asp Asp Leu Xaa Gly Thr Phe Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 7

```
His Leu Asp Asp Leu Xaa Gly Thr Phe Ala Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (6)..(6)
<223> OTHER INFORMATION: Xaa at position 6 is a lysine residue, wherein
      the side chain amino group of the lysine residue is crosslinked
      with a cysteinyl-succinyl moiety to the N-terminal amine of SEQ ID
      NO:9

<400> SEQUENCE: 8

His Leu Asp Asp Leu Xaa Gly Thr Phe Ala Ala Leu
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Artificial polypeptide synthesized in the lab
<220> FEATURE:
<221> NAME/KEY: MISC_FEATURE
<222> LOCATION: (1)..(1)
<223> OTHER INFORMATION: The N-terminal amine is crosslinked with a
      cysteinyl-succinyl moiety with the side chain amino group of the
      lysine residue at position 6 of SEQ ID NO:1-8.

<400> SEQUENCE: 9

Met Leu Thr Ala Glu Glu Lys
1               5
```

THIOSUCCINYL-CROSSLINKED HEMOGLOBIN ANALOGS AND METHODS OF USE AND PREPARATION THEREOF

CROSS REFERENCE TO RELATED APPLICATIONS

This application claims the benefit of priority of International Application No. PCT/CN2020/111595, filed on Aug. 27, 2020, which claims the benefit of priority of U.S. Provisional Application No. 62/893,220 filed on Aug. 29, 2019, which are hereby incorporated by reference in their entirety.

INCORPORATION BY REFERENCE OF SEQUENCE LISTING

The specification further incorporates by reference the Sequence Listing submitted herewith via EFS-Web on Jul. 12, 2021. The Sequence Listing text file, identified as Seq_Listing_034647-000003.txt, is 5 kilobytes and was created on Jul. 12, 2021.

TECHNICAL FIELD

The present disclosure generally relates to thiosuccinyl-crosslinked hemoglobin analogs, pharmaceutical compositions comprising the same and the methods of use and preparation thereof.

BACKGROUND

Hemoglobin is an iron-containing, oxygen-transport metalloprotein present in red blood cells of almost all vertebrates as well as the tissues of some invertebrates. Hemoglobin in red blood cells is responsible for carrying oxygen from the lungs to the rest of the body and then returning carbon dioxide from the body cells to the lungs, where the carbon dioxide can be exhaled. Since hemoglobin has this oxygen transport feature, purified hemoglobin from human- or animal-derived red blood cells is an ideal material for use in the development of potent oxygen therapeutics, if it can be stabilized ex vivo and used in vivo and ex vivo.

Naturally-occurring hemoglobin is a non-covalently linked heterotetramer composed of $2\alpha$ and $2\beta$ globin subunits, and it is generally stable when present within red blood cells. However, when naturally-occurring hemoglobin is removed from red blood cells, it becomes unstable and splits into 2 dimers ($\alpha\beta$ globin chains) in blood circulation. The dimeric hemoglobin is rapidly cleared from the kidney via glomerular filtration, because of its lower molecular weight (approximately 32 kDa) (Bunn, H. F. et al., 1969, J Exp Med, 129: 909-23) or from the liver via the haptoglobin-CD 163 pathway (Kristiansen, M. et al., 2001, Nature, 409: 198-201). The breakdown of the tetramer linkage not only causes renal injury when the dissociated hemoglobin is filtered through the kidneys and excreted, but also negatively impacts the sustainability of the functional hemoglobin in blood circulation.

To overcome these problems, researchers have attempted to develop various types of modified hemoglobin (hemoglobin-based oxygen carrier, HBOC) with either a stable tetramer configuration or an increased molecular weight. These HBOCs are developed from hemoglobin purified from human- or animal-derived red blood cells and further modified by intra- or intermolecular cross-linking, polymerization, PEGylation or encapsulation (Keipert, P. E. et al., 1992, Biomater Artif Cells Immobil Biotechnol, 20: 737-45). Compared to stroma-free hemoglobin, these HBOCs can have longer blood retention and possess different oxygen transport capacities based on the hemoglobin modification strategies used.

Although the safety, efficacy and pharmacokinetics of these HBOCs were evaluated in preclinical and clinical trials (Jahr, J. S. et al., 2012, Curr Drug Discov Technol, 9: 158-65; Kim, H. W. & Greenburg, A. G, 2004, Artif Organs, 28: 813-28), the United States Food and Drug Administration (FDA) has not approved any HBOCs for use in humans yet. Human hemoglobin products were developed since 1993 and evaluated in Phase III trials, but their development for clinical use was suspended, because of the undesirable side effects reported in clinical trial studies (Hess, J. et al., 1991, Blood 78:356A; Jahr, J. S. et al., 2012, Curr Drug Discov Technol, 9: 158-65; Winslow, R. M., 2000, Vox Sang, 79:1-20; Cheng, D. C. et al., 2004, J Thorac Cardiovasc Surg, 127: 79-86; Greenburg, A. G. et al., 2004, J Am Coll Surg, 198: 373-383; Hill, S. E. et al., 2002, J Cardiothorac Vasc Anesth, 16: 695-702).

Although the failure of using acellular human HBOC products is reported to be associated with a significantly increased risk of death and myocardial infract compared to a control solution, a bovine hemoglobin glutamer-250, HBOC-201, from Hemopure, is approved for the treatment of anemia and for use during surgery in South Africa since 2001 (Lok, C., 2001, Nature, 410:855; Mer, M. et al., 2016, Transfusion (Paris), 56:2631-36) and it is also provided to patients with life-threatening anemia in the United States for whom allogeneic blood transfusion is not an option since 2014 (Lundy, J. B. et al., 2014, Int J Burns Trauma, 4: 45-8; Posluszny, J. A. & Napolitano, L. M., 2016, Archives of Trauma Research, 5: e30610; Resar, L. M. et al., 2016, Transfusion, 56: 2637-47).

Even though renal toxicity issues are addressed by preventing hemoglobin dissociation, vasoconstriction following the administration is another safety concern of HBOC products. It has been shown that acellular hemoglobin is much more effective in scavenging nitric oxide (NO) with respect to hemoglobin inside red blood cells, which results in vasoconstriction and hypertension observed with HBOC administration (Mozzarelli, A. et. al., 2010, Blood Transfus, 8(S3): s59-s68). The mean arterial blood pressure increased immediately after HBOC infusion and such increase is often associated with reduced cardiac output and increased total peripheral resistance (Hess, J. R. het al., 1993, J Appl Physiol, 74(4):1769-78). Vasoconstriction can limit tissue perfusion and oxygenation and is a severe adverse effect for patients that are suffering from blood loss and hemodilution.

Although NO scavenging by HBOCs is considered the primary mechanism leading to vasoconstriction, other possible factors are considered, such as oxygen pressure in the pre-capillary arterioles (Winslow, R. M., 2003, J Intern Med, 253(5): 508-17; Tsai, A. G. et al., 2003, Am J Physiol Heart Circ Physiol, 284(4): H1411-9) and solution viscosity (Gaucher-Di, S. C. et al., 2009, Biomaterials, 30(4): 445-51). In addition to NO scavenging, other mechanisms of HBOC toxicity have also been suggested, including oversupply of oxygen (Winslow, R. M., 2008, Biochim Biophys Acta, 2008, 1784: 1382-86) and heme-mediated oxidative side reactions (Alayash, A. I., 1999, Nat Biotechnol, 17: 545-9; Alayash, A. I., 2004, Nat Rev Drug Discov, 3: 152-9).

Although some new HBOCs with less reactivity to NO and reduced ability of oversupplying oxygen to guard against oxidative side reactions have been designed, some unexplained toxicities associated with these newly designed HBOCs were still observed in preclinical studies. These results revealed that the diverse chemistry of HBOC modifications and its impact on HBOC toxicity are not fully understood and the side effect profiles of HBOCs vary depending on the nature of their chemical and/or genetic modifications.

Recent developments in hemoglobin-based oxygen therapeutics have incorporated various chemical approaches, such as polymerization, PEGylation, cross-linking and encapsulation, to form stabilized multimeric hemoglobin with improved side effect profiles, so that the stabilized hemoglobin can function outside the red blood cell. The prior art teaches that highly purified stroma-free hemoglobin can be obtained by lysing animal red blood cells, followed by different purification strategies with heat treatment (Sakai, H. et al, 1994, Artif Cells Blood Substit Immobil Biotechnol, 22(3):651-6), aqueous phase extraction (Lee, C. J. & Kan, P., 1993, U.S. Pat. No. 5,407,579), tangential flow filtration (Palmer, A. F. et al, 2009, Biotechnol Prog, 25(6): 1803-9; Elmer, J. et al, 2009, Biotechnol Prog, 25(5): 1402-10) and/or anion exchange chromatography (Sun, G. & Palmer, A. F., 2008, J Chromatogr B Analyt Technol Biomed Life Sci, 867(1):1-7; Houtchens, R. A. & Rausch, C. W., 2000, U.S. Pat. No. 6,150,507; Pliura, D. H. et al, 1996, U.S. Pat. No. 5,545,328). Highly purified, stroma-free hemoglobin can be used to generate the hemoglobin-based product with designated oxygen affinity properties through different chemical approaches. Among these approaches, chemical crosslinking is one common approach to form stabilized multimeric hemoglobin through intramolecular bonds within the tetramers as well as intermolecular bonds between the stabilized tetramers. Such chemically stabilized hemoglobin can be further modified to form a HBOC with designated properties.

Bis-3,5-dibromosalicyl fumarate (DBSF), a chemical crosslinker used in hemoglobin processing, not only stabilizes hemoglobin through intramolecular crosslinking, but also affects the oxygen affinity of the hemoglobin (Beanna, J. N. et al. U.S. Pat. No. 5,248,766; Wong B. L. et al. U.S. Pat. No. 8,106,011 B1). The stabilized multimeric hemoglobin is the preferred form in order to reduce side effects of stroma-free hemoglobin and increase the circulatory half-life of the hemoglobin. However, the present inventors determined that the fumaryl moieties on the crosslinked hemoglobin react with thiols in vitro and in vivo. Conventional hemoglobin products are commonly formulated with the thiol-containing excipients, such as N-acetyl cysteine (NAC) or cysteine (Cys), aiming to reduce the level of dysfunctional methemoglobin in the pharmaceutical composition (Beanna, J. N. et al. U.S. Pat. No. 5,248,766; Timothy, E. E. U.S. Pat. No. 5,281,579; Wong B. L. et al. U.S. Pat. No. 8,106,011 B1). However, the reaction of thiol-containing excipients with the fumaryl moieties of the crosslinked hemoglobin reduces their capability of reducing methemoglobin, which may affect HBOC product stability during product storage.

In humans, the redox status in plasma is tightly regulated by low molecular weight thiols, such as glutathione, cysteine (Cys) and homocysteine. An imbalance in plasma redox status is found to be associated with cardiovascular disease (Brunelli, E et al. Oxid Med Cell Longev, 1-11, 2017). Therefore, the stabilized multimeric hemoglobin with crosslinkers containing fumaryl group taught by the prior art can cause in-vitro instability of the pharmaceutical composition and in vivo redox system imbalance, is a problem. There is thus a need in the art for a technique to create stabilized multimeric hemoglobin not only with an improved product safety profile and desirable oxygen-carrying properties, but also containing crosslinkers that do not react with thiols in-vitro and in-vivo. Such stabilized and crosslinked hemoglobin can be used in a wide variety of medical applications, depending upon different medical applications; where different levels of oxygen affinity are desirable.

SUMMARY

The present disclosure generally relates to thiosuccinyl-crosslinked hemoglobin, pharmaceutical compositions comprising the same, and methods of use and preparation thereof. At least one of the thiosuccinyl crosslinkers described herein are useful for hemoglobin stabilization. A schematic diagram of the formation of thiosuccinyl-crosslinked hemoglobin is depicted in FIG. 1. The thiosuccinyl-crosslinked hemoglobin can be produced by intermolecular 1,4-addition of thiol to hemoglobin β-β crosslinked with at least one fumaryl crosslinkers.

Provided herein is a thiosuccinyl-crosslinked hemoglobin that overcomes the stability issues associated with previously known stabilized hemoglobin with crosslinkers containing a fumaryl group, by avoiding the reaction between the stabilized hemoglobin and thiols in-vitro and in-vivo. Surprisingly, conjugation of thiols to the fumaryl moieties of the crosslinked hemoglobin also improves the in-vivo tissue oxygenation, but advantageously does not alter its p50 value.

In a first aspect, provided herein is a thiosuccinyl-crosslinked hemoglobin comprising a tetrameric hemoglobin and at least one thiosuccinyl crosslinking moiety of Formula 1:

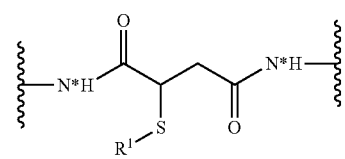

1 or a pharmaceutically acceptable salt or zwitterion thereof, wherein each N* independently represents a nitrogen selected from the group consisting of a nitrogen in a lysine residue side chain in the tetrameric hemoglobin and a nitrogen at a N-terminus in the tetrameric hemoglobin; and $R^1$ is alkyl, alkenyl, cycloalkyl, heterocycloalkyl, aryl, aralkyl, heteroaryl, or $-(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, $-(NR^4)S(O)_2OR^4$, and $-(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N$ $(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)_2N(R^4)_2$, —$(NR^4)S(O)_2N(R^4)_2$, or —$(NR^4)S(O)_2OR^4$; $R^3$ is hydrogen, alkyl, aralkyl, cycloalkyl, heterocycloalkyl, aryl, heteroaryl, $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —$(NR^4)(C=O)R^4$, —$(NR^4)(C=O)OR^4$, —$O(C=O)N(R^4)_2$, —$O(C=NR^4)N(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)_2N(R^4)_2$, —$(NR^4)S(O)_2N(R^4)_2$, or —$(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

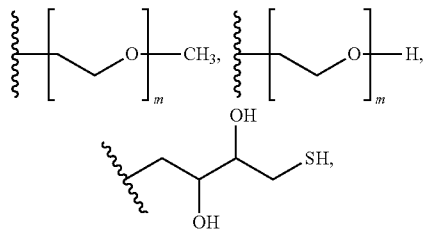

and $N^5$-(1-((carboxymethyl)amino)-1-oxo-3λ³-propan-2-yl) glutamine or a pharmaceutically acceptable salt thereof, wherein m is a whole number selected from 1-1000.

In certain embodiments, $R^1$ is a moiety of Formula 2:

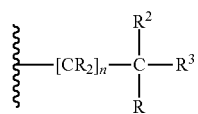

wherein n is a whole number selected from the group consisting of 0, 1, 2, 3, and 4;

R for each instance is independently selected from the group consisting of hydrogen, alkyl, aralkyl, cycloalkyl, heterocycloalkyl, aryl, and heteroaryl;

$R^2$ is hydrogen, alkyl, aralkyl, cycloalkyl, heterocycloalkyl, aryl, heteroaryl, —$N(R^4)_2$, —$NH(C=O)R^4$, or —$NH(C=O)N(R^4)_2$;

$R^3$ is hydrogen, alkyl, aralkyl, cycloalkyl, heterocycloalkyl, aryl, heteroaryl, —$CO_2R^4$, —$(C=O)NHR^4$, —$OR^4$, or —$N(R^4)_2$; and $R^4$ for each instance is independently selected from the group consisting of hydrogen, alkyl, aralkyl, cycloalkyl, heterocycloalkyl, aryl, and heteroaryl;

or $R^1$ is a moiety selected from the group consisting of:

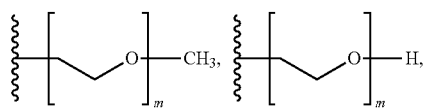

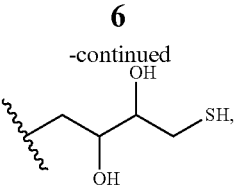

and $N^5$-(1-((carboxymethyl)amino)-1-oxo-3λ³-propan-2-yl) glutamine or a pharmaceutically acceptable salt thereof, wherein m is a whole number selected from 1-1000.

In certain embodiments, n is 1 or 2; R is hydrogen; $R^2$ is —$NHR^4$, —$NH(C=O)R^4$, or —$NH(C=O)R^4N(R^4)_2$; and $R^3$ is hydrogen, —$OR^4$, —$CO_2R^4$, or —$(C=O)NHR^4$, wherein $R^4$ for each instance is independently selected from the group consisting of hydrogen and alkyl.

In certain embodiments, $R^1$ is selected from the group consisting of:

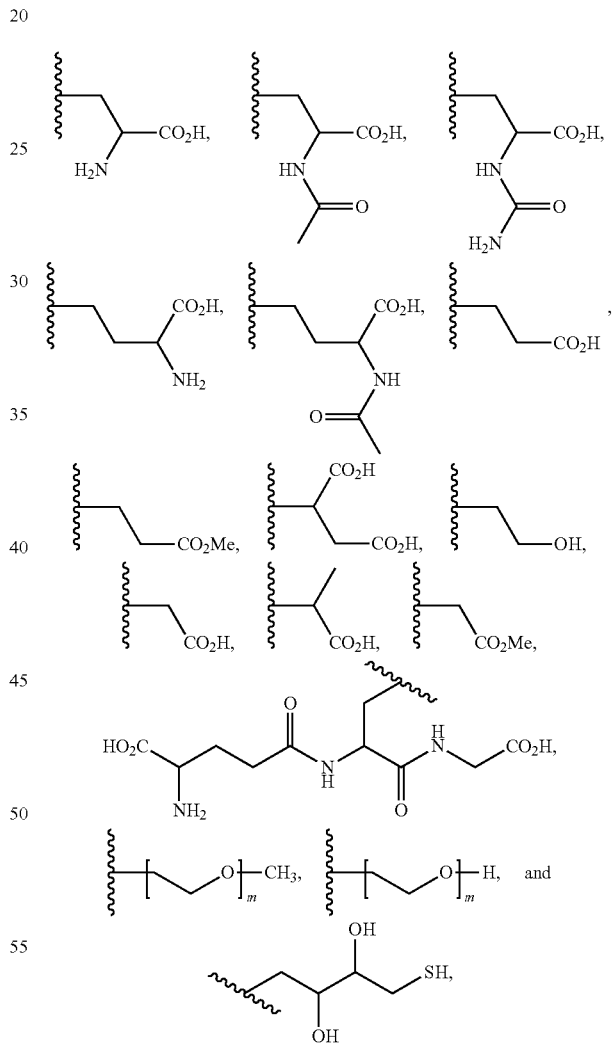

or a pharmaceutically acceptable salt or zwitterion thereof, wherein m is a whole number selected from 1-1000.

In certain embodiments, each N* independently represents a nitrogen selected from the group consisting of a nitrogen in a lysine residue side chain in a beta globin chain of the tetrameric hemoglobin and a nitrogen at a N-terminus in a beta globin chain of the tetrameric hemoglobin.

In certain embodiments, the thiosuccinyl-crosslinked hemoglobin is substantially pure.

In certain embodiments, the thiosuccinyl-crosslinked hemoglobin comprises 1, 2, or 3 thiosuccinyl crosslinking moiety of Formula 1.

In certain embodiments, the at least one thiosuccinyl crosslinking moiety crosslinks two beta globin chains of the tetrameric hemoglobin.

In certain embodiments, the tetrameric hemoglobin is human hemoglobin, bovine hemoglobin, or porcine hemoglobin.

In certain embodiments, the thiosuccinyl-crosslinked hemoglobin is substantially stroma-free.

In a second aspect, provided herein is a pharmaceutical composition comprising at least one of the thiosuccinyl-crosslinked hemoglobin as described herein and at least one pharmaceutically acceptable excipient.

In certain embodiments, the thiosuccinyl-crosslinked hemoglobin is present in the pharmaceutical composition at a weight percentage between 10-90%.

In certain embodiments, the pharmaceutical composition comprises thiosuccinyl-crosslinked hemoglobin comprising 1, 2, or 3 thiosuccinyl crosslinking moieties of Formula 1; or a combination thereof.

In a third aspect, provided herein is a method for preparing the thiosuccinyl-crosslinked hemoglobin as described herein comprising the steps of:

contacting a tetrameric hemoglobin with a fumaryl crosslinking agent thereby forming a fumaryl-crosslinked hemoglobin; contacting the fumaryl-crosslinked hemoglobin with a thiol or a pharmaceutically acceptable salt or zwitterion thereof thereby forming the thiosuccinyl-crosslinked hemoglobin as described herein.

In certain embodiments, the fumaryl crosslinking agent is selected from the group consisting of bis-3,5-dibromosalicyl fumarate (DBSF), fumaryl chloride and bis(salicyl) fumarate.

In certain embodiments, the thiol has the formula: $R^1SH$ or a pharmaceutically acceptable salt or zwitterion thereof, wherein $R^1$ is alkyl, alkenyl, cycloalkyl, heterocycloalkyl, aryl, aralkyl, heteroaryl, or $-(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $R^1$ is alkyl, alkenyl, cycloalkyl, heterocycloalkyl, aryl, aralkyl, heteroaryl, or $-(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, $-(NR^4)S(O)_2OR^4$, and $-(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; $R^3$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

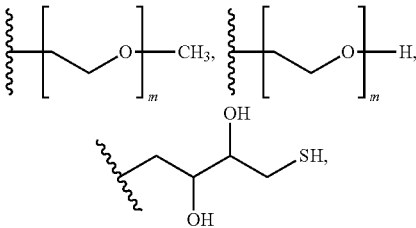

and $N^5$-(1-((carboxymethyl)amino)-1-oxo-3λ$^3$-propan-2-yl) glutamine or a pharmaceutically acceptable salt thereof, wherein m is a whole number selected from 1-1000.

In certain embodiments, the thiol has the Formula 3:

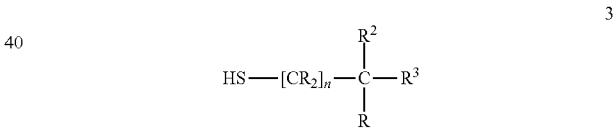

or a pharmaceutically acceptable salt or zwitterion thereof, wherein n is an integer selected from the group consisting of 0, 1, 2, 3, and 4;

R for each instance is independently selected from the group consisting of hydrogen, alkyl, aralkyl, cycloalkyl, heterocycloalkyl, aryl, and heteroaryl;

$R^2$ is hydrogen, alkyl, aralkyl, cycloalkyl, heterocycloalkyl, aryl, heteroaryl, $-N(R^4)_2$, or $-NH(C=O)R^4$;

$R^3$ is hydrogen, alkyl, aralkyl, cycloalkyl, heterocycloalkyl, aryl, heteroaryl, $-CO_2R^4$, $-(C=O)NHR^4$, $-OR^4$, or $-N(R^4)_2$; and $R^4$ for each instance is independently selected from the group consisting of hydrogen, alkyl, aralkyl, cycloalkyl, heterocycloalkyl, aryl, and heteroaryl; or the thiol is selected from the group consisting of dithiothreitol, $HS(CH_2CH_2O)_mCH_3$, $HS(CH_2CH_2O)_mH$, glutathione or a pharmaceutically acceptable salt thereof, wherein m is a whole number selected between 1-1000.

In certain embodiments, n is 1 or 2; R is hydrogen; $R^2$ is $-NHR^4$, $-NH(C=O)R^4$, or $-NH(C=O)(NR^4)_2$; and $R^3$ is hydrogen, $-OR^4$, $-CO_2R^4$, or $-(C=O)NHR^4$, wherein R[4] for each instance is independently selected from the group consisting of hydrogen and alkyl.

In certain embodiments, the thiol is selected from the group consisting of:

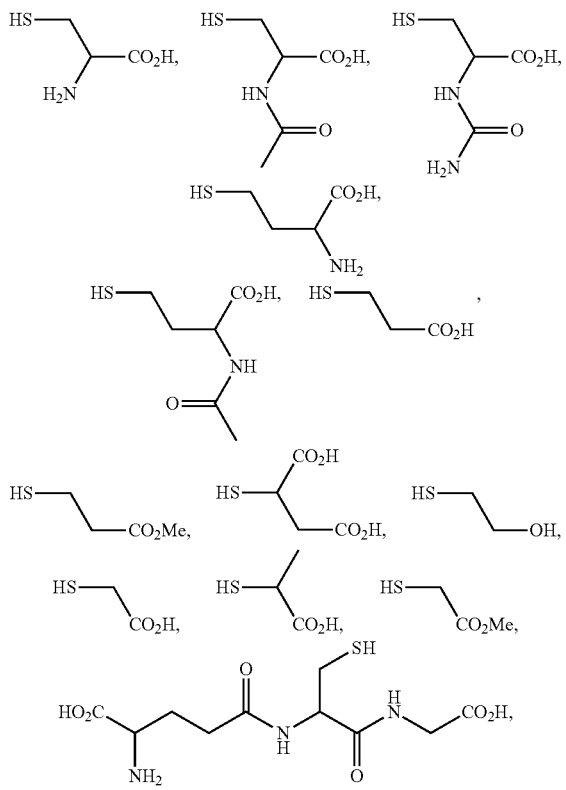

dithiothreitol, $HS(CH_2CH_2O)_mCH_3$, and $HS(CH_2CH_2O)_mH$ or a pharmaceutically acceptable salt or zwitterion thereof, wherein m is a whole number selected between 1-1000.

In certain embodiments, the step of contacting the fumaryl-crosslinked hemoglobin with a thiol or a pharmaceutically acceptable salt or zwitterion thereof, the fumaryl-crosslinked hemoglobin and the thiol are present in a molar ratio of at least 1:1; 1:2; or 1:3.

In certain embodiments, the fumaryl-crosslinked hemoglobin and the thiol are present in a molar ratio of greater than 1:3.

In certain embodiments, the thiosuccinyl-crosslinked hemoglobin is in isolated and substantially pure form.

In a fourth aspect, provided herein is a method for increasing the volume of the blood circulatory system in a subject in need thereof, wherein the method comprises transfusing into the system of the subject a therapeutically effective amount of the thiosuccinyl-crosslinked hemoglobin described herein In a fifth aspect, provided herein is a method for the treatment of shock in a subject in need thereof, wherein the method comprises transfusing into the system of the subject a therapeutically effective amount of the thiosuccinyl-crosslinked hemoglobin described herein.

In a sixth aspect, provided herein is a method of supplying oxygen to the tissues and organs in a subject in need thereof, wherein the method comprises transfusing into the system of the subject a therapeutically effective amount of the thiosuccinyl-crosslinked hemoglobin described herein.

In a seventh aspect, provided herein is a method of treating cancer in a subject in need thereof, wherein the method comprises transfusing into the system of the subject a therapeutically effective amount of the thiosuccinyl-crosslinked hemoglobin described herein, wherein the cancer is triple-negative breast cancer or colorectal cancer.

In certain embodiments, the thiosuccinyl-crosslinked hemoglobin is substantially pure.

The present disclosure relates to the modification of the fumaryl-crosslinked hemoglobin by thiols. In certain embodiments, the modification of the fumaryl-crosslinked hemoglobin by thiols alters the p50 value of the fumaryl-crosslinked hemoglobin no greater than 10%. In the examples below, the infusion of 650 mg/kg cysteinyl-succinyl crosslinked hemoglobin, which is produced by the conjugation of cysteine to the fumaryl moieties of the fumaryl-crosslinked hemoglobin, shows a significant increase in liver tissue oxygenation in a shock rat model. Moreover, its efficacy enhancement is further demonstrated by the improved restoration of blood flow in a peripheral artery disease mice model, compared to fumaryl-crosslinked hemoglobin throughout the experiment.

The present disclosure also provides a method of making the thiosuccinyl-crosslinked hemoglobin. In certain embodiments, the method comprises the steps of 1) reducing the dissolved oxygen level of the solution containing the fumaryl-crosslinked hemoglobin down to 0.1 mg/L; 2) mixing the fumaryl-crosslinked hemoglobin solution with thiol under low oxygen conditions to form the thiosuccinyl-crosslinked hemoglobin under a condition in which at least 95% of the fumaryl bridges react with the thiol reagent as well as the methemoglobin level of the thiosuccinyl-crosslinked hemoglobin is reduced to less than 2% and 3) optionally removing any residual thiols to less than 0.03% (w/w). N-acetyl cysteine (NAC) is added at a concentration of approximately 0.05-0.2% to further reduce the methemoglobin produced from the production process and also prevent its formation during storage. The present disclosure further provides a method to prepare the thiosuccinyl-crosslinked hemoglobin in high yield and purity by, e.g., adjusting the equivalence of the thiol reagent used in the coupling reaction, pH value and duration of the reaction.

The method of the present disclosure can be used to prepare thiosuccinyl-crosslinked hemoglobin having a p50 ranging from about 5-70 mmHg as measured at 37° C. and pH 7.4. Different levels of oxygen affinity are desirable, depending upon the intended chemical modification of hemoglobin and medical application. In these embodiments, the thiol-containing reagents used for conjugating to the fumaryl moieties of crosslinked hemoglobin can include, for example, cysteine, NAC, β-mercaptoethanol, and other thiol compounds as described herein. The thiosuccinyl-crosslinked hemoglobin can be a tetrameric hemoglobin with a molecular weight of about 65 kDa containing at least one (1XL), two (2XL) or three (3XL) alkyl thiol crosslinker(s) between β globin chains.

In the examples below, a solution containing cysteinyl-succinyl crosslinked bovine hemoglobin is produced by conjugating cysteine to the fumaryl moieties of fumaryl-crosslinked bovine hemoglobin. In the modification step, 40-80 mM cysteine at pH 8.0-8.3 is incubated with the tetrameric hemoglobin (tHb=7-10 g/dL) for a period of 15-30 hours at 10-30° C. under deoxygenated conditions (e.g., dissolved oxygen (DO) levels maintained below 0.1 mg/L). Up to 95% modification of the fumaryl moieties in the fumaryl-crosslinked hemoglobin by cysteine can be achieved and the methemoglobin level of the cysteinyl-succinyl crosslinked hemoglobin can be reduced to less than 2% after modification. The residual cysteine/cystine in the reaction mixture can be removed by a filtration step using a 30 kDa NMWCO membrane through which the reaction mixture can be filtered through 10-16 diafiltration volume (DV) with acetate buffer (99 mM NaCl, 46 mM sodium acetate) to bring the cysteine and cystine levels below 0.03% (w/w).

The pharmaceutical composition comprising cysteinyl-succinyl crosslinked bovine hemoglobin can be kept under nitrogen with the presence of 0.2% (w/w) NAC with the following product characteristics: tHb=9.5-10.5 g/dL, pH 7.4-8.4, $O_2$Hb ≤10%, MetHb (methemoglobin) ≤5%, endotoxin ≤0.25 EU/mL and cysteinyl-succinyl crosslinked hemoglobin in range of 95-100% purity.

The present disclosure also provides a pharmaceutical composition comprising the thiosuccinyl-crosslinked hemoglobin, such as the cysteinyl-succinyl crosslinked hemoglobin. Such compositions can be used for improving the delivery of oxygen and treatment against global and regional ischemic/hypoxic conditions, including hemorrhagic shock, myocardial ischemia reperfusion injury, peripheral artery disease and traumatic brain injury. In addition, such composition is also used for treating autoimmune diseases and cancer treatment.

BRIEF DESCRIPTION OF THE DRAWINGS

The above and other objects and features of the present disclosure will become apparent from the following description of the disclosure, when taken in conjunction with the accompanying drawings.

DETAILED DESCRIPTION

Definitions

Figure 1:
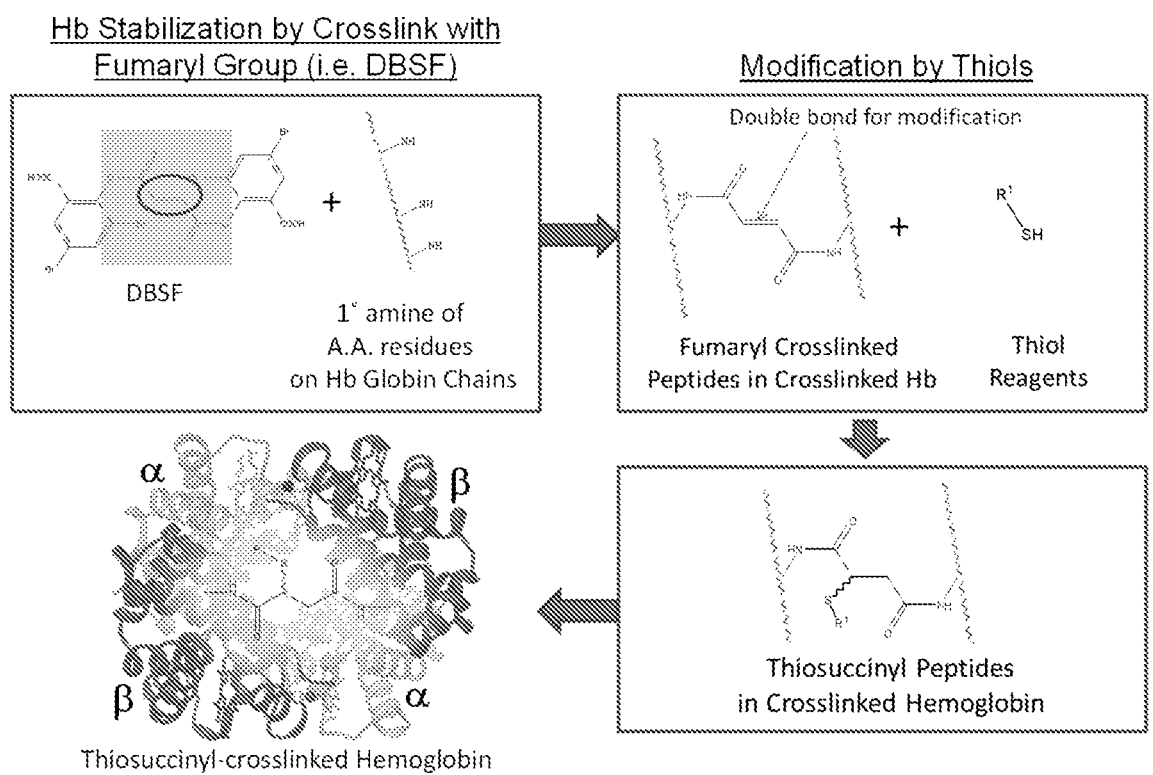
FIG. 1 is a schematic depiction of the formation of thiosuccinyl-crosslinked hemoglobin.

The following terms shall be used to describe the present invention. In the absence of a specific definition set forth herein, the terms used to describe the present invention shall be given their common meaning as understood by those of ordinary skill in the art.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

As used herein, unless otherwise indicated, the term "halo" or "halide" includes fluoro, chloro, bromo or iodo.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., C1-40 alkyl group), for example, 1-30 carbon atoms (i.e., C1-30 alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In certain embodiments, alkenyl groups can be substituted as described herein. An alkenyl group is generally not substituted with another alkenyl group, an alkyl group, or an alkynyl group.

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In certain embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In certain embodiments, aryl groups can be optionally substituted. In certain embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be optionally substituted.

The term "aralkyl" refers to an alkyl group substituted with an aryl group.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, IH-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In certain embodiments, heteroaryl groups can be substituted as described herein. In certain embodiments, heteroaryl groups can be optionally substituted.

The term "optionally substituted" refers to a chemical group, such as alkyl, cycloalkyl aryl, and the like, wherein one or more hydrogen may be replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" and "sulfone" is art-recognized and refers to —$SO_2$—. "Halide" designates the corresponding anion of the halogens.

The term "alkylthio" refers to a hydrocarbyl group having a sulfur radical attached thereto. In certain embodiments, the "alkylthio" moiety is represented by one of —S-alkyl, —S-alkenyl, or —S-alkynyl. Representative alkylthio groups include methylthio, ethylthio, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

As used herein, the term "isolated" in connection with a compound described herein means the compound is not in a cell or organism and the compound is separated from some or all of the components that typically accompany it in a cell or organism.

As used herein, the term "substantially pure" in connection with a sample of a compound described herein means the sample contains at least 60% by weight of the compound. In certain embodiments, the sample contains at least 70% by weight of the compound; at least 75% by weight of the compound; at least 80% by weight of the compound; at least 85% by weight of the compound; at least 90% by weight of the compound; at least 95% by weight of the compound; or at least 98% by weight of the compound.

As used herein, the term "substantially stroma-free" in connection with a sample of a compound described herein means the sample contains less than 5% by weight stroma. In certain embodiments, the samples contains less than 4% by weight stroma; less than 3% by weight stroma; less than 2% by weight stroma; less than 1% by weight stroma; less than 0.5% by weight stroma; less than 0.1% by weight stroma; less than 0.05% by weight stroma; or less than 0.01% by weight stroma.

The present disclosure provides a thiosuccinyl-crosslinked hemoglobin comprising a tetrameric hemoglobin and at least one thiosuccinyl crosslinking moiety of Formula 1:

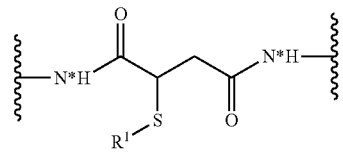

or a pharmaceutically acceptable salt or zwitterion thereof, wherein each N* independently represents a nitrogen selected from the group consisting of a nitrogen in a lysine residue side chain in the tetrameric hemoglobin and a nitrogen at a N-terminus in the tetrameric hemoglobin; and $R^1$ is alkyl, alkenyl, cycloalkyl, heterocycloalkyl, aryl, aralkyl, heteroaryl, or $-(CR_2)_nY$, wherein n is an integer number selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, $-(NR^4)S(O)_2OR^4$, and $-(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; $R^3$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

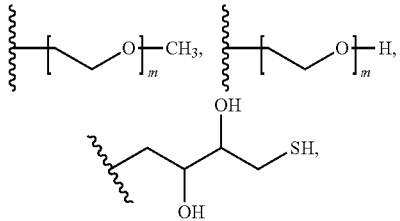

and $N^5$-(1-((carboxymethyl)amino)-1-oxo-3λ$^3$-propan-2-yl) glutamine or a pharmaceutically acceptable salt thereof, wherein m is a whole number selected from 1-1000.

While the examples below are generally directed to thiosuccinyl-crosslinked hemoglobin comprising a $\alpha_2\beta_2$ tetrameric hemoglobin, other forms of hemoglobin are also contemplated by the present disclosure, such as other tetrameric hemoglobin, e.g., $\alpha_2\gamma_2$; trimeric hemoglobin, e.g., $\alpha\beta_2$, $\alpha_2\beta$, $\alpha\gamma_2$, and $\alpha_2\gamma$; dimeric hemoglobin, e.g., $\alpha\beta$ and $\alpha\gamma$; and the like; as well as polymeric forms of hemoglobin comprising one or more monomeric forms of hemoglobin; and hemoglobin derivatives that have been subjected to other methods of chemical modification including, but not limited to, methods for conjugation to polyalkylene oxide, reaction with pyridoxal phosphate, reaction with a dialdehyde, reaction with bis-diaspirin ester, reaction with iodoacetamide or other thiol-blocking reagents, or reaction in the presence of reagents such as 2,3-diphosphoglycerate (2,3-DPG) or chemically similar compounds, or genetically crosslinked hemoglobin derivatives, such as $2\alpha\beta_2$ (dialpha beta hemoglobin), wherein the dialpha moiety comprises two alpha chains that are genetically crosslinked with, e.g., a glycine linker covalently linking the N-terminus and the C-terminus of each alpha chain.

The tetrameric hemoglobin can comprise naturally occurring and/or non-naturally occurring α, β, and γ globin chain polypeptide sequences.

The tetrameric hemoglobin can be human hemoglobin, bovine hemoglobin, porcine hemoglobin, ovine hemoglobin, equine hemoglobin, or blood from other invertebrates and recombinant and/or transgenically produced hemoglobin.

In instances in which the tetrameric hemoglobin is human hemoglobin [e.g., comprising two α globin chain (UniProt Accession Number: P69905); and two β globin chains (UniProt Accession Number: P68871)], each N* may independently represent a nitrogen present in any one or more of amino acid residues at position 1, 8, 12, 17, 41, 57, 61, 62, 91, 100, 128, and 140 of the α globin chains; or at position 1, 9, 18, 60, 62, 66, 67, 83, 96, 121, 133, and 145 of the β globin chains. In certain embodiments, each N* independently represents a nitrogen present in the amino acid residues at position 100 of the α globin chains.

In instances in which the tetrameric hemoglobin is bovine hemoglobin [e.g., comprising two α globin chain (UniProt Accession Number: P01966); and two β globin chains (UniProt Accession Number: P02070)], each N* may independently represent a nitrogen present in any one or more of amino acid residues at position 1, 8, 12, 17, 41, 57, 62, 69, 91, 100, 128, and 140 of the α globin chains; or at position 1, 7, 16, 18, 58, 60, 64, 65, 75, 81, 94, 103, 119, and 131 of the β globin chains. In certain embodiments, each N* independently represents a nitrogen present in any one or more of amino acid residues and 1 and 81 of the β globin chains.

In instances in which the tetrameric hemoglobin is porcine hemoglobin [e.g., comprising two α globin chain (UniProt Accession Number: P01965); and two β globin chains (UniProt Accession Number: P02067)], each N* may independently represent a nitrogen present in any one or more of amino acid residues at position 1, 7, 11, 16, 40, 56, 61, 68, 90, 99, 127, and 139 of the α globin chains; or at position 1, 9, 18, 60, 62, 66, 67, 77, 83, 88, 133 and 145 of the β globin chains. The presence of oxygen in the cross-linking reaction is also known to affect the p50 value of the resulting crosslinked hemoglobin. Depending on the oxygen content in the fumaryl crosslinking reaction, the p50 value of the resulting fumaryl-crosslinked hemoglobin, as well as the thiosuccinyl-crosslinked hemoglobin, can have a value ranging from 5-70 mmHg.

In certain embodiments, the hemoglobin is crosslinked under oxygenated conditions, to give a fumaryl-crosslinked hemoglobin, as well as the thiosuccinyl-crosslinked hemoglobin, with a p50 value of 5-20 mmHg or 10-20 mmHg. In certain embodiments, the hemoglobin is crosslinked under deoxygenated conditions, to give a fumaryl-crosslinked hemoglobin, as well as the thiosuccinyl-crosslinked hemoglobin, with a p50 value of 20-70 mmHg; 20-70 mmHg; 30-70 mmHg; 40-70 mmHg; 40-60 mmHg; 38-50 mmHg; 45-65 mmHg; or 55-65 mmHg.

In instances in which the hemoglobin is first thioblocked by reaction of the hemoglobin with iodoacetamide thereby forming a thioblocked hemoglobin; crosslinking the thus formed thioblocked hemoglobin with the a fumaryl cross-linking agent thereby forming a fumaryl-crosslinked thioblocked hemoglobin; and contacting the fumaryl-crosslinked thioblocked hemoglobin with a thiol or a pharmaceutically acceptable salt or zwitterion thereof thereby forming a thiosuccinyl-crosslinked thioblocked hemoglobin, the p50 value of the resulting thiosuccinyl-crosslinked thioblocked hemoglobin crosslinked under deoxygenated conditions can range from 15-50 mmHg; 25-50 mmHg; or 35-50 mmHg, while the p50 value of the resulting thiosuccinyl-crosslinked thioblocked hemoglobin crosslinked under oxygenated condition can range from 5-20 mmHg; 5-15 mmHg, 5-10 mmHg or 10-15 mmHg.

In certain embodiments, $R^1$ is alkyl or $-(CR_2)_nY$; or $R^1$ is a moiety selected from the group consisting of:

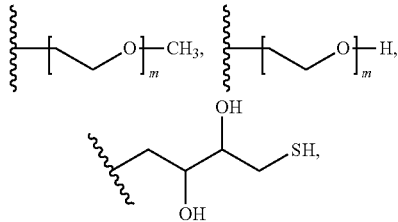

and $N^5$-(1-((carboxymethyl)amino)-1-oxo-3$\lambda^3$-propan-2-yl) glutamine or a pharmaceutically acceptable salt thereof, wherein m is a whole number selected from 1-1000.

In instances in which $R^1$ is:

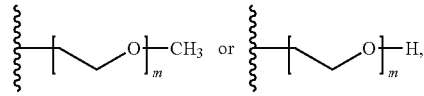

m can be 1-1000, 1-900, 1-800, 1-700, 1-600, 1-500, 1-400, 1-300, 1-200, 1-100, 1-50, 1-25, 1-20, 1-15, 1-10, or 1-5.

In instances in which $R^1$ is $-(CR_2)_nY$, n can be 0-10, 0-9, 0-8, 0-7, 0-6, 0-5, 0-4, 0-3, 0-2, 0-1, 1-10, 1-9, 1-8, 1-7, 1-6, 1-5, 1-4, 1-3, or 1-2. In certain embodiments, each R is independently hydrogen or alkyl. In certain embodiments, $R^1$ is $-(CH_2)_nY$.

In certain embodiments, Y is $-(CRR^2R^3)$, wherein R for each instance is independently selected from the group consisting of hydrogen, alkyl, aralkyl, cycloalkyl, heterocycloalkyl, aryl, and heteroaryl; $R^2$ is hydrogen, alkyl, aralkyl, cycloalkyl, heterocycloalkyl, aryl, heteroaryl, $-N(R^4)_2$, or $-NH(C=O)R^4$; $R^3$ is hydrogen, alkyl, aralkyl, cycloalkyl, heterocycloalkyl, aryl, heteroaryl, $-CO_2R^4$, $-(C=O)NHR^4$, $-OR^4$, or $-N(R^4)_2$; and $R^4$ for each instance is independently selected from the group consisting of hydrogen, alkyl, aralkyl, cycloalkyl, heterocycloalkyl, aryl, and heteroaryl. In certain embodiments, R is hydrogen. In certain embodiments, $R^2$ is $-N(R^4)_2$ or $-NH(C=O)R^4$; and $R^3$ is $-CO_2R^4$, $-(C=O)NHR^4$, $-OR^4$, or $-N(R^4)_2$.

In certain embodiments, Y is $-(CRR^2R^3)$, wherein, R is hydrogen; $R^2$ is hydrogen, $-N(R^4)_2$, $-NH(C=O)R^4$, or $-NH(C=O)N(R^4)_2$; and $R^3$ is $-CO_2R^4$, $-(C=O)NHR^4$, $-OR^4$, or $-N(R^4)_2$.

In certain embodiments, $R^1$ is $-(CH_2)_n(CHR^2R^3)$, wherein n is 1, 2, 3, or 4; $R^2$ is $-N(R^4)_2$ or $-NH(C=O)R^4$; $R^3$ is $-CO_2R^4$ or $-(C=O)NHR^4$; and each $R^4$ is independently selected from the group consisting of hydrogen, alkyl, cycloalkyl, aryl, and heteroaryl.

In certain embodiments, $R^1$ is $-(CH_2)_n(CHR^2R^3)$, wherein n is 1, 2, 3, or 4; $R^2$ is $-N(R^4)_2$ or $-NH(C=O)R^4$; $R^3$ is $-CO_2H$; and each $R^4$ is independently selected from the group consisting of hydrogen or alkyl.

In certain embodiments, $R^1$ is selected from the group consisting of:

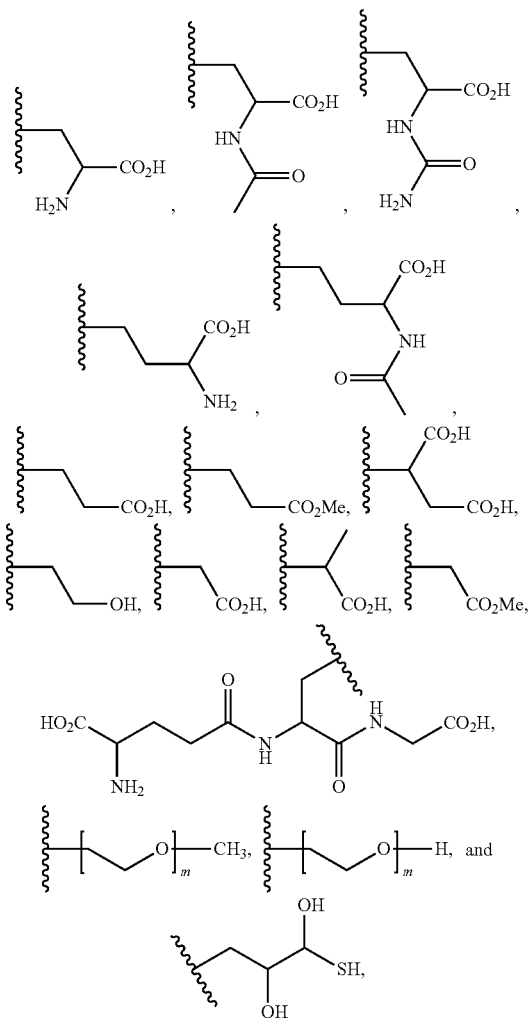

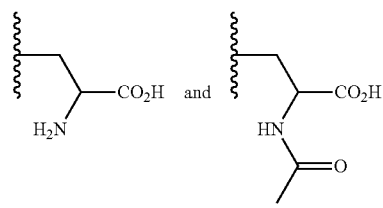

or a pharmaceutically acceptable salt of zwitterion thereof, wherein m is a whole number selected from 1-1000.

In certain embodiments, the thiosuccinyl-crosslinked hemoglobin comprises a $\alpha_2\beta_2$ tetrameric bovine hemoglobin comprising two α globin chains (UniProt Accession Number: P01966) and two β globin chains (UniProt Accession Number: P02070), wherein the β globin chains are crosslinked with at least one thiosuccinyl crosslinking moiety of Formula 1, wherein $R^1$ is selected from the group consisting of:

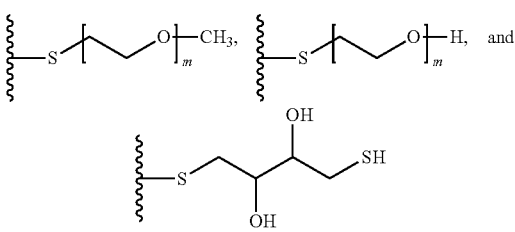

or a pharmaceutically acceptable salt or zwitterion thereof, wherein at least one N* represents the nitrogen at the N-terminus of a β globin chain and at least one N* represents the nitrogen in the lysine side chain at position 81 of a β globin chain.

In alternative embodiments, the present disclosure also provides analogs in which the sulfur depicted in Formula 1 is replaced with selenium, disulfide, and diselenides, wherein $R^1$ and each N* are as defined in any one or more embodiments described herein.

In alternative embodiments, the present disclosure also provides a thiosuccinyl-crosslinked hemoglobin comprising a tetrameric hemoglobin and at least one thiosuccinyl crosslinking moiety of Formula 1a:

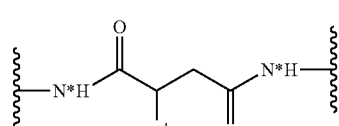

1a or a conjugate salt or zwitterion thereof, wherein each N* independently represents a nitrogen selected from the group consisting of a nitrogen in a lysine residue side chain in the hemoglobin and a nitrogen at a N-terminus in the hemoglobin; and $R^1$ is an alkylthio group.

In certain embodiments, the alkylthio group is a moiety of Formula 2a:

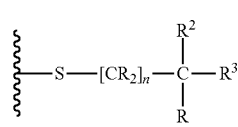

2a wherein n is an integer selected from the group consisting of 0, 1, 2, 3, and 4; R for each instance is independently selected from the group consisting of hydrogen, alkyl, aralkyl, cycloalkyl, heterocycloalkyl, aryl, and heteroaryl; $R^2$ is hydrogen, alkyl, aralkyl, cycloalkyl, heterocycloalkyl, aryl, heteroaryl, —N($R^4$)$_2$, or —NH(C═O)$R^4$; $R^3$ is hydrogen, alkyl, aralkyl, cycloalkyl, heterocycloalkyl, aryl, heteroaryl, —CO$_2$$R^4$, —(C═O)NH$R^4$, —O$R^4$, or —N($R^4$)$_2$; and $R^4$ for each instance is independently selected from the group consisting of hydrogen, alkyl, aralkyl, cycloalkyl, heterocycloalkyl, aryl, and heteroaryl; or the alkylthio group is a moiety selected from the group consisting of:

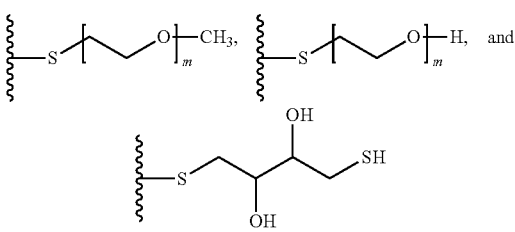

or a conjugate salt thereof, wherein m is a whole number selected from 1-1000.

In certain embodiments, n is 1 or 2; R is hydrogen; $R^2$ is —NH$R^4$, or —NH(C═O)$R^4$; and $R^3$ is hydrogen, —O$R^4$, —CO$_2$$R^4$, or —(C═O)NH$R^4$, wherein $R^4$ for each instance is independently selected from the group consisting of hydrogen and alkyl.

In certain embodiments, the alkylthio group is selected from the group consisting of:

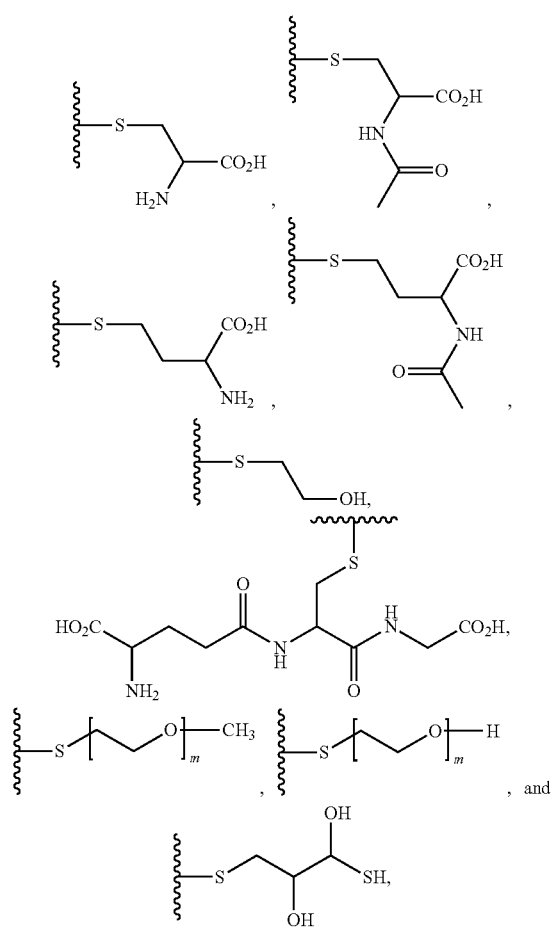

or a conjugate salt of zwitterion thereof, wherein m is a whole number selected from 1-1000.

In certain embodiments, the thiosuccinyl-crosslinked hemoglobin is isolated and/or substantially pure. In certain embodiments, the thiosuccinyl-crosslinked hemoglobin is substantially stroma-free.

The present disclosure also provides a pharmaceutical composition comprising a thiosuccinyl-crosslinked hemoglobin described herein and at least one pharmaceutically acceptable excipient and/or pharmaceutically acceptable carrier.

The thiosuccinyl-crosslinked hemoglobin described herein and their pharmaceutically acceptable salts can be administered to a subject either alone or in combination with pharmaceutically acceptable carriers or diluents in a pharmaceutical composition according to standard pharmaceutical practice. The thiosuccinyl-crosslinked hemoglobin can be administered parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of the thiosuccinyl-crosslinked hemoglobin described herein, formulated together with one or more pharmaceutically acceptable carriers (additives) and/or diluents. The pharmaceutical compositions of the present disclosure may be specially formulated for administration in liquid form, including those adapted for the following: (1) parenteral administration, for example, by intravenous as, for example, a sterile solution or suspension.

As set out herein, certain embodiments of the thiosuccinyl-crosslinked hemoglobin described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of thiosuccinyl-crosslinked hemoglobin of the present disclosure. These salts can be prepared in situ in the administration vehicle or the dosage form manufacturing process, or by separately reacting a purified thiosuccinyl-crosslinked hemoglobin of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the thiosuccinyl-crosslinked hemoglobin described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of the thiosuccinyl-crosslinked hemoglobin of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the thiosuccinyl-crosslinked hemoglobin include the step of bringing into association a thiosuccinyl-crosslinked hemoglobin described herein with the carrier and, optionally, one or more accessory ingredients. In general, the formulations are prepared by uniformly and intimately bringing into association a compound described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more thiosuccinyl-crosslinked hemoglobins described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars (such as sucrose), alcohols, non-ionic surfactants (such as Tween 20), antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The pharmaceutical composition may comprise between 3-15 g/dL of the thiosuccinyl-crosslinked hemoglobin. In certain embodiments, the pharmaceutical composition comprises between 4-15 g/dL; 5-15 g/dL; 5-14 g/dL; 6-14 g/dL; 7-13 g/dL; 8-12 g/dL; 9-11 g/dL; or 9.5-10.5 g/dL of the thiosuccinyl-crosslinked hemoglobin. In certain embodiments, the pharmaceutical composition comprises isolated and substantially pure thiosuccinyl-crosslinked hemoglobin.

In certain embodiments, the pharmaceutical composition comprises one or more thiosuccinyl-crosslinked hemoglobin selected from the group consisting of thiosuccinyl-crosslinked hemoglobin comprising one, two, and three thiosuccinyl crosslinking moieties of Formula 1. The number of different thiosuccinyl-crosslinked hemoglobin present in the pharmaceutical composition and their relative amounts can be readily controlled by modifying the reaction conditions of the crosslinking reaction and/or by separating undesired fumaryl-crosslinked hemoglobin crosslinking and/or thiosuccinyl-crosslinked hemoglobin thiol addition products by purification. In certain embodiments, the pharmaceutical composition comprises a thiosuccinyl-crosslinked hemoglobin having one thiosuccinyl crosslinking moiety of Formula 1; a thiosuccinyl-crosslinked hemoglobin having two thiosuccinyl crosslinking moieties of Formula 1; and a thiosuccinyl-crosslinked hemoglobin having three thiosuccinyl crosslinking moieties of Formula 1. In certain embodiments, the pharmaceutical composition comprises a thiosuccinyl-crosslinked hemoglobin having one thiosuccinyl crosslinking moiety of Formula 1; a thiosuccinyl-crosslinked hemoglobin having two thiosuccinyl crosslinking moieties of Formula 1; and a thiosuccinyl-crosslinked hemoglobin having three thiosuccinyl crosslinking moieties of Formula 1 in a mass ratio of 2.8-3.4:5.6-6.2:0.7-1.3; 2.9-3.3:5.7-6.1:0.8-1.2; 3.0-3.2:5.8-6.0:0.9-1.1; or 3.1:5.9:1.0, respectively.

In certain embodiments, the pharmaceutical composition comprises a thiosuccinyl-crosslinked hemoglobin having one thiosuccinyl crosslinking moiety of Formula 1 at 0.1-99%; 0.1-95%; 0.1-90%; 0.1-80%; 0.1-70%; 0.1-60%; 0.1-50%; 10-50%; 20-50%; 20-40%; 25-45%; or 25-35% wt/wt with respect to the total weight of all of the thiosuccinyl-crosslinked hemoglobin present in the pharmaceutical composition (e.g., relative to the total weight of the thiosuccinyl-crosslinked hemoglobin having one thiosuccinyl crosslinking moiety of Formula 1; the thiosuccinyl-crosslinked hemoglobin having two thiosuccinyl crosslinking moieties of Formula 1; and the thiosuccinyl-crosslinked hemoglobin having three thiosuccinyl crosslinking moieties of Formula 1 present in the pharmaceutical composition).

In certain embodiments, the pharmaceutical composition comprises a thiosuccinyl-crosslinked hemoglobin having two thiosuccinyl crosslinking moiety of Formula 1 at 0.1-99%; 0.1-95%; 0.1-90%; 10-90%; 20-90%; 20-80%; 20-70%; 30-70%; 40-70%; 50-70%; 50-60%; or 55-65% wt/wt with respect to the total weight of all of the thiosuccinyl-crosslinked hemoglobin present in the pharmaceutical composition.

In certain embodiments, the pharmaceutical composition comprises a thiosuccinyl-crosslinked hemoglobin having three thiosuccinyl crosslinking moiety of Formula 1 at 0.1-99%; 0.1-95%; 0.1-90%; 0.1-80%; 0.1-70%; 0.1-60%; 0.1-50%; 0.1-40%; 0.1-30%; 0.1-20%; 5-20%; or 5-15% wt/wt with respect to the total weight of all of the thiosuccinyl-crosslinked hemoglobin present in the pharmaceutical composition.

The pharmaceutical composition can comprise the fumaryl crosslinked hemoglobin in less than 10%, less than 9%, less 8%, less than 7%, less than 6%, less than 5%, less than 4%, less than 3%, less than 2%, less than 1% by weight, less than 0.5%, or less than 0.1% by weight; or substantially no fumaryl crosslinked hemoglobin.

The thiosuccinyl-crosslinked hemoglobin and the fumaryl crosslinked hemoglobin may be present in the pharmaceutical composition in a mass ratio of 90:10 to 99.99:0.01. In certain embodiments, the thiosuccinyl-crosslinked hemoglobin and the fumaryl crosslinked hemoglobin may be present in the pharmaceutical composition in a mass ratio of 91:9 to 99.99:0.01; 92:8 to 99.99:0.01; 93:7 to 99.99:0.01; 94:6 to 99.99:0.01; 95:5 to 99.99:0.01; 96:4 to 99.99:0.01; 97:3 to 99.99:0.01; 98:2 to 99.99:0.01; 99:1 to 99.99:0.01; 99.5:0.5 to 99.99:0.01; or 99.9:0.1 to 99.99:0.01, respectively. In certain embodiments, the pharmaceutical composition comprises substantially no fumaryl crosslinked hemoglobin.

In certain embodiments, the pharmaceutical composition further comprises an antioxidant. Exemplary antioxidants include, but are not limited to, cysteine, N-acetyl cysteine, γ-glutamyl-cysteine, glutathione, 2,3-dimercapto-1-propanol, 1,4-butanedithiol, sodium dithionite, other biologically compatible thiols and ascorbate. The antioxidant can inhibit or reverse the formation of methemoglobin.

In certain embodiments, the pharmaceutical composition comprises 5% (w/w) or less of the antioxidant. In certain embodiments, the pharmaceutical composition comprises 4.5% (w/w) or less; 4.0% (w/w) or less; 3.5% (w/w) or less; 3.0% (w/w) or less; 2.5% (w/w) or less; 2.0% (w/w) or less;

1.5% (w/w) or less; 1.0% (w/w) or less; 0.9% (w/w) or less; 0.8% (w/w) or less; 0.7% (w/w) or less; 0.6% (w/w) or less; 0.5% (w/w) or less; 0.4% (w/w) or less; 0.3% (w/w) or less; 0.2% (w/w) or less; or 0.1% (w/w) or less of the antioxidant. In certain embodiments, the pharmaceutical composition comprises between 0.001 to 1% (w/w); 0.01 to 1% (w/w); 0.01 to 1% (w/w); 0.01 to 0.9% (w/w); 0.01 to 0.8% (w/w); 0.01 to 0.7% (w/w); 0.01 to 0.6% (w/w); 0.01 to 0.5% (w/w); 0.01 to 0.4% (w/w); 0.01 to 0.3% (w/w); 0.05 to 0.3% (w/w); 0.1 to 0.3% (w/w); or 0.15 to 0.25% (w/w) antioxidant.

In certain embodiments, the pharmaceutical composition includes less than about 10%, 9%, 8%, 7%, 6%, 5%, 4%, 3%, 2%, 1%, 0.5%, or 0.1% by weight methemoglobin.

In certain embodiments, provided herein is a solid pharmaceutical composition comprising a thiosuccinyl-crosslinked hemoglobin as described herein, NAC, sucrose, and Tween 20.

In certain embodiments, provided herein is a pharmaceutical composition comprising a thiosuccinyl-crosslinked hemoglobin as described herein, NAC, NaCl, and sodium acetate. In certain embodiments, the pharmaceutical composition comprising a thiosuccinyl-crosslinked hemoglobin as described herein, NAC, NaCl, sodium acetate, sucrose, and Tween 20.

The present disclosure also provides methods of preparing the thiosuccinyl-crosslinked hemoglobin described herein. The thiosuccinyl-crosslinked hemoglobin can readily be prepared by any number of well-known methods known to those of ordinary skill in the art.

In certain embodiments, the method for preparing the thiosuccinyl-crosslinked hemoglobin comprises: contacting a tetrameric hemoglobin with a fumaryl crosslinking agent thereby forming a fumaryl-crosslinked hemoglobin; contacting the fumaryl-crosslinked hemoglobin with a thiol or a pharmaceutically acceptable salt or zwitterion thereof thereby forming the thiosuccinyl-crosslinked hemoglobin.

Any fumaryl crosslinking agent that is capable of intramolecularly crosslinking hemoglobin known in the art can be used in the methods described herein. In certain embodiments, the fumaryl crosslinking agent can be represented by a compound of Formula 4:

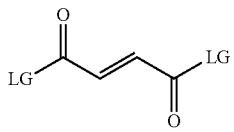

wherein each LG can independently be any leaving group in the art. Exemplary leaving groups include, but are not limited to, Cl, Br, I, 3,5-dibromosalicylate, salicylate, or the like.

In certain embodiments, LG is selected from the group consisting of:

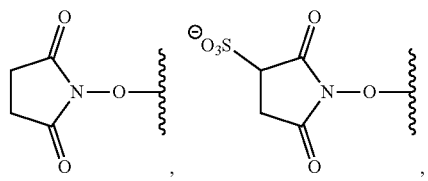

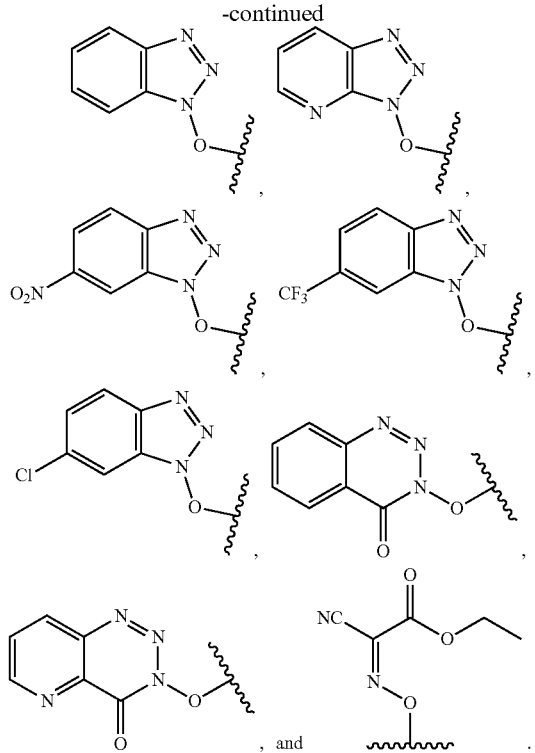

The compound of Formula 4 can be performed or formed in situ, e.g., by reaction of fumaric acid with a carbonyl activating agent and optionally a coupling additive.

Exemplary carbonyl activating agents include, but are not limited to, carbodiimide, such as DCC, DIC, EDC, CIC, BMC, CPC, BDDC, PIC, PEC, and BEM, a uronium/aminium salt, such as HATU, HBTU, TATU, TBTU, HAPyU, TAPipU, HAPipU, HBPipU, HAMBU, HBMDU, HAMTU, 5,6-B(HATU), 4,5-B(HATU), HCTU, TCTU, and ACTU, phosphonium salts, such as AOP, BOP, PyAOP, PyBOP, PyOxm, PyNOP, PyFOP, NOP, and PyClock, immonium salts, such as BOMI, BDMP, BMMP, BPMP, and AOMP.

Exemplary coupling additives include, but are not limited to, HOBt, 6-NO$_2$—HOBt, 6-Cl—HOBt, 6-CF$_3$—HOBt, HOAt, HODhbt, HODhat, HOSu, and Oxyma.

In certain embodiments, the crosslinking agent is a salicyl fumarate analog, wherein the aryl rings of each of the salicyl groups is independently optionally substituted.

In certain embodiments, the crosslinking agent is selected from the group consisting of bis-3,5-dibromosalicyl fumarate (DBSF), fumaryl chloride and bis(salicyl) fumarate.

In the step of contacting the crosslinking agent and the tetrameric hemoglobin, the molar ratio of the crosslinking agent and the tetrameric hemoglobin can be between 0.8:1 to 20:1, respectively. In certain embodiments, the crosslinking agent and the tetrameric hemoglobin are present a molar ratio between 0.8:1 to 19:1; 0.8:1 to 18:1; 0.8:1 to 17:1; 0.8:1 to 16:1; 0.8:1 to 15:1; 0.8:1 to 14:1; 0.8:1 to 13:1; 0.8:1 to 12:1; 0.8:1 to 11:1; 0.8:1 to 10:1; 0.8:1 to 9:1; 0.8:1 to 8:1; 0.8:1 to 7:1; 0.8:1 to 6:1; 0.8:1 to 5:1; 0.8:1 to 4:1; 0.8:1 to 3.5:1; 0.8:1 to 3:1; 0.8:1 to 2.5:1; 0.8:1 to 2:1; 0.8:1 to 1.5:1; 1:1 to 3:1; 1.1:1 to 3:1; 1.5:1 to 3:1; 2:1 to 3:1; or 2.25:1 to 2.75:1, respectively.

In the step of contacting the crosslinking agent and the tetrameric hemoglobin, the concentration of the tetrameric hemoglobin can be between 5-25 g/dL. In certain embodiments, the concentration of the tetrameric hemoglobin in the step of contacting the crosslinking agent and the tetrameric hemoglobin can be between 5-20 g/dL; 10-20 g/dL; 10-18 g/dL; 10-16 g/dL; 10-15 g/dL; 11-15 g/dL; 12-15 g/dL; or 13-15 g/dL.

The tetrameric hemoglobin can be reacted with the crosslinking agent in a polar protic solvent, such as in an aqueous solution. In certain embodiments, the crosslinking reaction takes place in water.

In order to facilitate the crosslinking reaction, the pH of the reaction solvent can be maintained at a pH greater than 7. In certain embodiments, the pH of the crosslinking reaction solvent has a pH between 7-10; 8-10; 8.5 to 9.5; 8.7 to 9.3; or 8.9 to 9.1.

The thus formed fumaryl-crosslinked hemoglobin can optionally purified using any method known to those skilled in the art, such as by filtration, heat-induced precipitation, centrifugation, chromatography, and the like.

The fumaryl-crosslinked hemoglobin can then reacted with the thiol thereby forming the thiosuccinyl-crosslinked hemoglobin.

The thiol can be represented by the formula $R^1SH$ as defined in any embodiment described herein.

The fumaryl-crosslinked hemoglobin can be present in the reaction with the thiol at a concentration between 5-20 g/dL. In certain embodiments, the fumaryl-crosslinked hemoglobin is present in the reaction with the thiol at a concentration between 5-18 g/dL; 5-16 g/dL; 5-14 g/dL; 5-12 g/dL; 7-12 g/dL; 8-12 g/dL; or 9-11 g/dL.

The thiol can be present in the reaction with the fumaryl-crosslinked hemoglobin at a concentration between 1-500 mM. In certain embodiments, the thiol can be present in the reaction with the fumaryl-crosslinked hemoglobin at a concentration between 1-450 mM; 1-400 mM; 1-350 mM; 1-300 mM; 1-250 mM; 1-200 mM; 1-180 mM; 1-160 mM; 1-140 mM; 1-120 mM; 1-100 mM; 10-100 mM; 20-100 mM; 30-100 mM; 30-90 mM; 40-80 mM; 77.5-310 mM, 174-3110 mM, 9.7-77.5 mM; 19.4-77.5 mM; or 38.8-77.5 mM.

The reaction of the thiol and the fumaryl-crosslinked hemoglobin can be conducted at a pH between 7-11. In certain embodiments, the reaction of the thiol and the fumaryl-crosslinked hemoglobin is conducted at a pH between 7-11; 7-10; 7.4 to 10; 7.4 to 9, 7.4 to 8.2, or 8.2 to 9. The pH of the thiol addition reaction solvent can be maintained at the desired pH by use of pH buffer within the desired range or the addition of a Brønsted base to the reaction mixture, as needed. The selection of the appropriate Brønsted base or pH buffer is well within the skill of a person of ordinary skill in the art. Useful Brønsted bases include, but are not limited to Group I and Group II hydroxides, carbonates, and bicarbonates; organic amines, and the like.

The fumaryl-crosslinked hemoglobin can be reacted with the thiol in a polar protic solvent, such as in an aqueous solution. In certain embodiments, the thiol addition reaction takes place in water.

The reaction of the thiol with the fumaryl-crosslinked hemoglobin can generally conducted until all of the fumaryl-crosslinked hemoglobin starting material is converted to the desired thiosuccinyl-crosslinked hemoglobin, the fumaryl-crosslinked hemoglobin no longer is being converted to the desired thiosuccinyl-crosslinked hemoglobin, and/or the concentration of impurities and/or side products increases beyond a desired amount. Depending on the reaction conditions, the reaction of the thiol with the fumaryl-crosslinked hemoglobin can take between 1-72 hr; 6-72 hr, 12-72 hr, 24-72 hr, 36-72 hr, 48-72 hr, 60-72 hr, 12-48 hr, or 24-48 hr. In cases in which the rate of reaction of the thiol with the fumaryl-crosslinked hemoglobin is very slow (e.g., such as in the case of certain high molecular weight PEGylated thiols), the reaction of the thiol with the fumaryl-crosslinked hemoglobin can take up to one month.

The thus formed thiosuccinyl-crosslinked hemoglobin can optionally purified using any method known to those skilled in the art, such as by filtration, heat-induced precipitation, centrifugation, chromatography, and the like.

The present disclosure also provides therapeutic methods of using the thiosuccinyl-crosslinked hemoglobin described herein. The thiosuccinyl-crosslinked hemoglobin can be used in any therapeutic methods that hemoglobin based oxygen carriers can be used.

The present disclosure provides a method for increasing the volume of the blood circulatory system in a subject in need thereof, wherein the method comprises transfusing into the system of the subject a therapeutically effective amount of the thiosuccinyl-crosslinked hemoglobin according to any embodiment or combination of embodiments described herein. In certain embodiments, the subject suffers from hemorrhagic shock.

The present disclosure provides a method of supplying oxygen to the tissues and organs in a subject in need thereof, wherein the method comprises transfusing into the system of the subject a therapeutically effective amount of the thiosuccinyl-crosslinked hemoglobin according to any embodiment or combination of embodiments described herein. In certain embodiments, the subject suffers from ischemia, including for example myocardial ischemia-reperfusion injury. The ischemia can be global or regional.

The present disclosure provides a method of treating cancer in a subject in need thereof, wherein the method comprises transfusing into the system of the subject a therapeutically effective amount of the thiosuccinyl-crosslinked hemoglobin according to any embodiment or combination of embodiments described herein. The thiosuccinyl-crosslinked hemoglobin can be administered alone or in combination with one or more cancer therapeutics and/or radiotherapy to treat cancer.

In certain embodiments, the cancer is selected from the group consisting of leukemia, head and neck cancer, colorectal cancer, lung cancer, breast cancer, liver cancer, nasopharyngeal cancer, esophageal cancer and brain cancer. In certain embodiments, the cancer is triple-negative breast cancer or colorectal cancer.

The cancer therapeutic can be bortezomib, 5-fluorouracil, doxorubicin, or cisplatin.

The present disclosure also provides a method of treating systemic lupus erythematosus in a subject in need thereof, wherein the method comprises transfusing into the system of the subject a therapeutically effective amount of the thiosuccinyl-crosslinked hemoglobin according to any embodiment or combination of embodiments described herein.

The present disclosure also provides a method of treating peripheral artery disease in a subject in need thereof, wherein the method comprises transfusing into the system of the subject a therapeutically effective amount of the thiosuccinyl-crosslinked hemoglobin according to any embodiment or combination of embodiments described herein.

The present disclosure also provides a method of treating traumatic brain injury in a subject in need thereof, wherein the method comprises transfusing into the system of the subject a therapeutically effective amount of the thiosuccinyl-crosslinked hemoglobin according to any embodiment or combination of embodiments described herein.

EXAMPLES

Example 1: Process Overview

Figure 2:
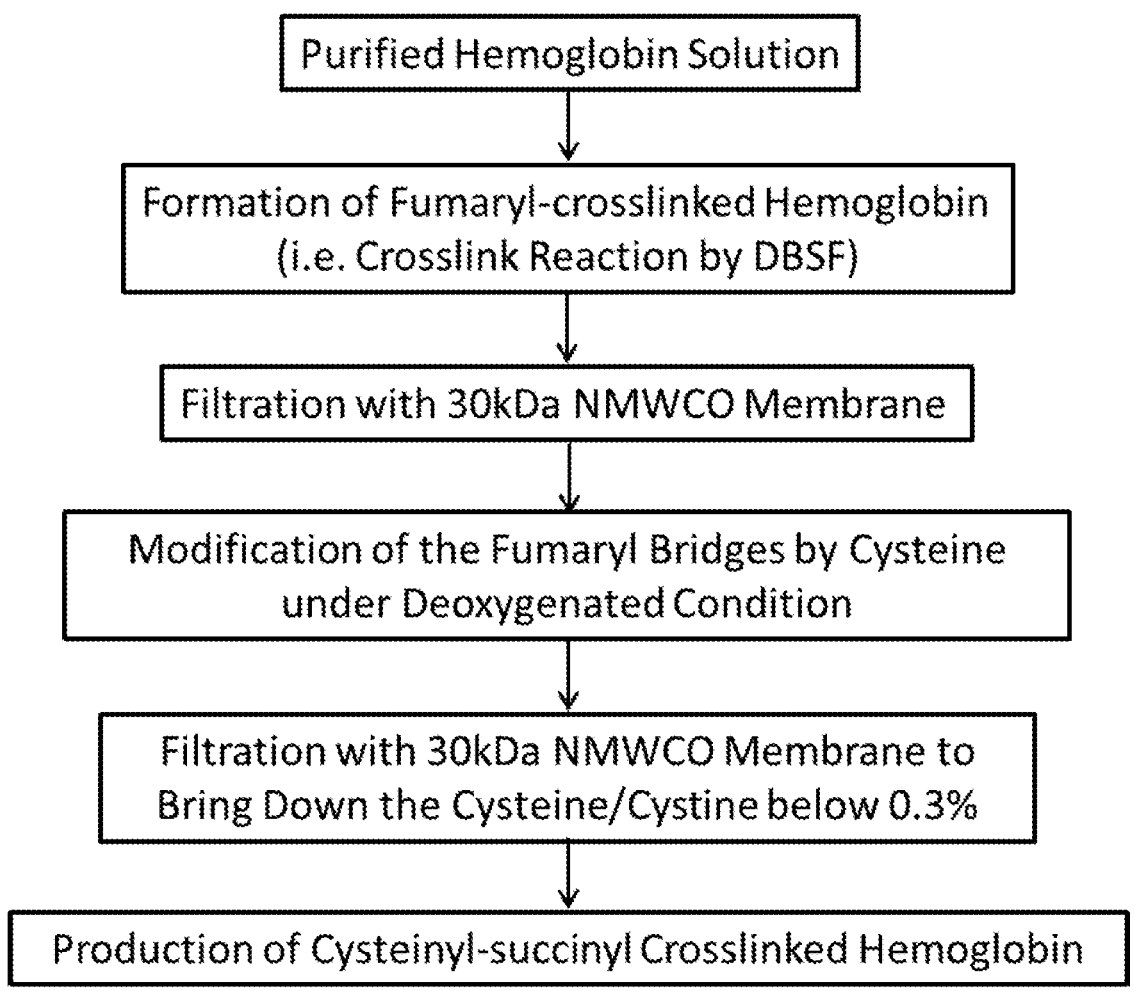
FIG. 2 is a flow-chart depicting the method of formation of cysteinyl-succinyl crosslinked hemoglobin.

An exemplary schematic flow diagram of the process of making cysteinyl-succinyl crosslinked hemoglobin, is illustrated in FIG. 2. Bovine whole blood collected from the slaughter house was processed, lysed and purified by ultrafiltration step and column chromatography to produce highly purified hemoglobin solution (PHS). To prevent the dissociation of the hemoglobin into heterodimer, the tetrameric hemoglobin was stabilized by crosslinking reaction with DBSF while the residual DBSF and hydrolyzed derivatives were removed by ultrafiltration step to bring the DBSF and 3-5, dibromosalicylic acid (DBSA) levels to below 0.03% (w/w). The hemoglobin crosslinked by fumaryl bridges (fumaryl-crosslinked hemoglobin) was modified by 1,4-addition reaction of cysteine with the fumaryl moieties present in the fumaryl-crosslinked hemoglobin to form cysteinyl-succinyl crosslinked hemoglobin with <2% methemoglobin level under deoxygenated conditions and followed by an ultrafiltration purification step to bring the cysteine and cystine levels to below 0.03% (w/w). To reduce the level of met-hemoglobin, N-acetyl cysteine at a concentration of 0.05% to 0.2% was added to the solution containing the above-mentioned cysteinyl-succinyl crosslinked hemoglobin.

Example 2: Preparation of Highly Purified Bovine Hemoglobin Solution

Blood cells were separated from the whole bovine blood through centrifugation and the collected blood cells were subjected to a cell washing step (Lima, M. C., 2007, Artif Cells Blood Substit Immobil Biotechnol, 35(4):431-47). In certain embodiments, the method for the isolation and purification of hemoglobin from blood cells described in the literature can be used to prepare the hemoglobin used in the current method (Houtchens, R. A. & Rausch, C. W., 2000, U.S. Pat. No. 6,150,507; Wong, B. L. & Kwok, S. Y., 2011, U.S. Pat. No. 7,989,593 B1). The residual amount of plasma was further removed from the collected blood cells by hollow fiber filtration step. A hypotonic solution was mixed with the washed blood cells to release the intracellular hemoglobin through a tightly controlled process. The cell debris were removed from cell lysate via a 0.2 μm filtration step and followed by additional ultrafiltration steps to partially remove the impurities to form a partially purified hemoglobin solution. To further purify the hemoglobin solution, the hemoglobin solution was buffer exchanged to contain minimal salt concentration prior to the negative mode anion column chromatography step. The flow through fraction containing highly purified hemoglobin was collected for which the pH, tHb and salt concentration were adjusted, sterile filtered and stored at 2-8° C. prior to the downstream process. With a tight process control for the preparation of stroma-free hemoglobin, the quality and purity of the highly purified hemoglobin were analyzed and are summarized in Table 1.

TABLE 1

Level of Contaminants and Impurities in Highly Purified Hemoglobin Solution.

| Contaminants/Impurities | | |
|---|---|---|
| Mycoplasma | | Undetectable |
| Phospholipids | Phosphatidyl-ethanolamine | BLOD (LOD = 0.52 μg/mL) |
| | Phosphatidyl-serine | BLOD (LOD = 1.73 μg/mL) |
| | Sphingomyelin | BLOD (LOD = 0.42 μg/mL) |
| | Total Phospholipid | <9.2 nmol/mL |
| Endotoxin | | <0.1 EU/mL |
| Residual Bovine DNA | | <0.025 pg/μl |
| Protein Impurities | Bovine Immunoglobulin G | 0.17 ppm |
| | Bovine Serum Albumin | <0.02 ppm |
| | Bovine Plasma Proteins | 0.02 ppm |
| | Bovine Carbonic Anhydrase | 36.04 ppm |

LOD: Limit of Detection;
BLOD: Below Limit of Detection

LOD: Limit of Detection; BLOD: Below Limit of Detection

Example 3: Preparation of Fumaryl-Crosslinked Tetrameric Hemoglobin

The crosslinking reaction was carried out under deoxygenated conditions, that is, less than 0.1 mg/L dissolved oxygen level in 0.9% w/v aqueous NaCl solution. DBSF was added to the highly purified bovine hemoglobin solution to form fumaryl-crosslinked hemoglobin. This stabilization procedure stabilizes the tetrameric form of hemoglobin (~65 kDa), which prevents the dissociation into dimeric forms, which are excreted through the kidneys. The stabilization of the tetrameric hemoglobin was carried out through a reaction of highly purified hemoglobin (tHb=13-15 g/dL) with 2.5 molar equivalents of DBSF at pH 9.0 for a period of 4 hours at 10-30° C. under an inert atmosphere of nitrogen (dissolved oxygen level maintained at less than 0.1 mg/L) to prevent oxidation of the hemoglobin to form ferric methemoglobin, which is physiologically inactive. During the reaction, the reaction pH was maintained by the addition of deoxygenated 0.1-0.5 M NaOH solution. The reaction mixture was then purified through tangential flow filtration using 30 kDa nominal molecular weight cut off (NMWCO) membrane. In the purification process, the concentration of the hemoglobin solution was maintained at 9.5-10.5 g/dL through a continuous feeding of acetate buffer (99 mM NaCl, 46 mM sodium acetate) into the reaction tank. The purification was completed after undergoing 10-16 diafiltration volume. The purity of the fumaryl-crosslinked tetrameric hemoglobin obtained was determined by size exclusion chromatography (SEC).

Example 4: Determination of Hemoglobin Stabilization Using Size Exclusion Chromatography A UPLC system (ACQUITY UPLC H-class System) equipped with a PDA detector and a size exclusion column (ACQUITY UPLC Protein BEH SEC column, 200A, 1.7 um, 4.6 mm×300 mm) was equilibrated with Tris-MgCl$_2$ Buffer (50 mM Tris, 750 mM MgCl$_2$ and 0.116 mM EDTA-Na$_2$, pH 6.5) at flow rate of 0.25 mL/min for 400 minutes.

Figure 3:
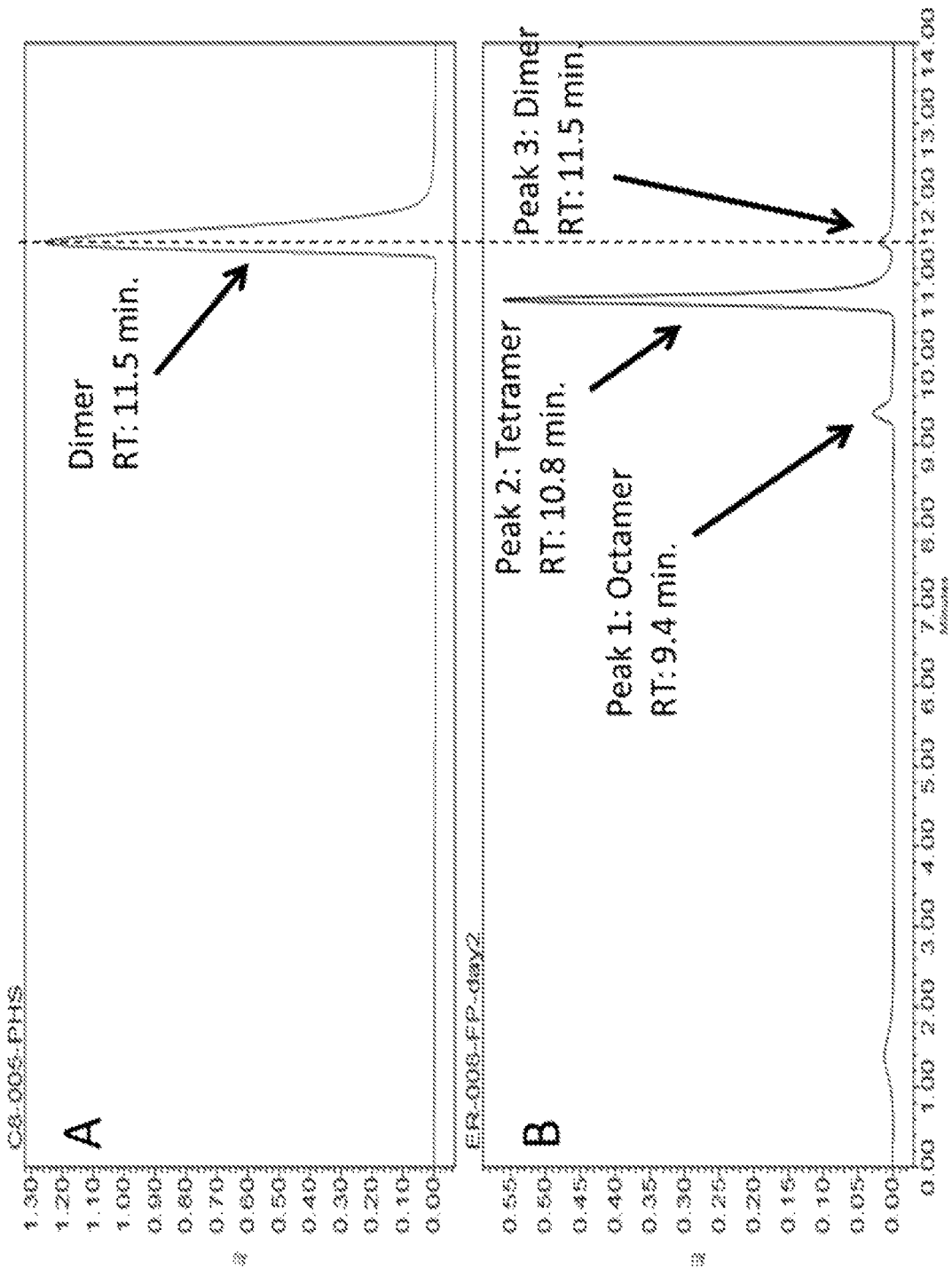
FIG. 3 depicts the size exclusion chromatogram for (A) non-crosslinked bovine hemoglobin and (B) fumaryl-crosslinked hemoglobin by DBSF reaction.
Figure 4:
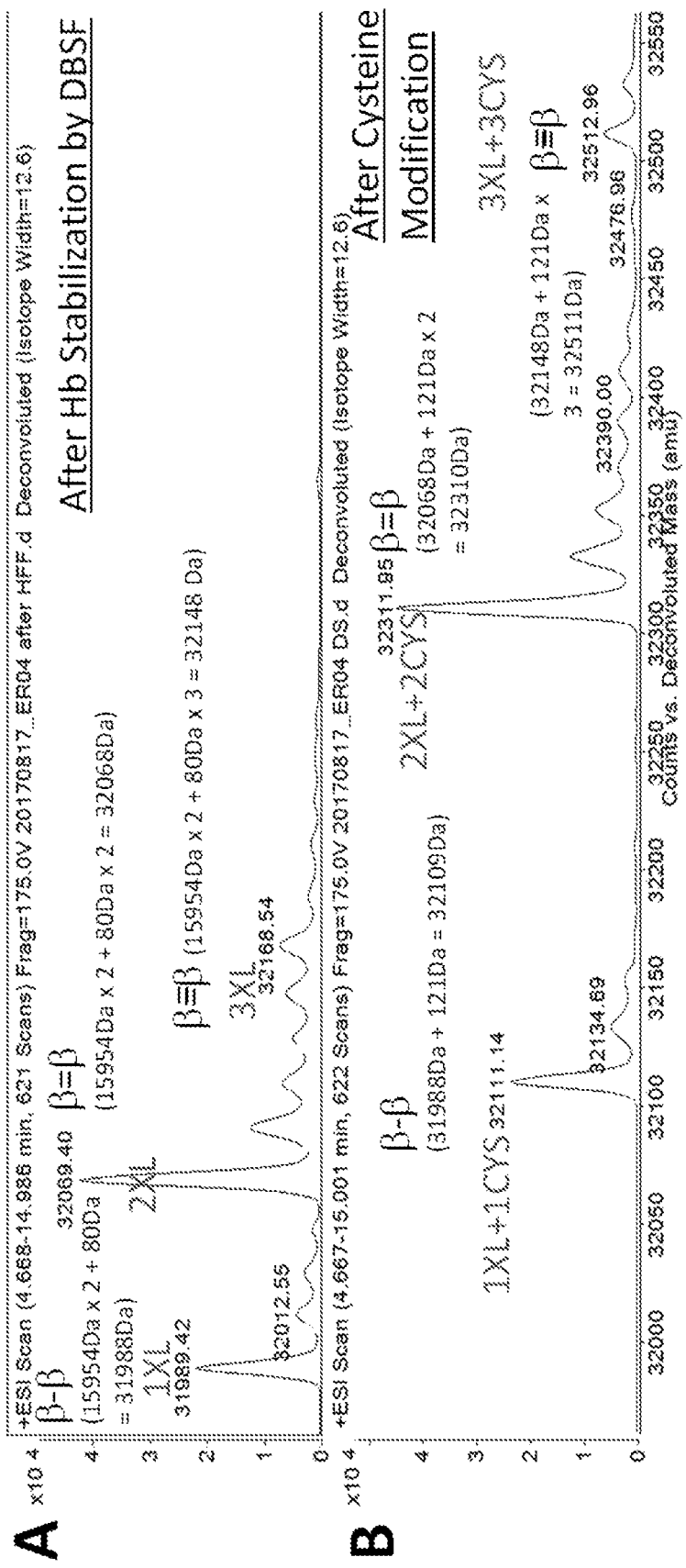
FIG. 4 depicts deconvoluted ESI-MS spectrum of (A) fumaryl-crosslinked hemoglobin by DBSF reaction and (B) cysteinyl-succinyl crosslinked hemoglobin.

Sample (3 mg/mL) was freshly prepared with water and analyzed by SEC with the detection wavelength set as 280 nm. Under this column condition, all the non-crosslinked bovine hemoglobin dissociated into dimeric forms, as depicted in FIG. 3A, while the crosslinked hemoglobin showed as tetramer with minor amounts of octamer, as depicted in FIG. 3B. From the SEC chromatogram, the elution peaks observed in the retention time of 9.4, 10.8 and 11.5 min are the protein signals of the octameric, tetrameric and dimeric form of hemoglobin, respectively. The percentage of different forms of hemoglobin was quantified by the integrated intensity of the corresponding peaks. Upon completion of the crosslinking reaction, the reaction mixture can contain at least 85% by weight of crosslinked tetrameric bovine hemoglobin (65 kDa), less than 10% by weight crosslinked octameric hemoglobin, and less than 5% by weight dimeric hemoglobin, as shown in FIG. 3B. The tetrameric structure of the bovine fumaryl-crosslinked hemoglobin molecule contained at least 1 to 3 crosslinker(s) between the beta globin chains (β-β crosslink), as shown in FIG. 4A.

Example 5 Modification of β-β Crosslink by Thiol-Containing Reagents

Selective modification of the fumaryl moieties of the crosslinker(s) in the fumaryl-crosslinked hemoglobin was achieved using thiol-containing molecules, such as cysteine, homocysteine, NAC and 2-mercaptoethanol (BME). Advantageously, the cysteine residues at position 92 of beta globin chain did not react with the fumaryl moieties.

Example 5A: Modification of β-β Crosslink by Cysteine

In this embodiment, the fumaryl moieties of the crosslinker between the beta chains were modified by cysteine. In the modification step, 40-80 mM cysteine at pH 8.0-8.3 was incubated with fumaryl-crosslinked hemoglobin (tHb=7-10 g/dL) in acetate buffer (99 mM NaCl, 46 mM sodium acetate, pH 8.2-8.4) for a period of 15-30 hours at 10-30° C. under deoxygenated condition for which the dissolved oxygen (DO) levels maintained below 0.1 mg/L. The residual cysteine/cystine in the reaction mixture was removed by a filtration step using a 30 kDa NMWCO membrane for which the reaction mixture went through 10-16 diafiltration volume (DV) with acetate buffer to bring the cysteine/cystine levels below 0.03% (w/w), as shown in Table 2. Apart from the cysteine/cystine levels, the levels of the DBSF and its hydrolyzed derivative (DBSA) in the cysteinyl-succinyl crosslinked hemoglobin were also below 0.03% (w/w).

TABLE 2

Level of Cysteine and Cystine in Cysteinyl-succinyl Crosslinked Bovine Hemoglobin after Filtration Step.

| Batch Number | Cysteine % (w/w) | Cystine % (w/w) |
| --- | --- | --- |
| C8002 | <0.0289 (BLOQ) | <0.0289 (BLOQ) |
| C8003 | <0.0289 (BLOQ) | <0.0289 (BLOQ) |
| C8005 | <0.0289 (BLOQ) | <0.0289 (BLOQ) |

BLOQ: Below Limits of Quantification

BLOQ: Below Limits of Quantification

The completion of the cysteine modification on the fumaryl-crosslinked hemoglobin was evaluated by ESI-MS analysis. A UPLC system (Agilent 6460) equipped with an electrospray ionization triple quadrupole mass spectrometer and a C3 column (Agilent, Poroshell 300SB-C3, 5 μm, 1.0 mm×75 mm) was equilibrated with acetonitrile with 0.1% formic acid at a flow rate of 0.2 mL/min for 30 minutes. Samples (0.3 mg/mL) were freshly prepared with water and analyzed by ESI-MS system using positive ion mode. The ESI-MS mass spectra of the samples were obtained by the deconvolution of the corresponding TIC chromatogram. A 1:1 stoichiometric addition of the cysteine to the β-β crosslinked globin chains was found at saturation, as depicted in FIG. 4B. As shown in FIG. 4A, the stabilization of hemoglobin via crosslinking between the β globin chains by DBSF resulted in 3 major species containing 1, 2, and 3 crosslink bridges and having the molecular weight of around 31988 Da, 32068 Da and 32148 Da, respectively. A cysteine amino acid (121 Da) was covalently bonded to the fumaryl moieties of these β-β crosslinked globin chains, resulting in species of 32,109 Da, 32,310 Da and 32,511 Da, respectively, as shown in FIG. 4B.

Figure 5:
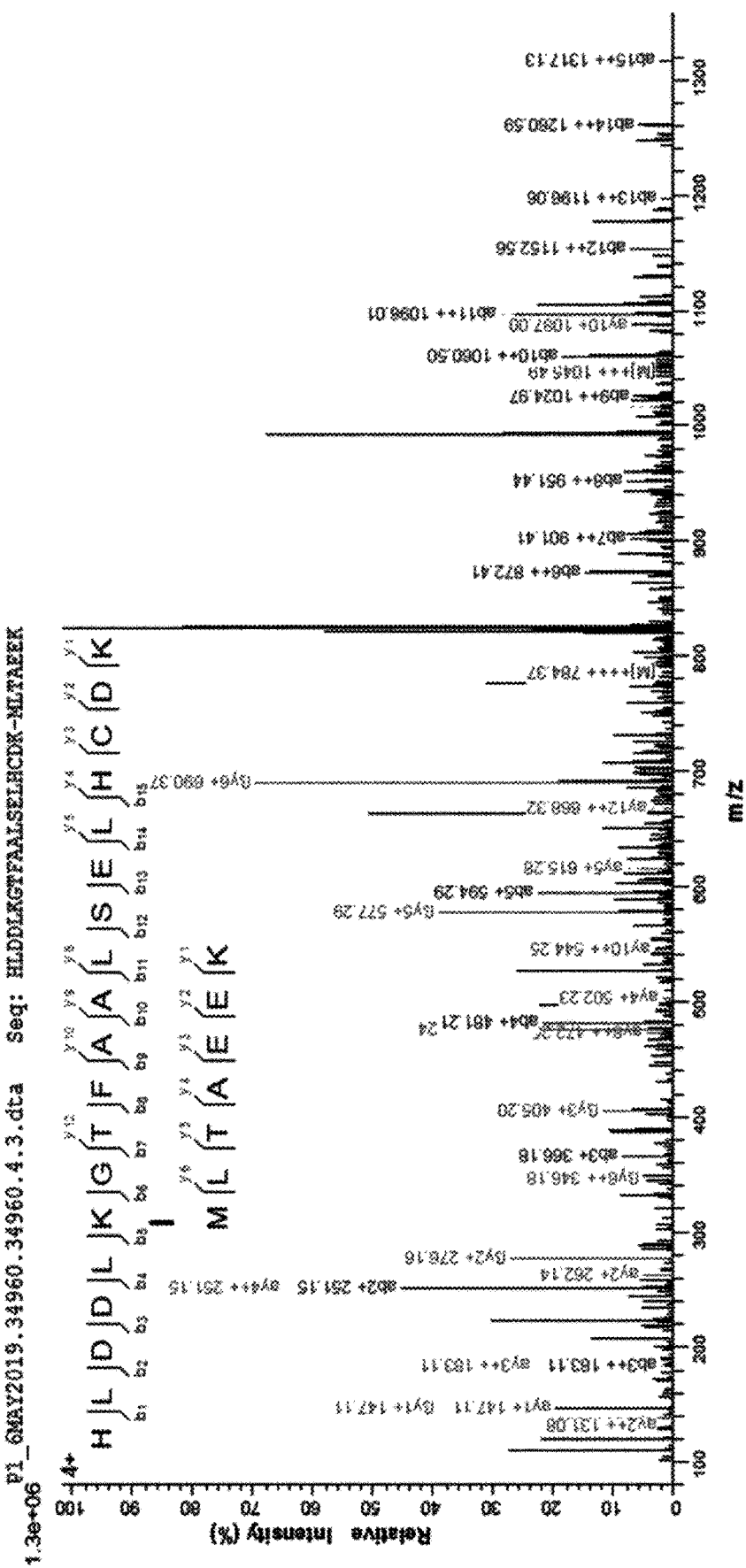
FIG. 5 depicts a table and an ESI-MS/MS spectrum of the cysteinyl-succinyl peptide which includes fragments: HLDDLKGTFAALSELHCDK-MLTAEEK (SEQ ID NO:1), HLDDLK-MLTAEEK (SEQ ID NO:2), HLDDLKG-MLTAEEK (SEQ ID NO:3), HLDDLK-MLTAEEKGT (SEQ ID NO:4), HLDDLKGTF-MLTAEEK (SEQ ID NO:5), HLDDLKGTFA-MLTAEEKGTFA (SEQ ID NO:6), HLDDLKGTFAA-MLTAEEK (SEQ ID NO:7), and HLDDLKGTFAAL-MLTAEEK (SEQ ID NO:8), demonstrating confirmation of cysteine modification on the double bond of fumaryl group in cysteinyl-succinyl crosslinked hemoglobin.

The sample was further analyzed by ESI-MS/MS analysis, in order to confirm the fumaryl moiety of the β-β crosslink of the fumaryl-crosslinked hemoglobin was modified by the cysteine amino acid. Sample was analyzed by 10% SDS-PAGE and visualized using 0.1% Coomassie Brilliant Blue R-250, 20% (v/v) methanol and 10% (v/v) acetic acid. The protein band corresponding to the major crosslinked globin chain with ~32 kDa was excised from the SDS-PAGE gel, cut into cubes (1×1 mm), and destained with 50% acetonitrile/20% 50 mM ammonium bicarbonate solution. The destained gel cubes were in-gel digested with 10 ng/μL sequencing grade trypsin in 50 mM ammonium bicarbonate at 37° C. overnight. After trypsin digestion, the trypsin-digested peptides were extracted by diffusion into 50% (v/v) acetonitrile and 1% (v/v) trifluoroacetic acid. The supernatant was collected and the solvent was removed by SpeedVac at 45° C. The trypsin-digested peptides were dissolved in 0.1% (v/v) formic acid, separated by reverse phase C18 column and analyzed using Orbitrap-Velos Mass Spectrometer. The EIS-MS/MS data was input into the pLink search engine for the crosslink sites analysis. As shown in FIG. 5, a peptide crosslinked at the N-terminal nitrogen at position 1 and the lysine side chain nitrogen at position 81 of β globin chains was identified. Importantly, the molecular weight of the crosslink peptide was 201 Da instead of 80 Da (fumaryl moiety), confirming that the cysteine amino acid (MW=121 Da) was covalently conjugated into the fumaryl moiety of the β-β crosslink peptide, but not the thiol group of cysteine at position 92 of beta globin.

A novel hemoglobin analog comprising cysteinyl-succinylated crosslinker(s) was produced by the above process. The pharmaceutical composition containing cysteinyl-succinyl crosslinked hemoglobin produced was kept under nitrogen with the presence of 0.2% (w/w) NAC with the following product characteristics: tHb=9.5-10.5 g/dL, pH 7.4-8.4, O$_2$Hb ≤0.10%, MetHb ≤5%, endotoxin ≤0.25 EU/mL and cysteinyl-succinyl crosslinked hemoglobin in range of 90-100%.

Example 5B: Comparison of Modification of β-β Crosslink by Thiol-Containing Reagents When reacting the fumaryl moieties with other thiol-containing reagents such as cysteine, homocysteine and 2-mercaptoethanol, at pH 8.2, different extents of modification between the fumaryl moieties and the thiol reagents were observed. Preliminary studies of thiol-containing reagents were selected based on the steric and electronic effects (pKa$_{SH}$ value), which includes, but is not limited to cysteine, β-mercaptoethanol and homocysteine.

Figure 6:
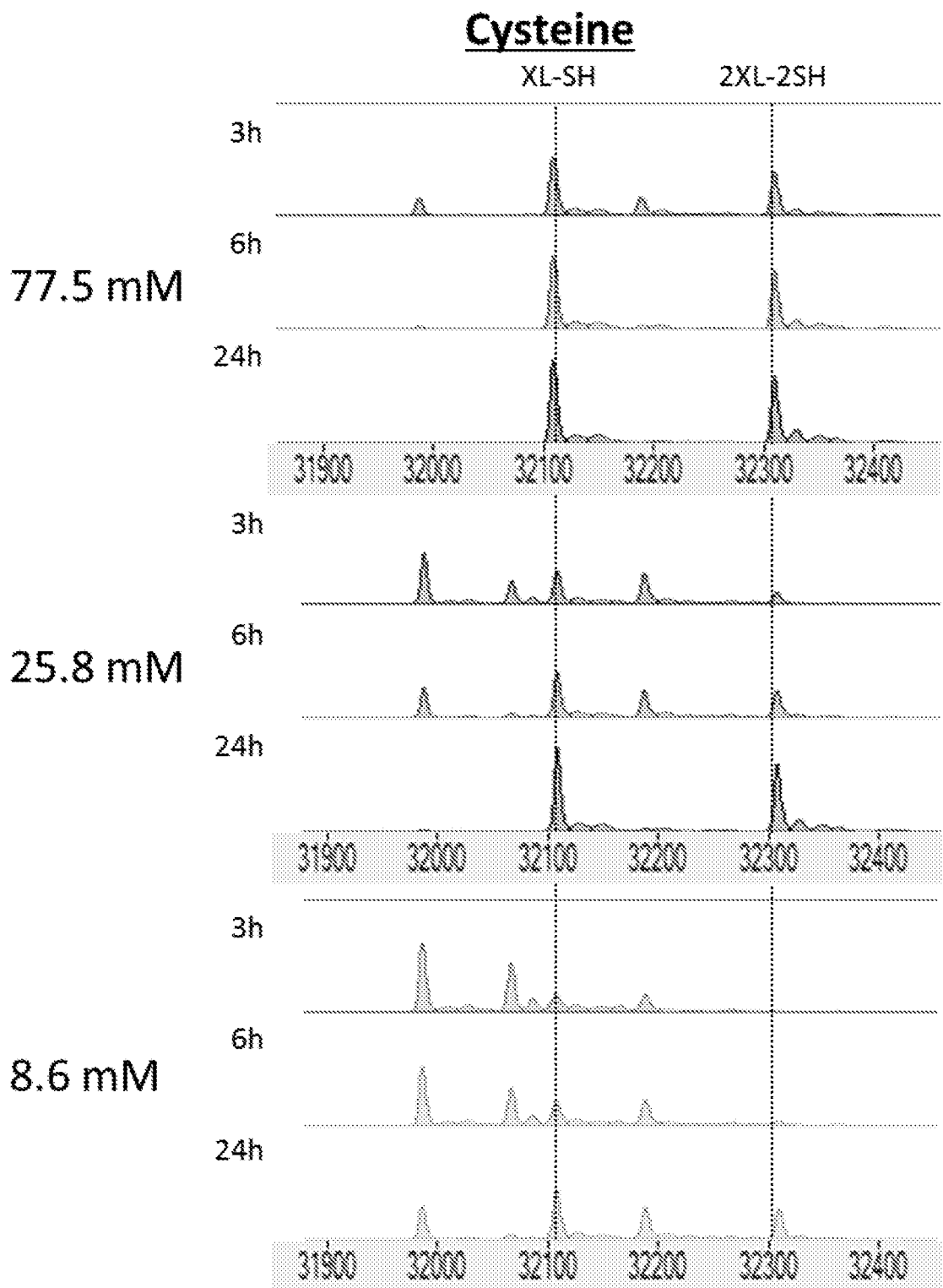
FIG. 6 depicts deconvoluted ESI-MS spectra of the reactivity of the double bond of fumaryl group towards different thiol-containing reagents (cysteine, β-mercaptoethanol and homocysteine).
Figure 6:
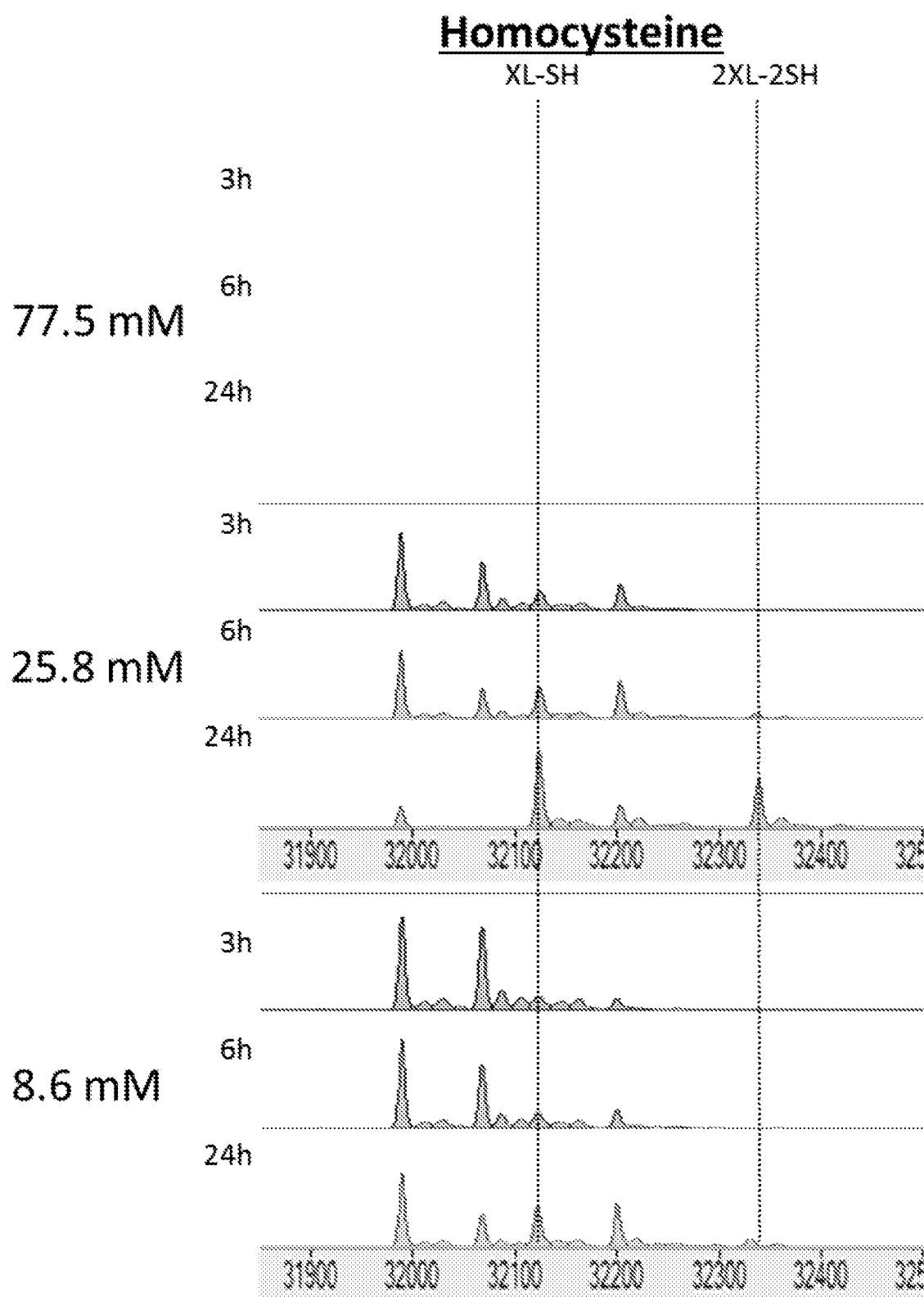
Figure 6:
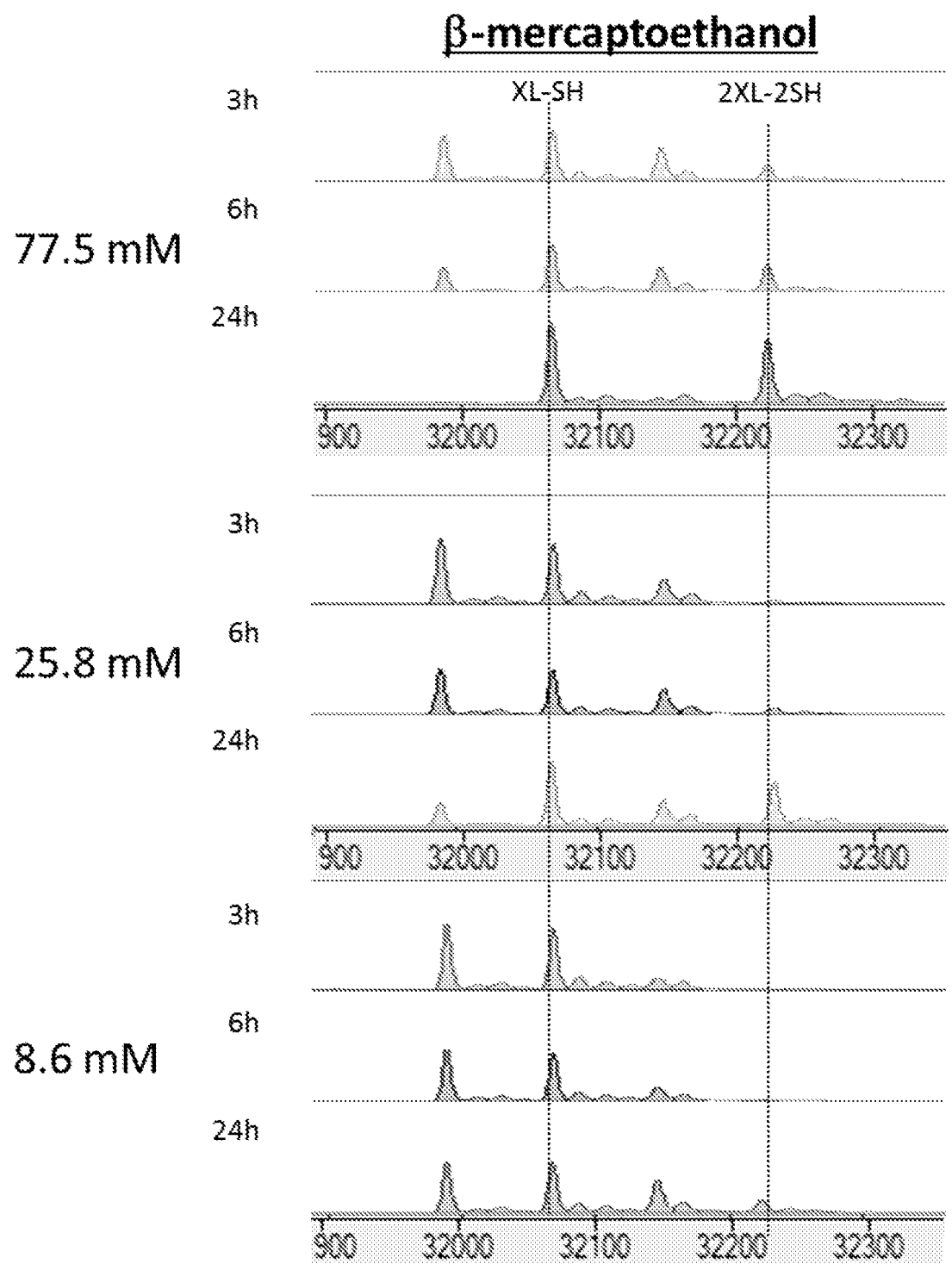

Degassed thiol reagents including cysteine (pKa$_{SH}$=8.35), β-mercaptoethanol (pKa$_{SH}$=8.87), and homocysteine (pKa$_{SH}$=9.6) at different concentrations (111 μL; 1000, 775, 258 and 86 mM in RA⁻ buffer, pH=8.2) was added to 1 mL of deoxygenated fumaryl-crosslinked hemoglobin solution (9.0 g/dL, pH=8.2) (Pitman, I. H. & Morris, I. J., 1979, Aust J Chem, 32: 1567-73). At 3, 6 and 24 hour, samples were collected and excess thiol was removed using desalting column (150 μL to Bio-Spin P6; 2 times). The samples were analyzed using ESI-MS, as depicted in FIG. 6 and the results are summarized in Table 3.

TABLE 3

Reactivity of Fumaryl-crosslinked Hemoglobin with Different Thiols.

| | | Thiol-containing Reagent | | | | | | | | |
|---|---|---|---|---|---|---|---|---|---|---|
| | | Cysteine (mM) | | | β-mercaptoethanol (mM) | | | | Homocysteine (mM) | | |
| Concentration (mM) | | 8.6 | 25.8 | 77.5 | 8.6 | 25.8 | 77.5 | 100 | 8.6 | 25.8 | 77.5 |
| Reaction Time | 3 hr | x | x | x | x | x | x | x | x | x | x |
| | 6 hr | x | x | x | x | x | x | x | x | x | x |
| | 24 hr | x | x | ✓ | x | x | x | ✓ | x | x | x | x: Incomplete saturation of fumaryl-thiol coupling reaction
✓: Saturation of fumaryl-thiol coupling reaction x: Incomplete saturation of fumaryl-thiol coupling reaction
✓: Saturation of fumaryl-thiol coupling reaction The extent of fumaryl-thiol reaction between the fumaryl-crosslinked hemoglobin and the thiols progressed in a time and concentration dependent manner. Unmodified fumaryl-crosslinked hemoglobin remained detectable after 3 and 6 hour incubation with thiols at different concentrations. At 24 hour, the reaction with 77.5 mM cysteine and 100 mM β-mercaptoethanol completely modified all the fumaryl moieties of the β-β crosslinks in the fumaryl crosslinked-hemoglobin, while unmodified fumaryl-crosslinked β-β globin chains remained detectable in the hemoglobin mixture for those incubated with lower concentration of cysteine, β-mercaptoethanol and homocysteine.

These results indicated that the fumaryl moieties of the β-β crosslinks underwent highly efficient Michael addition (1,4-addition) reactions with thiols. Reaction conditions such as pH, salt concentration, equivalents of the thiols and duration of the reaction were optimized resulting in achieving a 90-100% conversion of the fumaryl-crosslinked hemoglobin to the desired thiosuccinyl-crosslinked hemoglobin.

Figure 7:
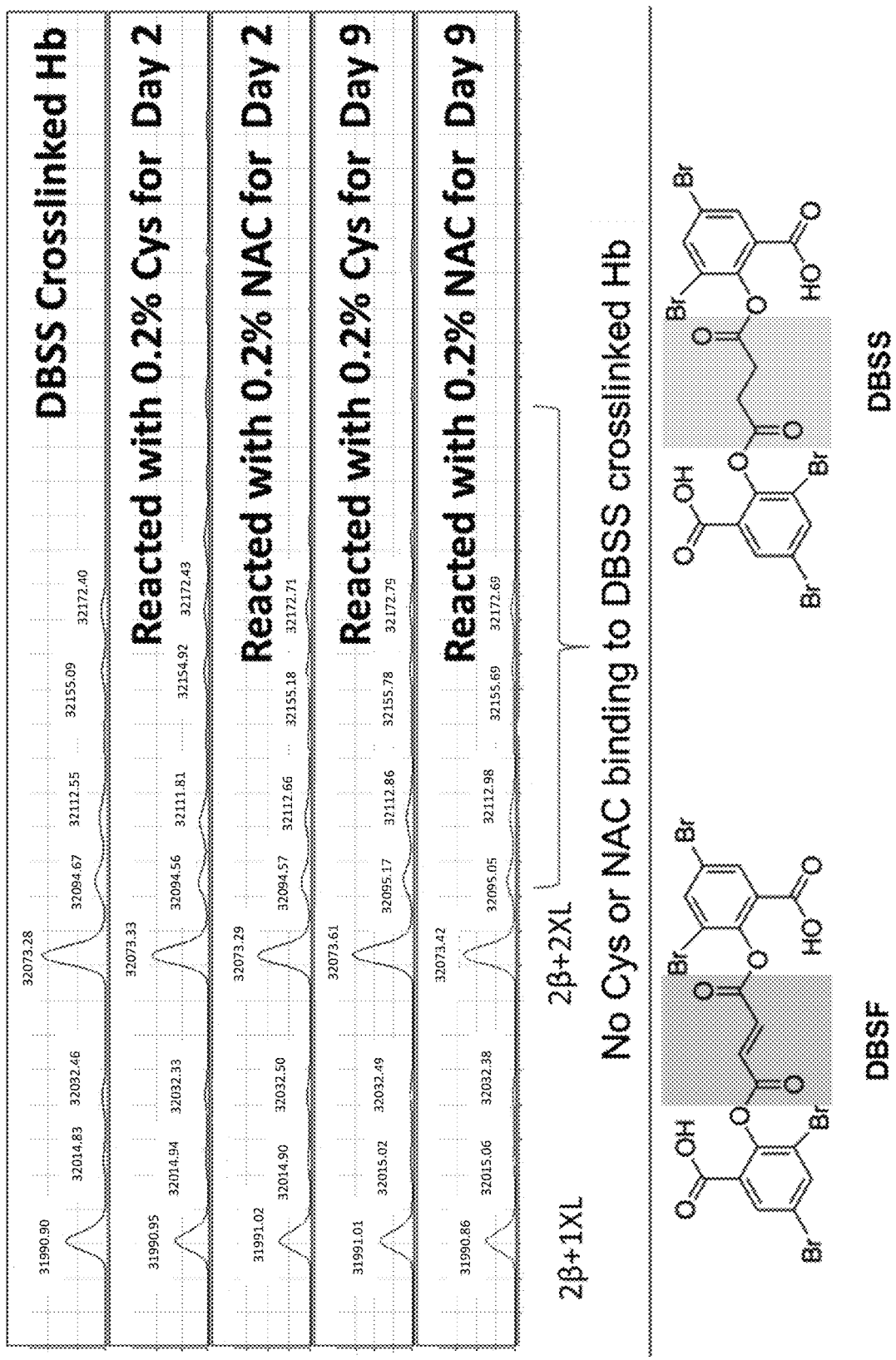
FIG. 7 depicts deconvoluted ESI-MS spectra of the reactivity of a hemoglobin crosslinked with bis-3,5-dibromosalicyl succinate (DBSS) towards cysteine and N-acetyl cysteine (NAC) at Day 2 and 9.

It is noteworthy that such modification between the cross-linker of the crosslinked hemoglobin and thiols, such as cysteine or NAC, did not occur with hemoglobin that was crosslinked with bis-3,5-dibromosalicyl succinate (DBSS), as depicted in FIG. 7, as expected.

Figure 8:
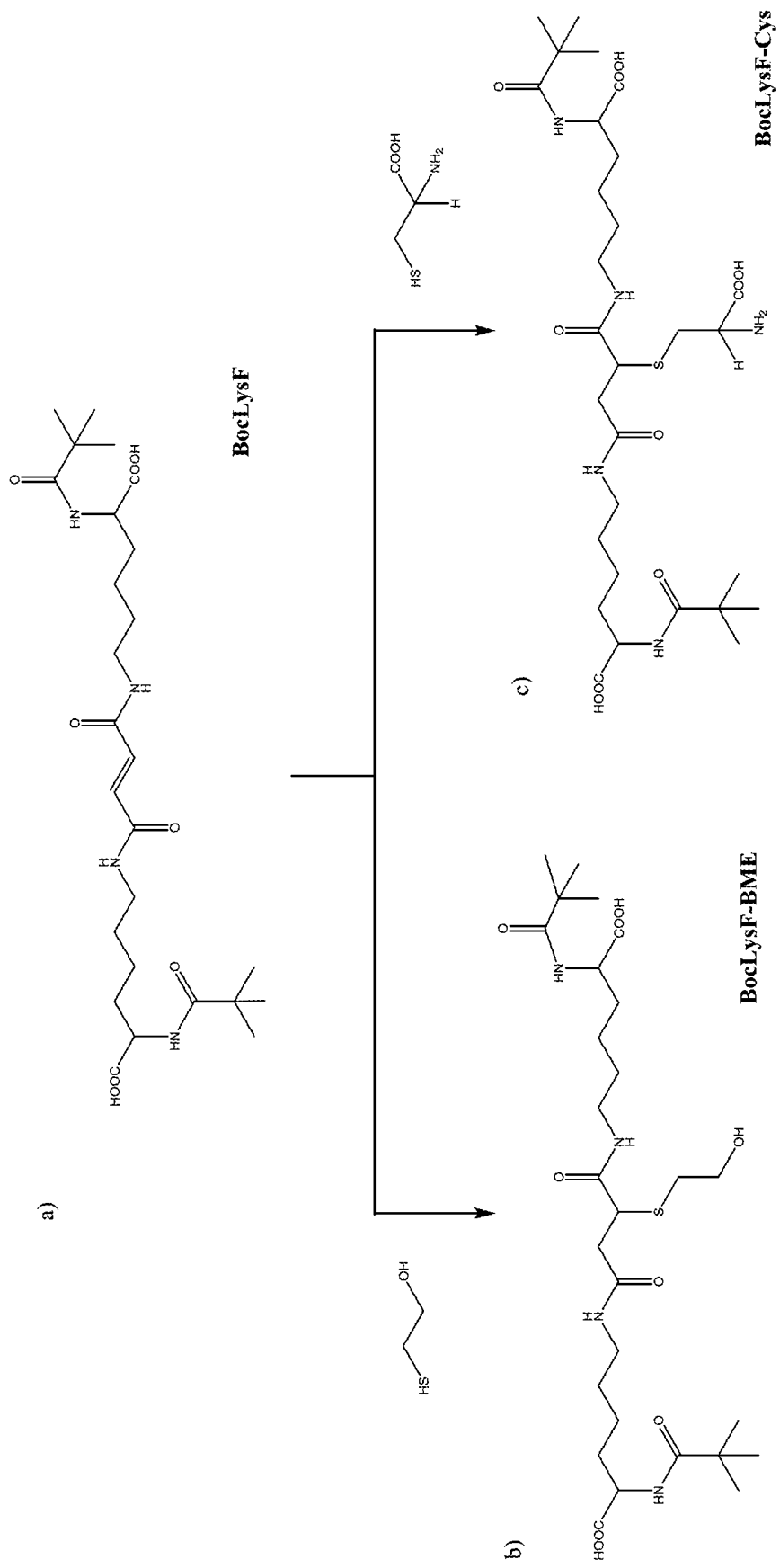
FIG. 8 represents conversion scheme of fumaramide (a) BocLysF with β-mercaptoethanol to give the alkylthiosuccinamide, (b) BocLysF-BME and with cysteine to give the alkylthiosuccinamide (c) BocLysF-Cys.

Example 6: Reaction Studies of Fumaramide with Alkylthiols Under Aqueous Condition The confirmation of the reaction between fumaramide with alkylthiol under aqueous condition was carried out using the model molecule N,N'-bis(1-((tert-butoxycarbonyl)amino)-1-(carboxy)pentyl)fumaramide (BocLysF; FIG. 8a). Upon reaction of BocLysF (15 mM) with model alkylthiols (77.5 mM) including β-mercaptoethanol and cysteine under aqueous conditions (0.1 M phosphate buffer, pH=8.2, deoxygenated) for 7 days, the MS spectra of reaction mixture clearly showed the complete consumption of starting material BocLysF and the appearance of expected mass peaks of thiol-addition products (M+H⁺; 649 and 692 Da, respectively). As shown from the NMR analysis of the reaction mixture, the loss of fumaramide double bond signal, formation of succinamide with geminal proton coupling peaks on C2 carbon and the splitting of amine signal were found. These observations can be rationalized by the occurrence of an addition reaction between fumaramide and alkylthiol through thiol-Michael-addition pathway that a pair of geminal protons was introduced to the C2 carbon of the resulting succinamide. Importantly, the reaction mixture was clean and the expected succinamide and residual alkylthiols were observed in NMR spectra, suggesting the reaction of the fumaryl and alkylthiol was complete. Thus, it is an ideal reaction for the post-crosslink modification and functionalization of fumaryl-crosslinked proteins including hemoglobin. Full characterization data of fumaramide BocLysF and the resulting succinamide including N,N'-bis(1-((tert-butoxycarbonyl)amino)-1-(carboxy)pentyl)-1-(2-hydroxyethylthio)-succinamide (BocLysF-BME; FIG. 8b) and N,N'-bis(1-((tert-butoxycarbonyl)amino)-1-(carboxy)pentyl)-1-(S-cysteinyl)succinamide (BocLysF-Cys; FIG. 8c) is shown in Table 4-6.

TABLE 4

The Complete Assignment of ¹H and ¹³C Signals of BocLysF in d6-DMSO.

| | ¹H [ppm] | ¹³C [ppm] |
|---|---|---|
| CH(COOH)(NHCOOC(C$\underline{H}_3$)$_3$) | 1.36 | 28.70 |
| C$\underline{H}$(COOH)(NHCOOC(CH$_3$)$_3$) | 3.74 | 54.47 |
| CH(COOH)(N$\underline{H}$COOC(CH$_3$)$_3$) | 6.66 | — |
| C$\underline{H}_2$CH$_2$CH$_2$CH$_2$NH | 1.58 | 31.30 |
| CH$_2$C$\underline{H}_2$CH$_2$CH$_2$NH | 1.27 | 23.40 |
| CH$_2$CH$_2$C$\underline{H}_2$CH$_2$NH | 1.39 | 29.13 |
| CH$_2$CH$_2$CH$_2$C$\underline{H}_2$NH | 3.10 | 38.91 |
| CH$_2$CH$_2$CH$_2$CH$_2$N$\underline{H}$ | 8.39 | — |
| C$\underline{H}$=C$\underline{H}$ | 6.77 | 133.47 |

TABLE 5

The Complete Assignment of ¹H and ¹³C Signals of BocLysF-BME in d6-DMSO.

| | ¹H [ppm] | ¹³C [ppm] |
|---|---|---|
| CHC$\underline{H}_2$CH$_2$CH$_2$CH$_2$NH | 1.55 | 32.86 |
| CHCH$_2$C$\underline{H}_2$CH$_2$CH$_2$NH | 1.21 | 22.62 |

TABLE 5-continued

The Complete Assignment of $^1$H and $^{13}$C Signals of BocLysF-BME in d6-DMSO.

| | $^1$H [ppm] | $^{13}$C [ppm] |
|---|---|---|
| CHCH$_2$CH$_2$CH$_2$CH$_2$NH | 1.34 | 20.96 |
| CHCH$_2$CH$_2$CH$_2$CH$_2$NH | 2.96 | 39.35 |
| CHCH$_2$CH$_2$CH$_2$CH$_2$NH | 7.88, 8.04 | — |
| CH(NHCOOC(CH$_3$)$_3$)(COOH)] | 1.36 | 28.69 |
| CH(NHCOOC(CH$_3$)$_3$)(COOH)] | 3.69 | 59.87 |
| CH(NHCOOC(CH$_3$)$_3$)(COOH)] | 6.17 | — |
| CO—CH$_2$CH—CO<br>\|<br>SCH$_2$CH$_2$OH | 2.31, 2.56 | 38.99 |
| CO—CH$_2$CH—CO<br>\|<br>SCH$_2$CH$_2$OH | 3.60 | 43.57 |
| CO—CH$_2$CH—CO<br>\|<br>SCH$_2$CH$_2$OH | 2.61 | 34.56 |
| CO—CH$_2$CH—CO<br>\|<br>SCH$_2$CH$_2$OH | 3.48 | 61.15 |

TABLE 6

The Complete Assignment of $^1$H and $^{13}$C Signals of BocLysF-Cys in d6-DMSO.

| | $^1$H [ppm] | $^{13}$C [ppm] |
|---|---|---|
| CHCH$_2$CH$_2$CH$_2$CH$_2$NH | 1.55 | 33.41 |
| CHCH$_2$CH$_2$CH$_2$CH$_2$NH | 1.20 | 22.26 |
| CHCH$_2$CH$_2$CH$_2$CH$_2$NH | 1.35 | 29.31 |
| CHCH$_2$CH$_2$CH$_2$CH$_2$NH | 2.90, 3.13 | 39.98 |
| CHCH$_2$CH$_2$CH$_2$CH$_2$NH | 8.16, 8.43 | — |
| CH(NHCOOC(CH$_3$)$_3$)(COOH)] | 3.63 | 56.22 |
| CH(NHCOOC(CH$_3$)$_3$)(COOH)] | 1.34 | 28.55 |
| CH(NHCOOC(CH$_3$)$_3$)(COOH)] | 6.05 | — |
| CO—CH$_2$CH—CO<br>\|<br>SCH$_2$CH(NH$_2$)(COOH) | 2.38, 2.52 | 37.90 |
| CO—CH$_2$CH—CO<br>\|<br>SCH$_2$CH(NH$_2$)(COOH) | 3.71 | 42.87 |
| CO—CH$_2$CH—CO<br>\|<br>SCH$_2$CH(NH$_2$)(COOH) | 2.75, 2.94, 3.06 | 34.26 |

TABLE 6-continued

The Complete Assignment of $^1$H and $^{13}$C Signals of BocLysF-Cys in d6-DMSO.

| | $^1$H [ppm] | $^{13}$C [ppm] |
|---|---|---|
| CO—CH$_2$CH—CO<br>\|<br>SCH$_2$CH(NH$_2$)(COOH) | 3.46 | 55.37 |

Example 7: Purity of Cysteinyl-Succinyl Crosslinked Hemoglobin in Pharmaceutical Composition As described in Example 5, pharmaceutical composition containing cysteinyl-succinyl crosslinked hemoglobin was produced by the reaction of cysteine with the fumaryl moieties of the β-β crosslinks of the fumaryl-crosslinked hemoglobin.

The purity of the cysteinyl-succinyl crosslinked hemoglobin produced by the above embodiments was evaluated by ESI-MS analysis. Samples were analyzed by LC-MS on an Agilent 6540 Electrospray Ionization Quadrupole-Time-of-Flight spectrometer connected to an liquid chromatography system (Agilent 6460) with a C3 column (Agilent Poroshell 300SB-C3, 5 μm, 1.0 mm×75 mm) and the mass spectra were deconvoluted using the Maximum Entropy algorithm in the Agilent MassHunter Qualitative Analysis software. Crosslinked species were identified by matching the molecular masses from the deconvoluted MS data to theoretical figures. Relative abundances of molecular species were estimated using the area-under-curve of the deconvoluted spectra.

Based on the analysis of ESI-MS spectrum, the fumaryl-crosslinked hemoglobin were found to contain one (1XL), two (2XL) or three (3XL) fumaryl crosslinks present in a molar ratio of 28%, 58% and 15%, respectively, in which at least 1 fumaryl bridge was crosslinked between β globin chains. Following the modification with cysteine stated, the peaks corresponding to the mass of unmodified fumaryl-crosslinked β-β globin chains were undetectable in the ESI-MS spectrum. Instead, it was found that the peaks were found to be present in similar proportion, but the molecular weights were shifted by 121, 242, and 363 Da, which corresponded to the stoichiometric addition of 1 (1XL+1Cys), 2 (2XL+2Cys) and 3 cysteine amino acids (3XL+3Cys), respectively. The molecular weights for the β-β crosslinks before and after cysteine modification were shown for each component. The findings supported the notion that the fumaryl thiol coupling reaction between the cysteine and fumaryl-crosslinked hemoglobin was totally complete and at least 95% or higher conversion was achieved after modification with cysteine under the tested reaction conditions, as depicted in Table 7.

TABLE 7

Proportion of Beta-Beta Globin Chain (β-β) in Fumaryl-crosslinked Hemoglobin Before and After Cysteine Modification.

| | Crosslink Species | Molecular Mass | % Hemoglobin with Different Numbers of Fumaryl Crosslinks | % Hemoglobin with Different Numbers of Cysteinyl-succinyl Crosslinks After Modification by Cysteine |
|---|---|---|---|---|
| Fumaryl Crosslink in β-β globin Chain | 1 Fumaryl Crosslink (XL) | 31988 Da | 28% | NA |
| | 2 Fumaryl Crosslinks (2XL) | 32068 Da | 58% | NA |
| | 3 Fumaryl Crosslinks (3XL) | 32148 Da | 15% | NA |

TABLE 7-continued

Proportion of Beta-Beta Globin Chain (β-β) in Fumaryl-crosslinked
Hemoglobin Before and After Cysteine Modification.

|  | Crosslink Species | Molecular Mass | % Hemoglobin with Different Numbers of Fumaryl Crosslinks | % Hemoglobin with Different Numbers of Cysteinyl-succinyl Crosslinks After Modification by Cysteine |
|---|---|---|---|---|
| Cysteinyl-succinyl Crosslink in β-β Globin Chain | 1 Cysteinyl-succinyl Crosslinker (1XL + 1Cys) | 32109 Da | 0% | 31% |
|  | 2 Cysteinyl-succinyl Crosslinkers (2XL + 2Cys) | 32310 Da | 0% | 59% |
|  | 3 Cysteinyl-succinyl Crosslinkers (3XL + 3Cys) | 32511 Da | 0% | 10% |

NA: Not Applicable

Example 8: Effects of pH and Reaction Medium on the Reaction Rate of the Fumaryl-Thiol Coupling Reaction The reaction rates of the fumaryl-thiol coupling reaction under other reaction parameters including pH and reaction medium were examined. A degassed solution of β-mercaptoethanol (111 µL; 775 mM in RA⁻ or RA⁻ with extra 0.9% NaCl) was added to 1 mL of deoxygenated fumaryl-crosslinked hemoglobin solution (8.7 g/dL, pH=7.4, 8.2, or 9.0; In RA⁻ or RA⁻ with extra 0.9% NaCl). At 6 and 24 hour, samples were collected and excess thiol was removed using a desalting column (150 µL to Bio-Spin P6; 2 times). The samples were analyzed using ESI-MS analysis and the results are shown in Table 8. Complete saturation of the fumaryl bridges was not detected in the samples collected at 6 hours. Among the reaction conditions at different pH values and salt concentrations, modification of the fumaryl bridges by ~77.5 mM β-mercaptoethanol was complete in 24 hours at pH 7.4 or pH 9.0. Although a complete modification was achieved with 77.5 mM cysteine at pH 8.2, the modification by 77.5 mM β-mercaptoethanol at pH 8.2 remained incomplete and the presence of the unmodified fumaryl bridges was detected even after 24 hours of incubation. The result also revealed that there was no observable effect on the reaction rate of the coupling reactions when the salinity of the reaction medium was increased.

TABLE 8

Effects of pH and Reaction Medium on the Reaction Rate
of the Fumaryl-thiol Coupling Reaction Between Fumaryl-
crosslinked Hemoglobin and β-mercaptoethanol.

|  |  | Reaction pH |  |  |
|---|---|---|---|---|
| Reaction Condition | Reaction Time | 7.4 | 8.2 | 9.0 |
| 77.5 mM β-mercaptoethanol in RA-* Buffer | 6 hr | x | x | x |
|  | 24 hr | ✓ | x | ✓□ |

TABLE 8-continued

Effects of pH and Reaction Medium on the Reaction Rate
of the Fumaryl-thiol Coupling Reaction Between Fumaryl-
crosslinked Hemoglobin and β-mercaptoethanol.

|  |  | Reaction pH |  |  |
|---|---|---|---|---|
| Reaction Condition | Reaction Time | 7.4 | 8.2 | 9.0 |
| 77.5 mM β-mercaptoethanol in RA-* Buffer with extra 0.9% NaCl | 6 hr | x | x | x |
|  | 24 hr | ✓ | x | ✓ | x: Incomplete saturation of fumaryl-thiol coupling reaction
✓: Saturation of fumaryl-thiol coupling reaction
*Ringer's Acetate Minus Buffer (RA− Buffer)

Example 9: Effects of Thiol-Containing Reagent Concentration and Reaction Time on the Reaction Rate of the Fumaryl-Thiol Coupling Reaction A degassed solution of β-mercaptoethanol (111 µL; 775, 388, 194, 97, and 48 mM in RA⁻, pH 9.0) or cysteine (111 µL; 775, 388, 194, and 97 mM in RA⁻, pH=9.0) was added to 1.0 mL of deoxygenated fumaryl-crosslinked hemoglobin solution (9.0 g/dL, pH=9.0). At 6, 24, 48, and 72 hour, samples were collected and excess thiol was removed using desalting column (150 µL to Bio-Spin P6; 2 times). All the samples were analyzed using ESI-MS and the results are summarized in Table 9. The fumaryl-thiol reaction rate increased in a concentration dependent manner while the coupling rate of cysteine and β-mercaptoethanol to the fumaryl moieties were doubled by increasing the concentration from 19.4 mM to 38.8 mM. Complete modification of the fumaryl moieties by either cysteine or β-mercaptoethanol was achieved within 24 hour. Although the reaction rate was substantially decreased in low thiol reagents concentration such as 9.7 mM, saturation of fumaryl bridges was achieved by extending the reaction time to 72 hour.

TABLE 9

Effects of Thiol Concentration and Reaction Time on the Reaction
Rate of the Fumaryl-thiol Coupling Reaction Between Fumaryl- crosslinked
Hemoglobin and Thiols (Cysteine and β-mercaptoethanol).

|  |  | Cysteine |  |  |  | β-mercaptoethanol |  |  |  |  |
|---|---|---|---|---|---|---|---|---|---|---|
| Concentration (mM) |  | 9.7 | 19.4 | 38.8 | 77.5 | 4.8 | 9.7 | 19.4 | 38.8 | 77.5 |
| Reaction Time | 6 hr | x | x | x | x | x | x | x | x | x |
|  | 24 hr | x | x | ✓ | ✓ | x | x | x | ✓ | ✓ |

TABLE 9-continued

Effects of Thiol Concentration and Reaction Time on the Reaction Rate of the Fumaryl-thiol Coupling Reaction Between Fumaryl- crosslinked Hemoglobin and Thiols (Cysteine and β-mercaptoethanol).

|  | Cysteine | | | | β-mercaptoethanol | | | | |
|---|---|---|---|---|---|---|---|---|---|
| Concentration (mM) | 9.7 | 19.4 | 38.8 | 77.5 | 4.8 | 9.7 | 19.4 | 38.8 | 77.5 |
| 48 hr | x | ✓ | ✓ | ✓ | x | x | ✓ | ✓ | ✓ |
| 72 hr | ✓ | ✓ | ✓ | ✓ | x | ✓ | ✓ | ✓ | ✓ | x: Complete saturation of fumaryl-thiol coupling reaction
✓: Saturation of fumaryl-thiol coupling reaction Complete modification of the fumaryl moieties may be limited by the physical-chemical properties of the thiol reagents and suboptimal coupling conditions. Since the reaction conditions leading to the saturation of the fumaryl moieties varies between different thiol reagents, the inherent molecular properties, such as the steric and electronic effects, and the reaction conditions, at least act in combination with the equivalents of the thiol reagents, reaction pH and duration, not only affect the rate of modification but also the overall conversion of the coupling reaction. For instance, 77.5, 174 and 310 mM N-acetyl cysteine (NAC) were incubated with fumaryl-crosslinked hemoglobin at pH 8.2, the samples collected at 24 and 48 hour were analyzed by ESI-MS. The results showed that the conversion of fumaryl-thiol coupling reaction was found to below 95% for all concentrations at 24 hour. The fumaryl-thiol coupling reaction at 95% was observed only when extending the incubation time to 48 hour using 310 mM NAC. When compared to the fumaryl-thiol reaction using cysteine, the concentration of NAC to saturate the fumaryl bridges were 4 times higher and the incubation time was doubled. These results suggest that higher NAC concentration and incubation time may be required to achieve >95% conversion of the fumaryl moieties of the crosslinked hemoglobin by NAC. These results suggest that unless a person having ordinary skill in the art was intentionally attempting to carry out the fumaryl-thiol coupling reaction and endeavored to optimize the reaction conditions to ensure complete reaction, the typical concentration of thiol reagents utilized as an excipient to reduce or inhibit the formation of methemoglobin would not result in the formation of thiosuccinyl-crosslinked hemoglobin at high levels of conversion (Table 10).

TABLE 10

Effects of NAC Concentration and Reaction Time on the Reaction Rate of the Fumaryl-thiol Coupling Reaction.

| | NAC Concentration | | |
|---|---|---|---|
| Reaction Time | 77.5 mM | 174 mM | 310 mM |
| 24 hours | x | X | X |
| 48 hours | x | x | ✓□ | x: Incomplete saturation of fumaryl-thiol coupling reaction
✓: Saturation of fumaryl-thiol coupling reaction Example 10: Change of p50 Value of Fumaryl-Crosslinked Hemoglobin after Modification of Thiol-Containing Reagents The oxygen affinity properties of hemoglobin can be described by its p50 value, determined from the oxygen dissociation curve. The oxygen dissociation curve of the hemoglobin shows the relationship between the hemoglobin saturation at different oxygen tensions, and the p50 is the oxygen tension at which hemoglobin is 50% saturated.

The p50 value of the thiosuccinyl-crosslinked hemoglobin produced by the complete reaction between fumaryl-crosslinked hemoglobin and different thiol-containing reagents was evaluated. The oxygen dissociation curve for the hemoglobin solution was obtained using a Hemox analyzer (TCS Scientific, New Hope, Pa.). Oxygen tension was measured with a Clark oxygen electrode, and the hemoglobin saturation was measured using a built-in dual wavelength spectrophotometer. The measurement was carried out in Hemox solution (135 mM NaCl, 5 mM KCl and 30 mM TES, pH 7.4) with a final hemoglobin concentration of 0.05 g/dL and the temperature maintains at 37° C. throughout the measurement. A computer-based analysis of oxygen dissociation curve was performed yielding p50 for oxygen binding. Oxygen dissociation parameters were derived by fitting the Adair equations to each oxygen dissociation curve by nonlinear least-squares procedure included in the Hemox analyzer software (TCS Hemox DAQ System, Version 2.0).

The results reveal that over 95% of fumaryl-crosslinked hemoglobin was converted to the thiosuccinyl-crosslinked hemoglobin by incubating fumaryl-crosslinked hemoglobin at 310 mM NAC for 48 hour and its p50 value increased by 11%. In contrast, a thiosuccinyl-crosslinked hemoglobin solution containing over 95% purity prepared by incubating with either 77.5 mM cysteine or 100 mM β-mercaptoethanol showed comparable p50 values, compared to the unmodified fumaryl-crosslinked hemoglobin, as shown in Table 11.

TABLE 11 p50 Values of Thiosuccinyl-crosslinked Hemoglobin After Modification with Different Thiol Reagents.

| Incubation Time | Fumaryl-crosslinked Hemoglobin | Thiosuccinyl-crosslinked Hemoglobin | | | | |
|---|---|---|---|---|---|---|
| | | N-acetyl Cysteine | | | β-mercaptoethanol | Cysteine |
| | — | 77.5 mM | 174 mM | 310 mM | 100 mM | 77.5 mM |
| 0 hr | 55 mmHg | — | — | — | — | — |
| 24 hr | — | 56 mmHg | 60 mmHg | 63 mmHg | 53 mmHg | 54 mmHg |
| 48 hr | — | 58 mmHg | 62 mmHg | 61 mmHg | — | — |

The results also reveal that a complete modification was achieved by conjugating the cysteine to thiol-blocked fumaryl-crosslinked hemoglobin (hemoglobin in which the position 92 cysteine residue of the beta globins is blocked (alkylated) by reaction with iodoacetamide prior to the crosslinking reaction with the fumaryl crosslinking agent) according to the preparation procedure as described in Example 5A. The p50 value of the cysteinyl-succinyl crosslinked thiol-blocked hemoglobin also remained unchanged after modification either for that having a p50 value of ~36 mmHg (crosslinked under deoxygenated condition) or ~9 mmHg (crosslinked under oxygenated condition), as shown in Table 12. This reveals that the conjugation of cysteine to the fumaryl-crosslinked hemoglobin having different oxygen carrying capacities surprisingly did not alter their p50 values.

TABLE 12 p50 Values of Cysteinyl-succinyl Crosslinked Hemoglobin Produced from Thiol-blocked Fumaryl-crosslinked Hemoglobin Either Crosslinked Under Deoxygenated or Oxygenated conditions.

| | Thiol-blocked Fumaryl-crosslinked Bovine Hemoglobin | Thiol-blocked Cysteinyl-succinyl Crosslinked Bovine Hemoglobin |
|---|---|---|
| Crosslink Reaction under Deoxygenated Condition | 37 mmHg | 35 mmHg |
| Crosslink Reaction under Oxygenated Condition | 9 mmHg | 9 mmHg |

Example 11: In-Vitro Stability of Cysteinyl-Succinyl Crosslinked Hemoglobin

The stability of the cysteinyl-succinylated moieties in the cysteinyl-succinyl crosslinked hemoglobin was tested in the presence of small molecule thiols such as cysteine, NAC, or glutathione (GSH). These small molecule thiols are commonly used in hemoglobin-based therapeutic drug formulations as excipients, e.g., to reduce the methemoglobin levels.

The fumaryl-crosslinked hemoglobin and cysteinyl-succinyl crosslinked hemoglobin were incubated with NAC, cysteine, or GSH at 1:4 or 1:8 molar ratios (100 mg/mL hemoglobin) under an apoxic environment. Samples taken at various time points were analyzed by ESI-MS on an Agilent 6540 Electrospray Ionization Quadrupole-Time-of-Flight spectrometer connected to a liquid chromatography system (Agilent 6460) with a C3 column (Agilent Poroshell 300SB-C3, 5 μm, 1.0 mm×75 mm). The mass spectra were deconvoluted using the Maximum Entropy algorithm in the Agilent MassHunter software. Crosslinked globin species were identified by matching the molecular masses from the deconvoluted MS data to theoretical figures. Relative abundances of molecular species were estimated using the area-under-curve of the deconvoluted spectra.

Table 13 shows the estimation of relative abundances of different crosslinked β-β species derived from ESI-MS data of cysteinyl-succinyl crosslinked hemoglobin over 12 months in the presence of NAC at an eight-fold molar excess. The area under curve (AUC) of the main crosslinked species remained stable after at least 12 months, showing the stability of the abundances of the crosslinked species over time.

TABLE 13

Stability of β-β Globin Chains in Cysteinyl-succinyl Crosslinked Hemoglobin in the Presence of NAC over 12 Months.

| | % Hemoglobin with Different Numbers of Cysteinyl-succinyl β-βCrosslinks | | |
|---|---|---|---|
| Time | 1XL + 1Cys | 2XL + 2Cys | 3XL + 3Cys |
| At Release | 32% | 58% | 10% |
| 1 Month | 39% | 51% | 11% |
| 2 Months | 36% | 53% | 11% |
| 5 Months | 40% | 53% | 6% |
| 7 Months | 42% | 51% | 7% |
| 10 Months | 39% | 55% | 7% |
| 11 Months | 35% | 57% | 8% |
| 12 Months | 37% | 56% | 7% |

Percentages are relative abundances of the different crosslinked species, as estimated from deconvoluted LC-MS spectra. "XL"—crosslink, "Cys"—cysteine.

In contrast, the fumaryl moieties of the fumaryl-crosslinked hemoglobin reacted continuously with NAC in a 9-week monitoring period, with the NAC covalently attached to the β-β crosslink of the hemoglobin molecule (Table 14). Similar reactions with cysteine and GSH were also evident (Table 15 &16).

TABLE 14

Stability of β-β Globin Chains in Fumaryl-crosslinked Hemoglobin in the Presence of 0.2% NAC over 9 Weeks.

| | % Hemoglobin with Different Species of β-β Crosslinks | | | | |
|---|---|---|---|---|---|
| Time | 1XL | 2XL | 1XL + 1NAC | 2XL + 1NAC | 2XL + 2NAC |
| Day 3 | 18% | 20% | 20% | 37% | 5% |
| 1 Week | 19% | 21% | 20% | 37% | 3% |
| 3 Weeks | 12% | 9% | 28% | 43% | 8% |

TABLE 14-continued

Stability of β-β Globin Chains in Fumaryl-crosslinked
Hemoglobin in the Presence of 0.2% NAC over 9 Weeks.

| | % Hemoglobin with Different Species of β-β Crosslinks | | | | |
|---|---|---|---|---|---|
| Time | 1XL | 2XL | 1XL + 1NAC | 2XL + 1NAC | 2XL + 2NAC |
| 5 Weeks | 9% | 3% | 32% | 44% | 11% |
| 9 Weeks | 3% | 0% | 38% | 41% | 19% |

Percentages are relative abundances of the different cross-linked species, as estimated from deconvoluted LC-MS spectra. XL"—crosslink, "NAC"—N-acetyl cysteine.

TABLE 15

Stability of β-β Globin Chains in Fumaryl-crosslinked Hemoglobin
with 4-fold Molar Excess of Cysteine over 4 Hours.

| | % Hemoglobin with Different Species of β-β Crosslinks | | | |
|---|---|---|---|---|
| Time | 1XL + 1Cys | 2XL | 2XL + 1Cys | 2XL + 2Cys |
| T = 0.25 Hour | 20% | 58% | 22% | 0% |
| T = 4 Hours | 22% | 24% | 34% | 20% |

TABLE 16

Stability of β-β Globin Chains in Fumaryl-crosslinked Hemoglobin
with 4-fold Molar Excess of Glutathione over 4 Hours.

| | % Hemoglobin with Different Species of β-β Crosslinks | | | |
|---|---|---|---|---|
| Time | 1XL | 1XL + 1GSH | 2XL | 2XL + 1GSH |
| T = 0.25 hour | 27% | 4% | 64% | 5% |
| T = 4 hours | 20% | 9% | 58% | 12% |

Percentages are relative abundances of the different cross-linked species, as estimated from deconvoluted LC-MS spectra. "XL"—crosslink, "GSH"—glutathione.

Example 12: Stability of NAC as Excipient in Cysteinyl-Succinyl Crosslinked Hemoglobin Solution Thiol-containing compounds are commonly used in hemoglobin-based oxygen therapeutics as excipients for conversion and prevention of dysfunctional methemoglobin. In this experiment, NAC was used as an excipient in cysteinyl-succinyl crosslinked hemoglobin solution, and NAC was oxidized to N,N'-diacetyl-L-cystine ($NAC_2$) when reduced the dysfunctional methemoglobin to functional hemoglobin form. Samples were taken at various time points over storage and the level of NAC and its oxidation product, $NAC_2$, in the cysteinyl-succinyl crosslinked hemoglobin solution were measured by reverse phase liquid chromatography. For the measurement, samples were treated with 5% meta-phosphoric acid to precipitate the proteins, and the supernatant was separated on a XBridged C18 column (5 μm, 4.6 mm×250 mm), using an isocratic elution in buffer containing 100 mM sodium phosphate pH 2.3, 5.7 mM sodium 1-octanesulfonate:methanol 91:9 (v/v). NAC and $NAC_2$ were quantified using their respective calibration curves ranging from 9.375 μg/mL to 300 μg/mL.

Figure 9:
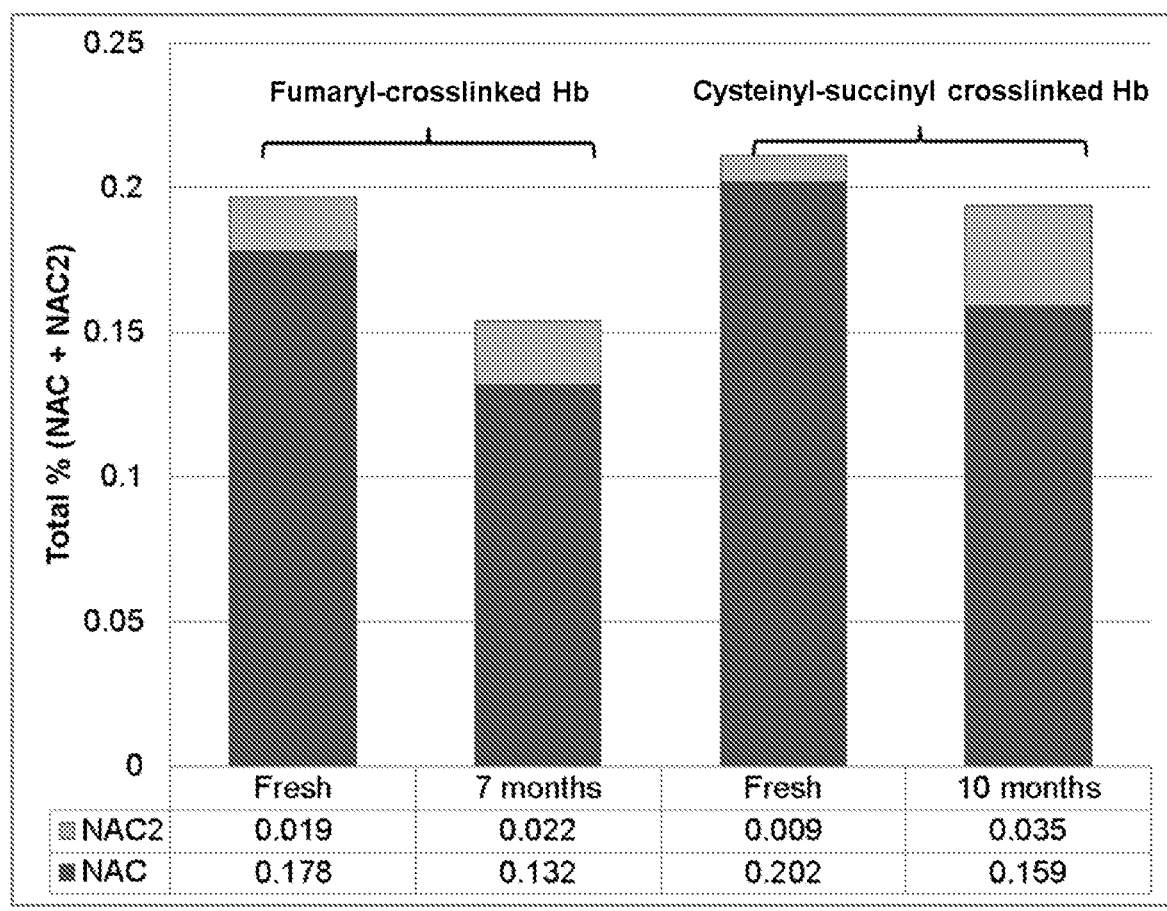
FIG. 9 depicts the stability of NAC and $NAC_2$ in cysteinyl-succinyl-crosslinked hemoglobin and fumaryl-crosslinked hemoglobin solution, respectively.

In contrast to the total level of NAC and $NAC_2$ in fumaryl-crosslinked hemoglobin solution (FIG. 9A), cysteinyl-succinyl crosslinked hemoglobin had stable levels of thiol excipient NAC over an extended period of time, as depicted in FIG. 9B.

Example 13: Functional Stability of Cysteinyl-Succinyl Crosslinked Hemoglobin

The p50 values of the fumaryl-crosslinked hemoglobin and cysteinyl-succinyl crosslinked hemoglobin solution in the presence of 0.2% NAC (v/v) were measured using the Hemox analyzer (TCS Scientific Corp). Hemoglobin product samples at 0.5 mg/mL in Hemox buffer (pH 7.4) were oxygenated by bubbling oxygen through for 30 min and then deoxygenated by bubbling nitrogen through until the $pO_2$ reached 1.9 mmHg. The resulting oxygen equilibrium curves were analyzed using the TCS software, using the Adair equation to adjust for incomplete oxygenation of the sample being measured.

Cysteinyl-succinyl crosslinked hemoglobin had a stable p50 value over at least 3 months post-production. In contrast, fumaryl-crosslinked hemoglobin showed a 12% increase in p50 values over 10 weeks presumably due to covalent binding of NAC to the β-β crosslinks of the crosslinked hemoglobin molecule, as depicted in Table 17.

TABLE 17 p50 Stability of Fumaryl-crosslinked Hemoglobin
and Cysteinyl-succinyl Crosslinked Hemoglobin,
in the Presence of 0.2% NAC, respectively.

| | Adair's p50 (mmHg) | |
|---|---|---|
| Time | Fumaryl-crosslinked Hemoglobin | Cysteinyl-succinyl Crosslinked Hemoglobin |
| At Release | 64 | 67 |
| 1 Month | 66 | 67 |
| 3 Month | 70 | 67 |

Example 14: In-Vivo Stability of Cysteinyl-Succinyl Crosslinked Hemoglobin

To assess the in-vivo stability of hemoglobin products, male Sprague Dawley rats were anesthetized by isoflurane (5% for induction, 1-2% for maintenance) and either fumaryl-crosslinked hemoglobin or cysteinyl-succinyl crosslinked hemoglobin was infused intravenously via the femoral vein at 0.8-2.0 mL per hour, at a dose level of 620 mg/kg. 0.5-1 mL blood samples were collected from the femoral artery 2 hours post infusion into heparin tubes. Hemoglobin products were enriched from plasma samples by strong anion exchange chromatography. Plasma samples were diluted 80000 times in 20 mM Tris-HCl pH 8.9 and loaded onto a HiTrap Q HP column (GE Healthcare) equilibrated in 20 mM Tris-HCl pH 8.9. Hemoglobin products were eluted using a HiTrap Q HP column (GE Healthcare) over a gradient of 0-400 mM NaCl in 20 mM Tris-HCl pH 8.9. Enrichment of hemoglobin products were assessed by sodium dodecyl sulfate polyacrylamide gel electrophoresis. Pooled fractions were analyzed by ESI-MS using an Agilent 6540 Electrospray Ionization Quadrupole-Time-of-Flight spectrometer.

Figure 10:
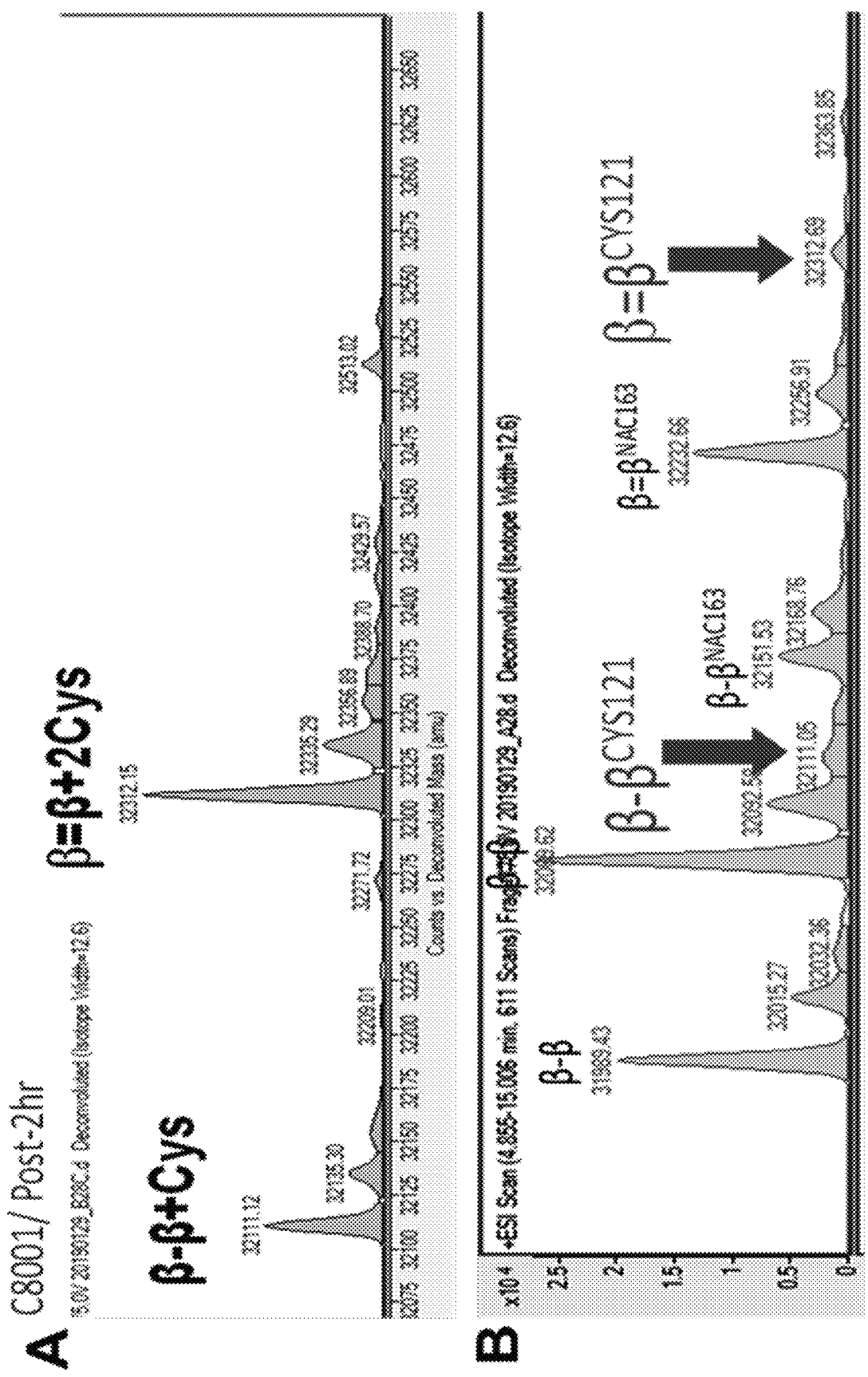
FIG. 10 depicts deconvoluted ESI-MS spectrum of (A) cysteinyl-succinyl crosslinked hemoglobin and (B) fumaryl-crosslinked hemoglobin, demonstrating in vivo stability of the hemoglobin in the blood circulation.

As depicted in FIG. 10A, the β-β crosslinks of cysteinyl-succinyl crosslinked hemoglobin did not undergo further modifications with thiols in-vivo compared to pre-infusion. In contrast, those of fumaryl-crosslinked hemoglobin product were modified with cysteine and NAC in-vivo (FIG.

10B). Cysteine is an important redox regulator in plasma, and NAC is an excipient in the hemoglobin product formulations. These results show the in-vivo stability of the cysteinyl-succinyl crosslinked hemoglobin.

Example 15: Restoration of Tissue Oxygenation in Hemorrhagic Shock (Fumaryl-Crosslinked Hemoglobin Vs. Cysteinyl-Succinyl Crosslinked Hemoglobin)

Liver tissue oxygenation was evaluated in a severe hemorrhagic shock model in Sprague Dawley rat as follows:
Group 1: Fumaryl-crosslinked Hemoglobin Solution (650 mg Hb/kg of body weight); and
Group 2: Cysteinyl-succinyl Crosslinked Hemoglobin Solution (650 mg Hb/kg of body weight).
Sprague Dawley rats were anesthetized and instrumented for surgical procedure. Laparotomy was performed by a large middle incision to expose the liver. A large area oxygen sensor (LAS, Oxford Optronix, UK) was inserted between the right lobe and triangle lobe of the rat liver and allowed for stabilization. After collection of baseline oxygen tension level, rats were rendered hypotensive by hemorrhage in order to trigger oxygen supply/demand imbalance as reflected by an elevated arterial lactate level (8 to 11 mM/L) and an arterial base excess <−12 mM/L. Following the induction of shock and meeting the entry criteria, rats were administered with infusion of either 650 mg/kg fumaryl-crosslinked hemoglobin solution (Group 1) or cysteinyl-succinyl crosslinked hemoglobin solution (Group 2). The liver oxygen tension levels of these 2 hemoglobin molecules were monitored and compared up to 1 hour post-infusion.

Figure 11:
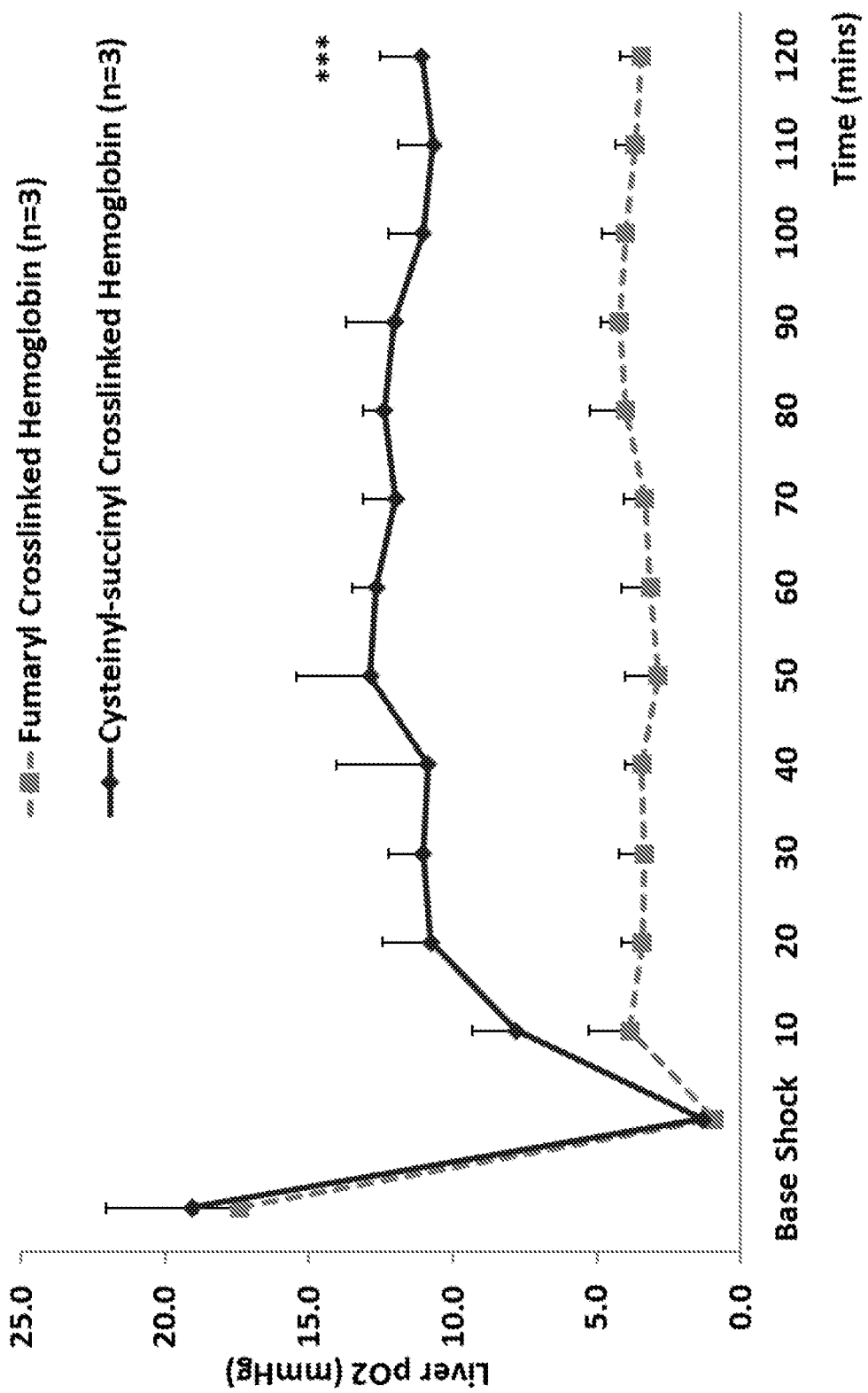
FIG. 11 shows the injection of 650 mg/kg cysteinyl-succinyl crosslinked hemoglobin solution results in a significant increase in liver tissue oxygen level comparing with fumaryl-crosslinked hemoglobin solution in rat severe hemorrhagic shock. Data are reported as mean±SD. Statistical analysis is performed by two-way ANOVA. ***$p<0.001$ vs fumaryl-crosslinked hemoglobin solution.

As shown in FIG. 11, results indicate that the infusion of 650 mg/kg cysteinyl-succinyl crosslinked hemoglobin solution (Group 2) showed a significant increase in liver tissue oxygenation, comparing to fumaryl-crosslinked hemoglobin solution (Group 1) throughout the experiment.

This reveals that the cysteinyl-succinyl crosslinked hemoglobin has a superior oxygen off-loading capability in ischemic/hypoxic conditions, compared to conventional fumaryl-crosslinked hemoglobin.

Example 16: Restoration of Blood Perfusion in Ischemic Limb (Fumaryl-Crosslinked Hemoglobin Vs. Cysteinyl-Succinyl Crosslinked Hemoglobin)

Restoration of blood flow in ischemic limb was evaluated in mice by performing femoral artery ligation mimicking peripheral artery disease.
Group 1: Negative Control (Volume-matched RA-buffer, n=8)
Group 2: Fumaryl-crosslinked Hemoglobin Solution (1600 mg/kg, n=2)
Group 3: Cysteinyl-succinyl Crosslinked Hemoglobin Solution (1600 mg/kg, n=3)
To induce critical limb ischemia, ICR (CD-1) mice were anesthetized to perform surgical procedure. The femoral artery was ligated to the distal point where it bifurcated into the saphenous and popliteal arteries. At post 24 hours arterial ligation, mice were administrated with different treatments via bolus tail vein injection. Serial Laser Doppler Imaging analysis (Moor instruments, Devon, UK) was performed to monitor blood flow at baseline, right after ligation, Day 7 post treatment, Day 14 post treatment and Day 21 post treatment and the mean blood flow from the knee to toe was quantified and calculated. Tivi600 Tissue viability imager modulating with Tivi106 Oxygen Mapper analyzer (Wheels-Bridge AB, Sweden) was performed to monitor change in oxygenated hemoglobin at baseline, right after ligation, 30 minutes post treatment, 60 minutes post treatment, Day 7 post treatment, Day 14 post treatment and Day 21 post treatment. The mean change in oxygenated Hb (Oxy-Hb) from the knee to toe was quantified and calculated.

Figure 12:
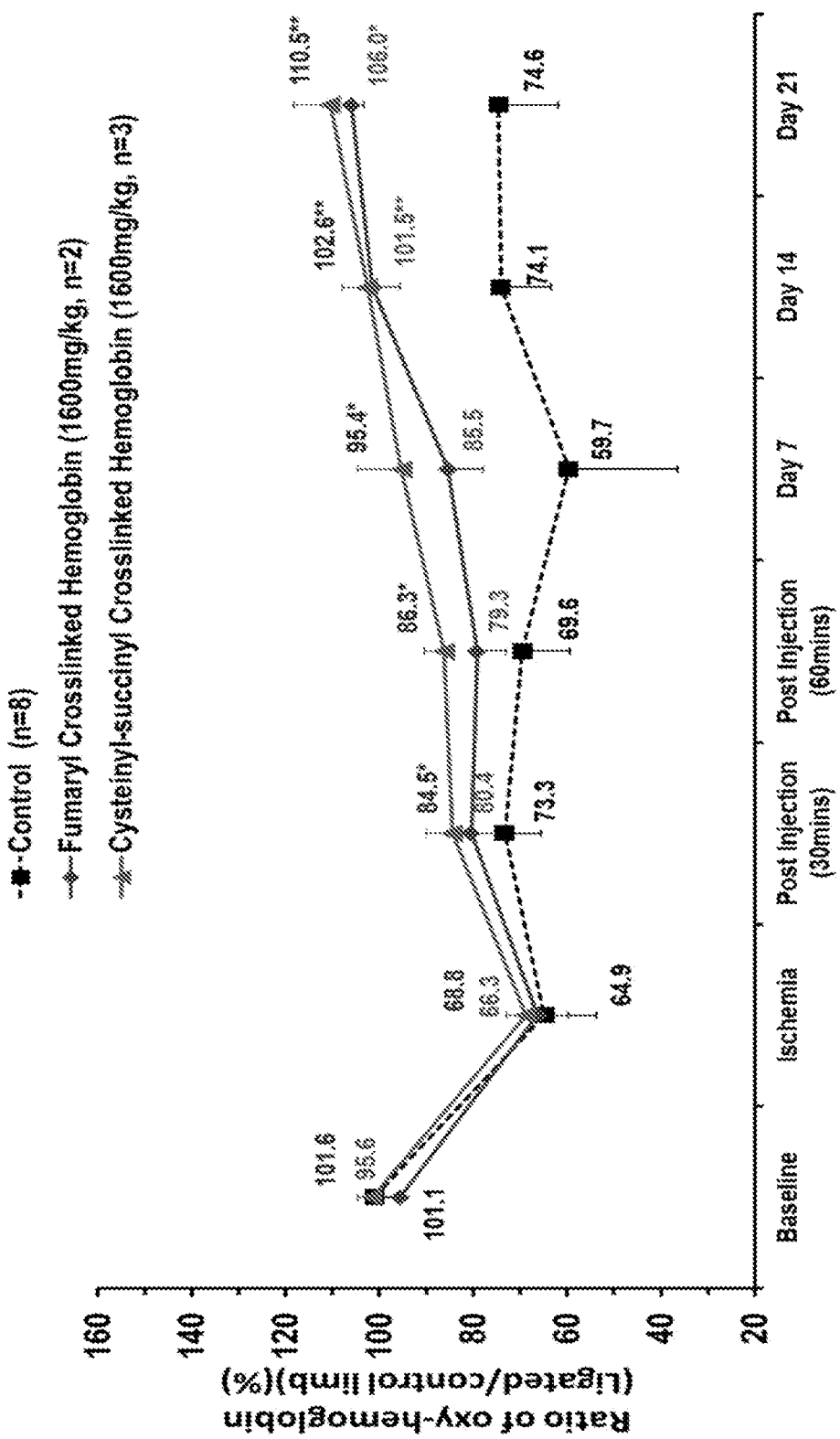
FIG. 12 shows an increase in Oxy-Hb level in the ischemic limb following cysteinyl-succinyl crosslinked hemoglobin and fumaryl-crosslinked hemoglobin treatment. Oxy-Hb is measured by the TiVi 700 Tissue Viability Imager with Oxygen Mapper before and after inducing limb ischemia, and at different time points up to 21 days following treatment. For cysteinyl-succinyl crosslinked hemoglobin treatment, a significant increase in Oxy-Hb is observed in 30 minutes post infusion, and up to 21 days post treatment whereas fumaryl-crosslinked hemoglobin shows a significant increase in 14 days post treatment and 21 days post treatment. The Oxy-Hb level is expressed as the flux density measured in the ligated limb divided by the control limb (without ligation) in the same mouse at the same time point. Data are reported as mean±SD. *$p<0.05$, **$p<0.01$ vs control group.

As shown in FIG. 12, there was significant increase in Oxy-Hb in group of mice receiving cysteinyl-succinyl crosslinked hemoglobin treatment was compared with RA-buffer group (negative control) at 30 minutes post-treatment (p<0.05), whereas fumaryl-crosslinked hemoglobin treatment did not show significant increase in Oxy-Hb as compared with RA-buffer group. At Day 21 post-treatment, mice treated with both cysteinyl-succinyl crosslinked hemoglobin solution (110.5±7.8%, p<0.01 vs control) and fumaryl-crosslinked hemoglobin solution (106.0±2.6%, p<0.05 vs control) showed significantly higher level of Oxy-Hb than RA-buffer (74.6±12.7%).

Figure 13:
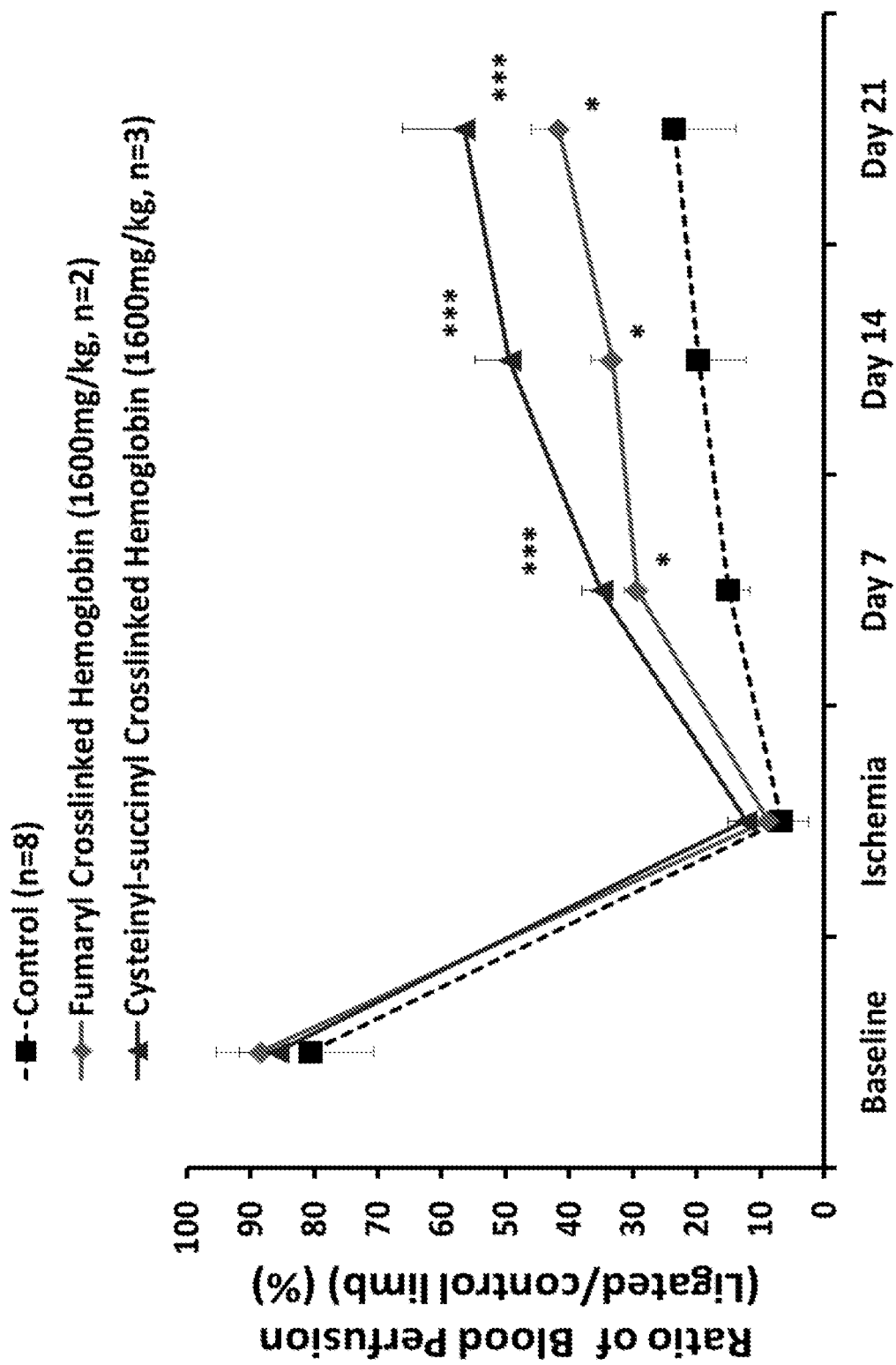
FIG. 13 shows a restoration of perfusion in ischemic limb following cysteinyl-succinyl crosslinked hemoglobin and fumaryl-crosslinked hemoglobin treatment. Blood perfusion is measured by the Moor Serial Laser Doppler Imager before and after inducing limb ischemia, and at different time points up to 21 days following treatment. A significant restoration of perfusion is observed up to 21 days following cysteinyl-succinyl crosslinked hemoglobin and fumaryl-crosslinked hemoglobin treatment. Data are reported as mean±SD. *$p<0.05$, $p<0.01$, *$p<0.001$ vs control group.

As shown in FIG. 13, there was a significant improvement of ischemic limb blood flow in the group of mice receiving cysteinyl-succinyl crosslinked hemoglobin solution (34.9±3.0%, p<0.001) and fumaryl-crosslinked hemoglobin solution (29.3±2.0%, p<0.05) as compared with RA-buffer group (negative control) at Day 7 post-treatment, a similar trend of significant increase in perfusion with the cysteinyl-succinyl crosslinked hemoglobin treatment was observed from Day 7 onward. At Day 21 post-treatment, mice treated with cysteinyl-succinyl crosslinked hemoglobin solution (56.5±9.6%, p<0.001 vs control) resulted in a more significant improvement in blood perfusion compared with stabilized fumaryl-crosslinked hemoglobin solution (41.6±4.3%, p<0.05 vs control), and RA-buffer (23.5±9.7%).

Figure 14:
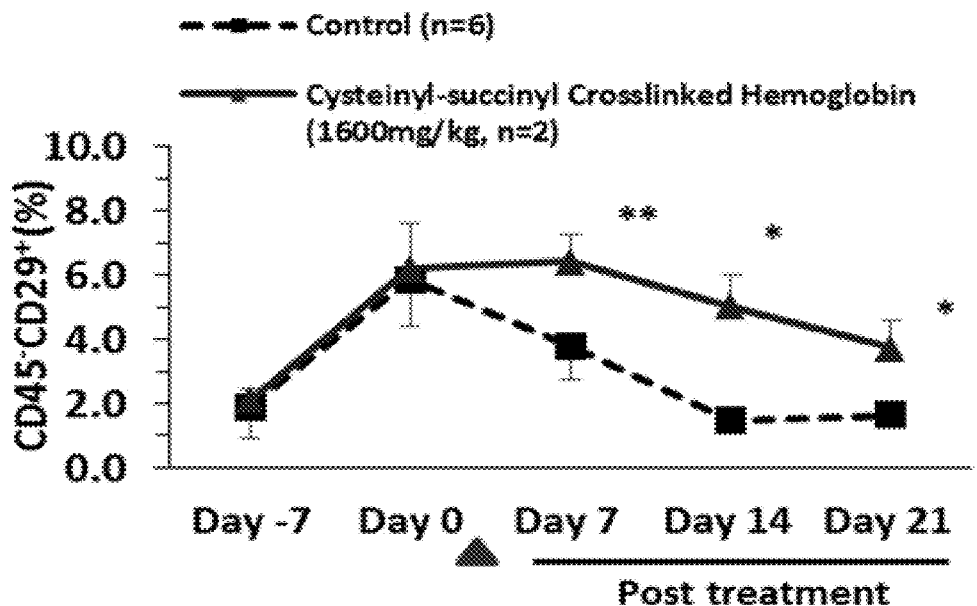
FIG. 14 shows maintenance of mesenchymal stem cell (MSC) populations in limb ischemia following cysteinyl-succinyl crosslinked hemoglobin and fumaryl-crosslinked hemoglobin treatment. An increase in circulating $CD45^-CD29^+$, $CD45^-CD105^+$, $CD45^-CD106^+$ MSC populations is observed after inducing limb ischemia and which sustains for a longer period of time compared with control. A more significant improvement in MSC populations is observed upon cysteinyl-succinyl crosslinked hemoglobin treatment. Data are reported as mean±SD. *$p<0.05$, $p<0.01$, *$p<0.001$ vs control group.
Figure 14:
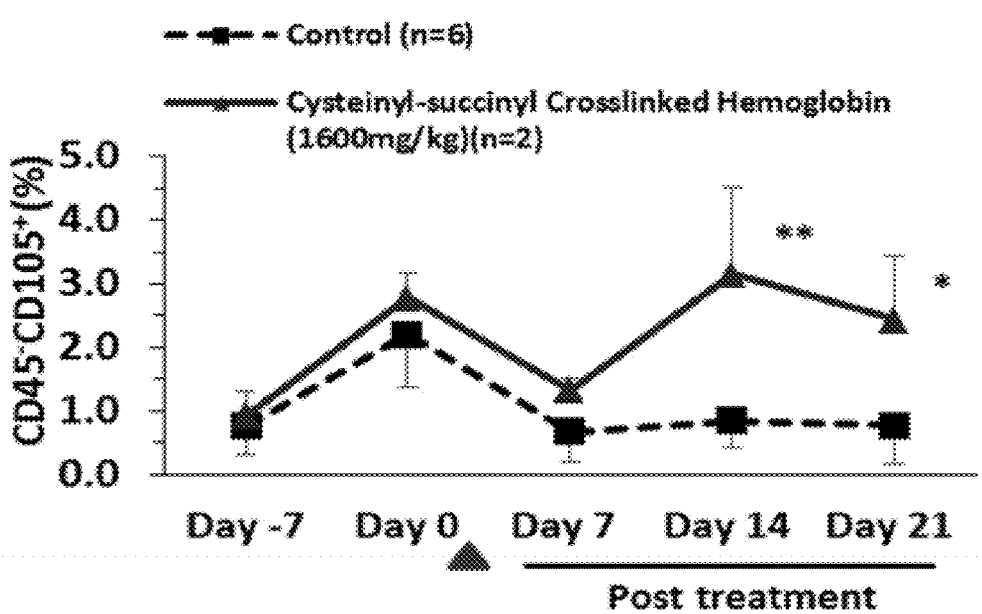
Figure 14:
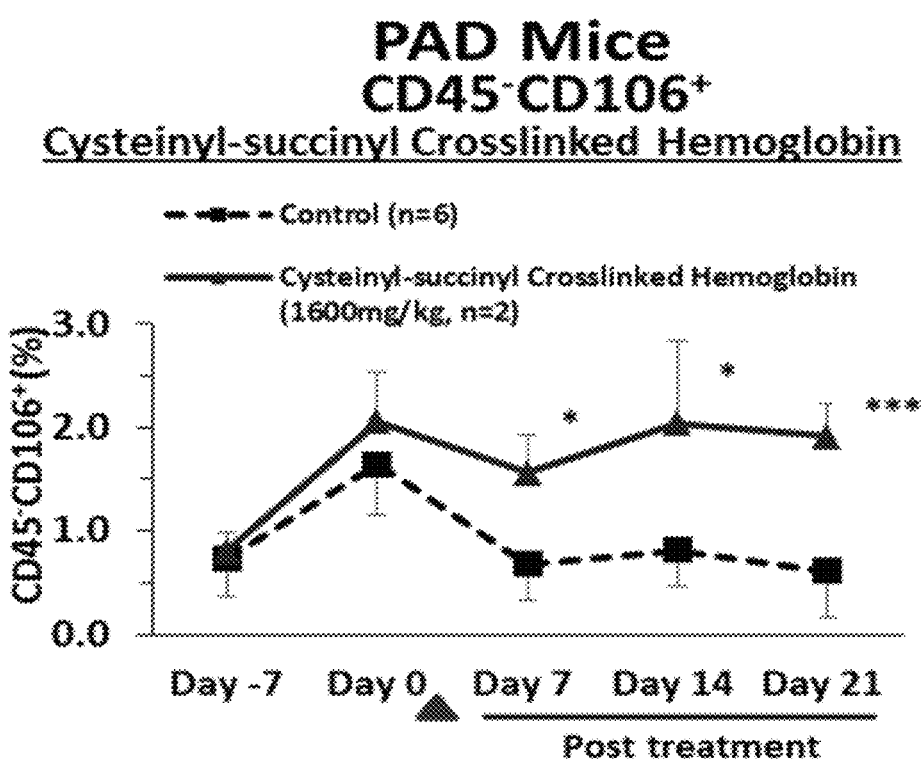
Figure 14:
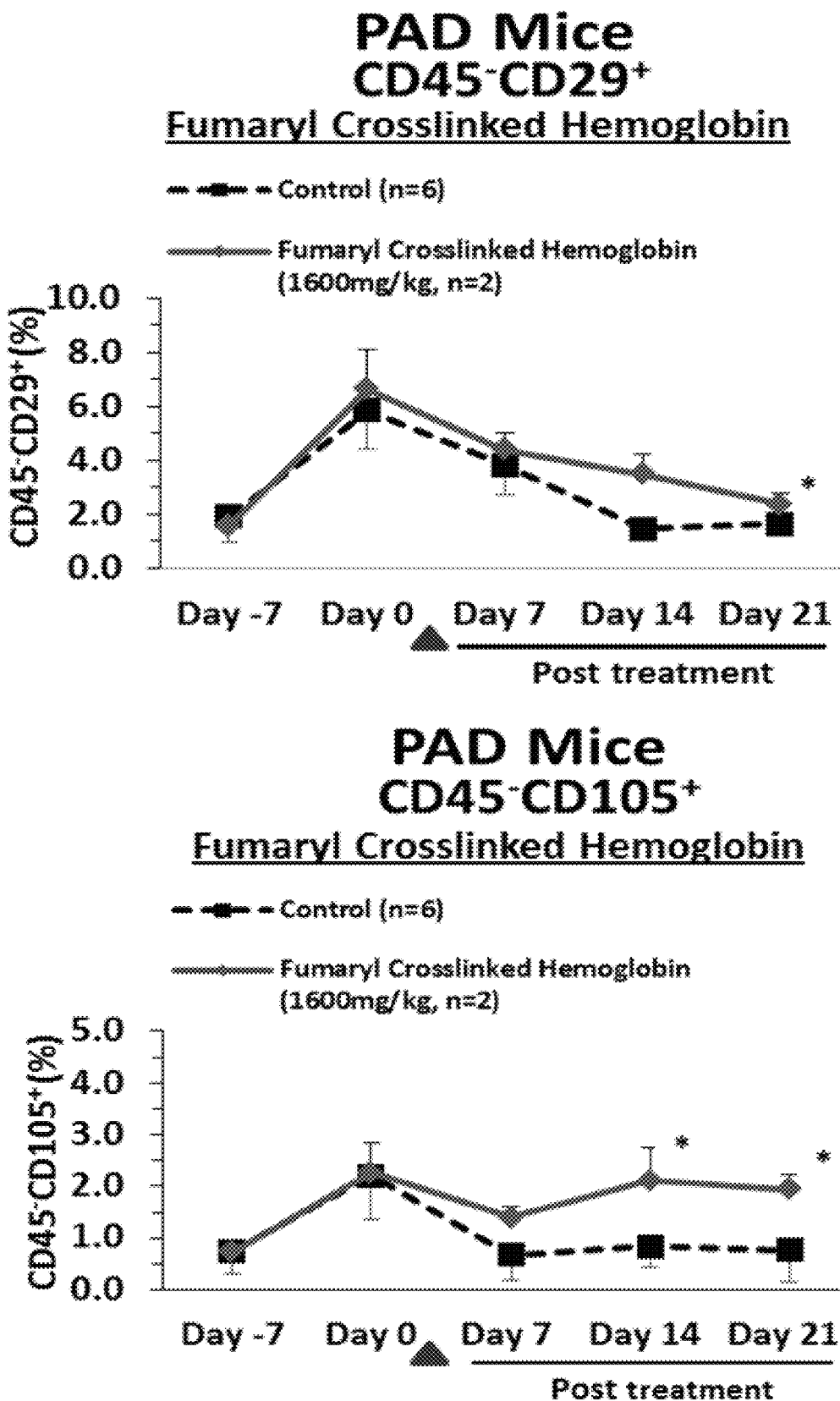
Figure 14:
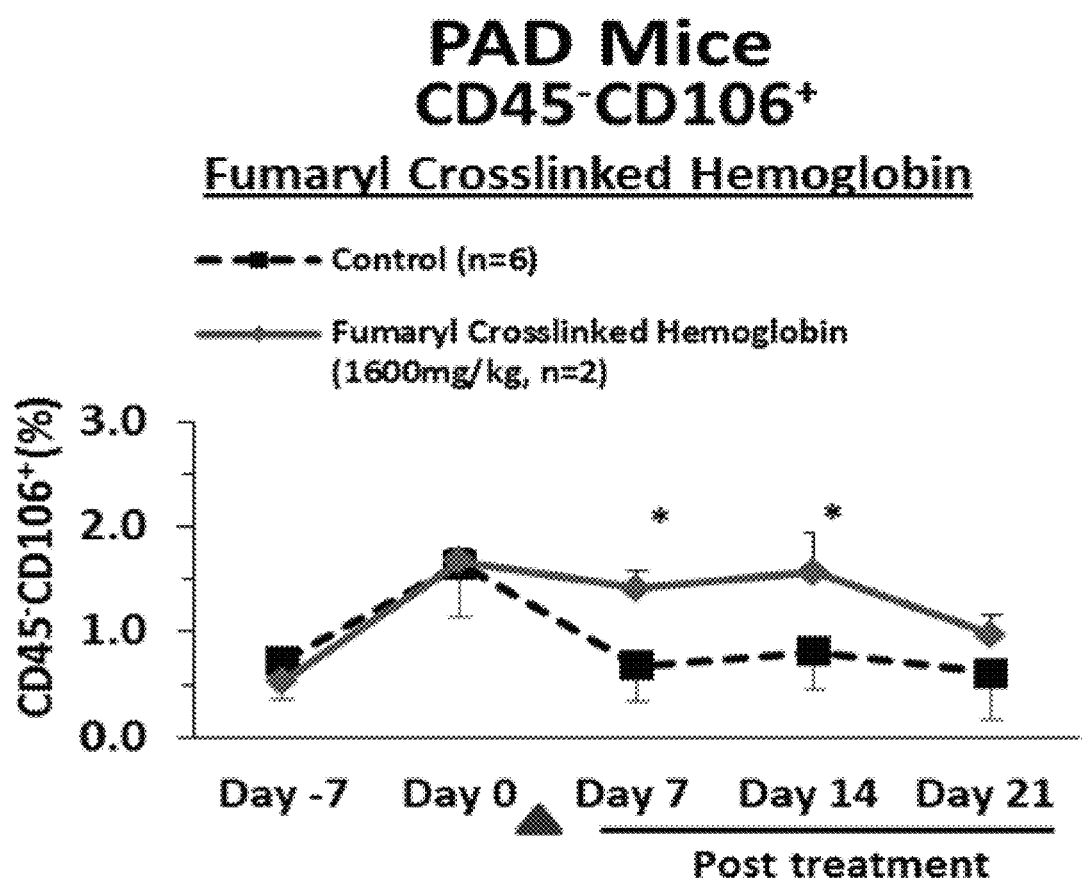

To gain mechanistic insights into the "sustained" improvement of Oxy-Hb and perfusion on Day 21, circulating mesenchymal stem cell populations were analyzed by flow cytometry at different time points post treatment. As shown in FIG. 14, results indicated an increase in $CD45^-CD29^+$, $CD45^-CD105^+$, $CD45^-CD106^+$ MSC populations were observed following induction of limb ischemia and which sustained for a longer period of time up to Day 21 comparing with control. Consistent with the restoration in perfusion, a more significant increase in MSC populations was observed following cysteinyl-succinyl crosslinked hemoglobin treatment.

Collectively, cysteinyl-succinyl crosslinked hemoglobin showed better treatment effect than conventional fumaryl-crosslinked hemoglobin, in terms of oxygenated hemoglobin, blood flow and circulating mesenchymal stem cell populations in peripheral artery disease model.

Example 17: Method of Using Stabilized Cysteinyl-Succinyl Crosslinked Hemoglobin The cysteinyl-succinyl crosslinked hemoglobin solution of the present disclosure was used for improving the delivery of oxygen and treatment against global and regional ischemic/hypoxic conditions including hemorrhagic shock, myocardial ischemia reperfusion injury, peripheral artery disease and traumatic brain injury. In addition, the cysteinyl-succinyl crosslinked hemoglobin solution was also used for treating autoimmune diseases and cancer treatment as follows:
Hemorrhagic Shock: a restoration of tissue oxygenation and mean arterial pressure in hemorrhagic shock;
Peripheral Artery Disease: a significant restoration of blood flow and increase in Oxy-Hb level in critical limb ischemia;

Myocardial Ischemia Reperfusion Injury: a significant reduction of myocardial infraction in heart;

Systemic Lupus Erythematosus: a significant reduction in immune complex formation in tissues/organs and amelioration of tissue/organ damages;

Traumatic Brain Injury: a significant improvement in both neurological and motor functions and a reduction of TBI-induced astrocyte activation in controlled cortical impact (CCI) induced traumatic brain injury; and Cancer Treatment: a significant inhibition of tumor growth in triple-negative breast cancer (TNBC) and colorectal cancer xenograft model, respectively.

The dosage of cysteinyl-succinyl crosslinked hemoglobin is approximately 100-1600 mg/kg.

Example 18: Treatment of Severe Hemorrhagic Shock in Cynomolgus Monkey

Cysteinyl-succinyl crosslinked hemoglobin was used for the treatment of severe hemorrhagic shock in cynomolgus monkey.

Muscle tissue oxygenation and mean arterial pressure were evaluated in a severe hemorrhagic shock model in cynomolgus monkey as follows:

Group 1: Autologous Plasma (Positive control, equivalent volume of cysteinyl-succinyl crosslinked hemoglobin administrated) (n=2)

Group 2: Cysteinyl-succinyl Crosslinked Hemoglobin Solution (500 mg/kg of body weight) (n=2)

Cynomolgus monkeys were anesthetized and instrumented for surgical procedure. A needle encased oxygen sensor (Oxford Optronix, UK) was inserted in triceps and allowed to stabilize. A blood pressure sensor (Biopac Systems Inc, US) was inserted in the left femoral artery and allowed to stabilize. After collection of baseline oxygen tension level and mean arterial pressure, monkeys were rendered hypotensive by hemorrhage to decrease mean arterial pressure to 20 mmHg and kept maintaining the mean arterial pressure ranging from 20-24 mmHg for 60 minutes. Following the induction of shock and meeting the criteria, monkeys were administered with infusion of either autologous plasma (positive control) or cysteinyl-succinyl crosslinked hemoglobin solution. The muscle oxygenation tension level and mean arterial pressure of these two groups were measured and compared up to 3 hour post-infusion.

Figure 15:
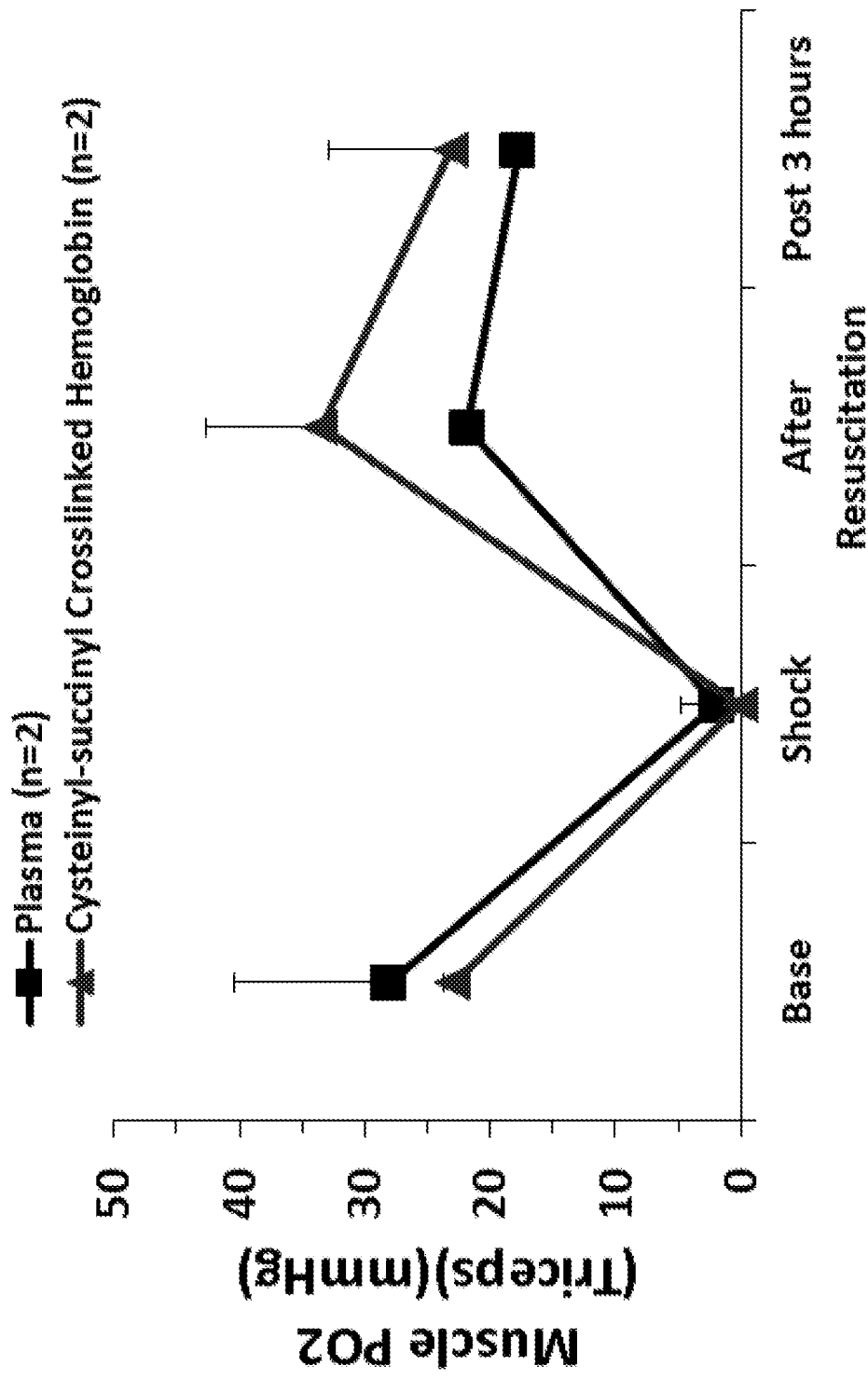
FIG. 15 shows a cysteinyl-succinyl crosslinked hemoglobin restored oxygenation in muscle tissue (triceps) under a non-human primate (cynomolgus monkey) model of severe hemorrhagic shock. Infusion of 500 mg/kg cysteinyl-succinyl crosslinked hemoglobin results in an increase in muscle tissue oxygenation when comparing with autologous plasma treatment (control). Data are reported as mean±SD.
Figure 16:
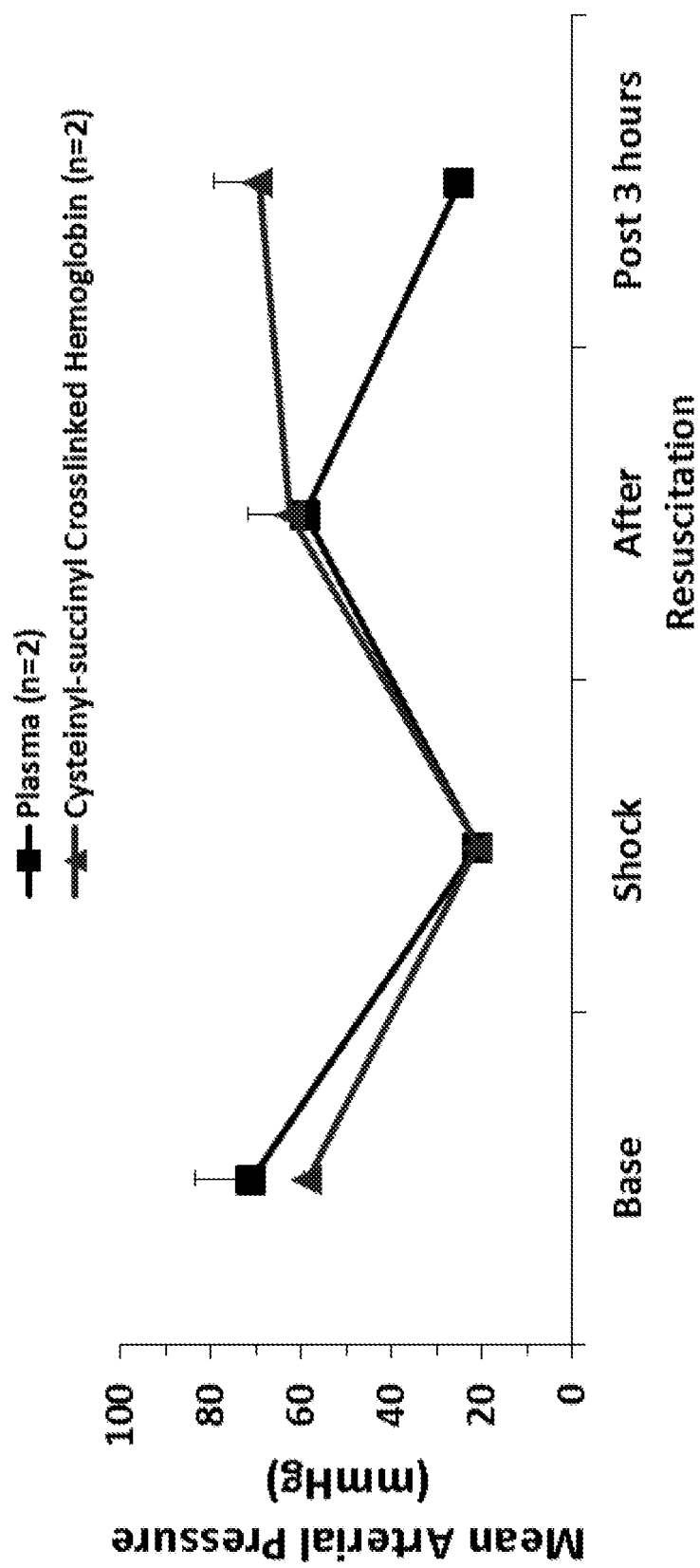
FIG. 16 shows a restoration of mean arterial pressure in a non-human primate model of severe hemorrhagic shock following cysteinyl-succinyl crosslinked hemoglobin treatment. Comparing with autologous plasma treatment, a higher mean arterial pressure is maintained up to 3 hours following the cysteinyl-succinyl crosslinked hemoglobin treatment. Data are reported as mean±SD.

As shown in FIG. 15, results indicate the infusion of 500 mg/kg cysteinyl-succinyl crosslinked hemoglobin solution resulted in an increase in muscle tissue oxygenation after resuscitation and kept better restoration at post 3 hours of resuscitation. For mean arterial pressure restoration, infusion with the cysteinyl-succinyl crosslinked hemoglobin solution resulted in a better restoration of mean arterial pressure than autologous plasma treatment at post 3 hours time point of resuscitation, as shown in FIG. 16.

This reveals that cysteinyl-succinyl crosslinked hemoglobin increased tissue oxygenation and maintained a better restoration of mean arterial pressure in cynomolgus monkey with severe hemorrhagic shock.

Example 19: Treatment of Peripheral Artery Disease in Mice

Cysteinyl-succinyl crosslinked hemoglobin was used for blood perfusion and the delivery of oxygen in attenuated critical limb ischemia in mice.

Restoration of blood flow in ischemic limb was evaluated in mice by performing femoral artery ligation mimicking peripheral artery disease. In this study, 32 mice were randomly assigned into 4 groups, 8 mice in each group.

Group 1: RA-Buffer (Negative Control, volume-matched to Group 4);

Group 2: Cysteinyl-succinyl Crosslinked Hemoglobin Solution (400 mg Hb/kg of body weight);

Group 3: Cysteinyl-succinyl Crosslinked Hemoglobin Solution (800 mg Hb/kg of body weight); and Group 4: Cysteinyl-succinyl Crosslinked Hemoglobin (1600 mg Hb/kg of body weight).

To induce critical limb ischemia, ICR (CD-1) mice were anesthetized to perform surgical procedure. The femoral artery was ligated to the distal point where it bifurcates into the saphenous and popliteal arteries. At post 24 hours arterial ligation, mice were administrated with different treatments via bolus tail vein injection. Serial laser Doppler imaging analysis (Moor instruments, Devon, UK) was performed to monitor blood flow at baseline, right after ligation, Day 7 post treatment, Day 14 post treatment and Day 21 post treatment and the mean blood flow from the knee to toe was quantified and calculated. Tivi600 Tissue viability imager modulating with Tivi106 Oxygen Mapper analyzer (Wheels-Bridge AB, Sweden) was performed to monitor change in oxygenated hemoglobin at baseline, right after ligation, 30 minutes post treatment, 60 minutes post treatment, Day 7 post treatment, Day 14 post treatment and Day 21 post treatment. The mean change in oxygenated Hb from the knee to toe was quantified and calculated.

Figure 17:
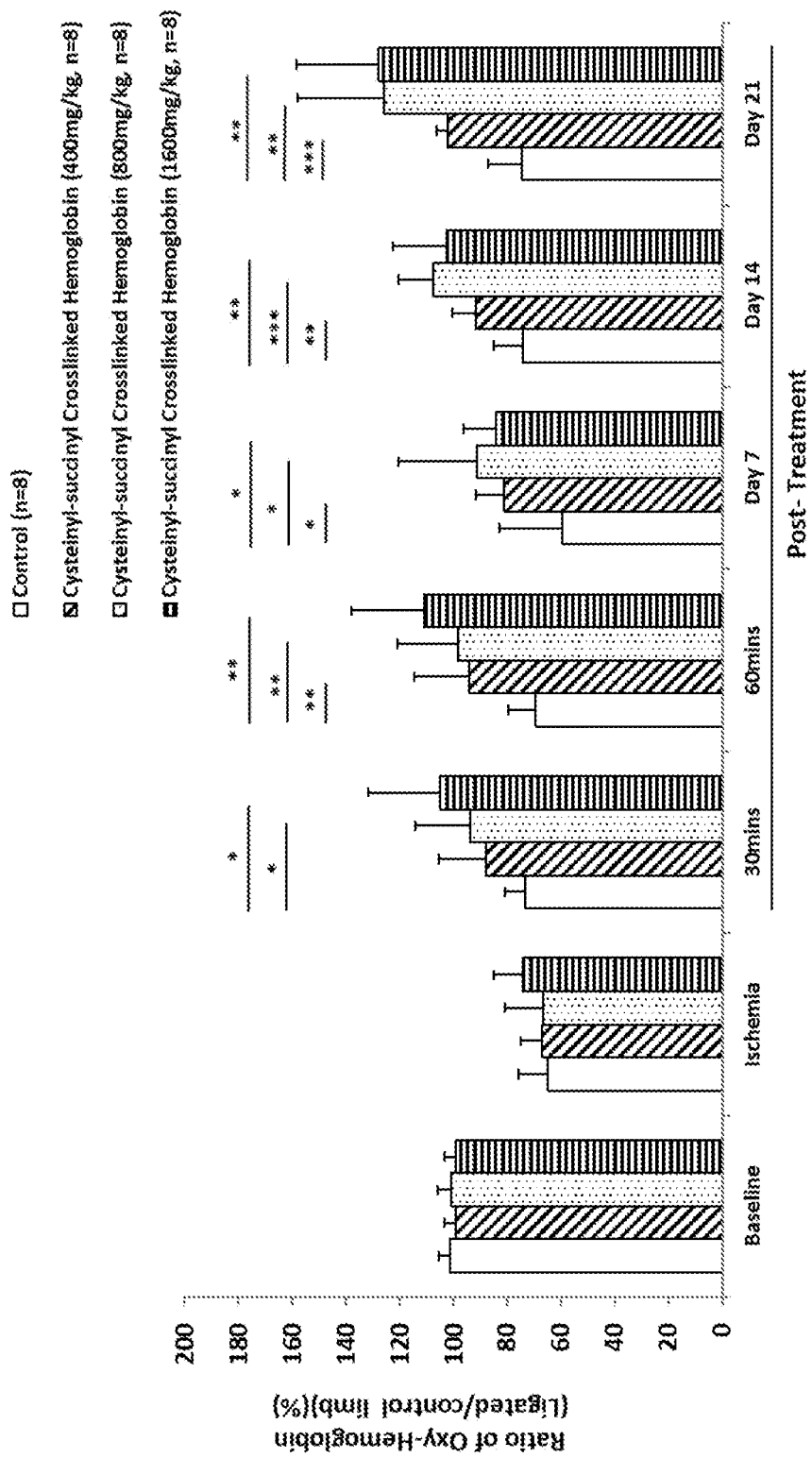
FIG. 17 shows a dose-dependent increase in Oxy-Hb level in the ischemic limb following treatment with cysteinyl-succinyl crosslinked hemoglobin solution. Oxy-Hb is measured by the TiVi 700 Tissue Viability Imager with Oxygen Mapper before and after inducing limb ischemia, and at different time points up to 21 days following treatment with cysteinyl-succinyl crosslinked hemoglobin solution (n=8 per group). A significant and dose-dependent increase in Oxy-Hb is observed in 1 hour post infusion, and up to 21 days post treatment. The Oxy-Hb level is expressed as the flux density measured in the ligated limb divided by the control limb (without ligation) in the same mouse at the same time point. Data are reported as mean±SD. *$p<0.05$, $p<0.01$, *$p<0.001$ vs negative control group.

As shown in FIG. 17, there was a significant and dose-dependent increase in Oxy-Hb in all group of mice receiving cysteinyl-succinyl crosslinked hemoglobin (Hb) as compared with RA-buffer group (Group 1) at 30 minutes post-treatment (800 mg/kg Hb, *$p<0.05$; 1600 mg/kg Hb, *$p<0.05$). At Day 21 post-treatment, mice treated with 400 mg/kg Hb (102.3±4.0%, p *$<0.001$), 800 mg/kg Hb (125.7±32.3%, $p<0.01$) and 1600 mg/kg Hb (128.0±30.5%, **$p<0.01$) showed significantly higher level of oxygenated Hb than RA-buffer (74.6±12.7%).

Figure 18:
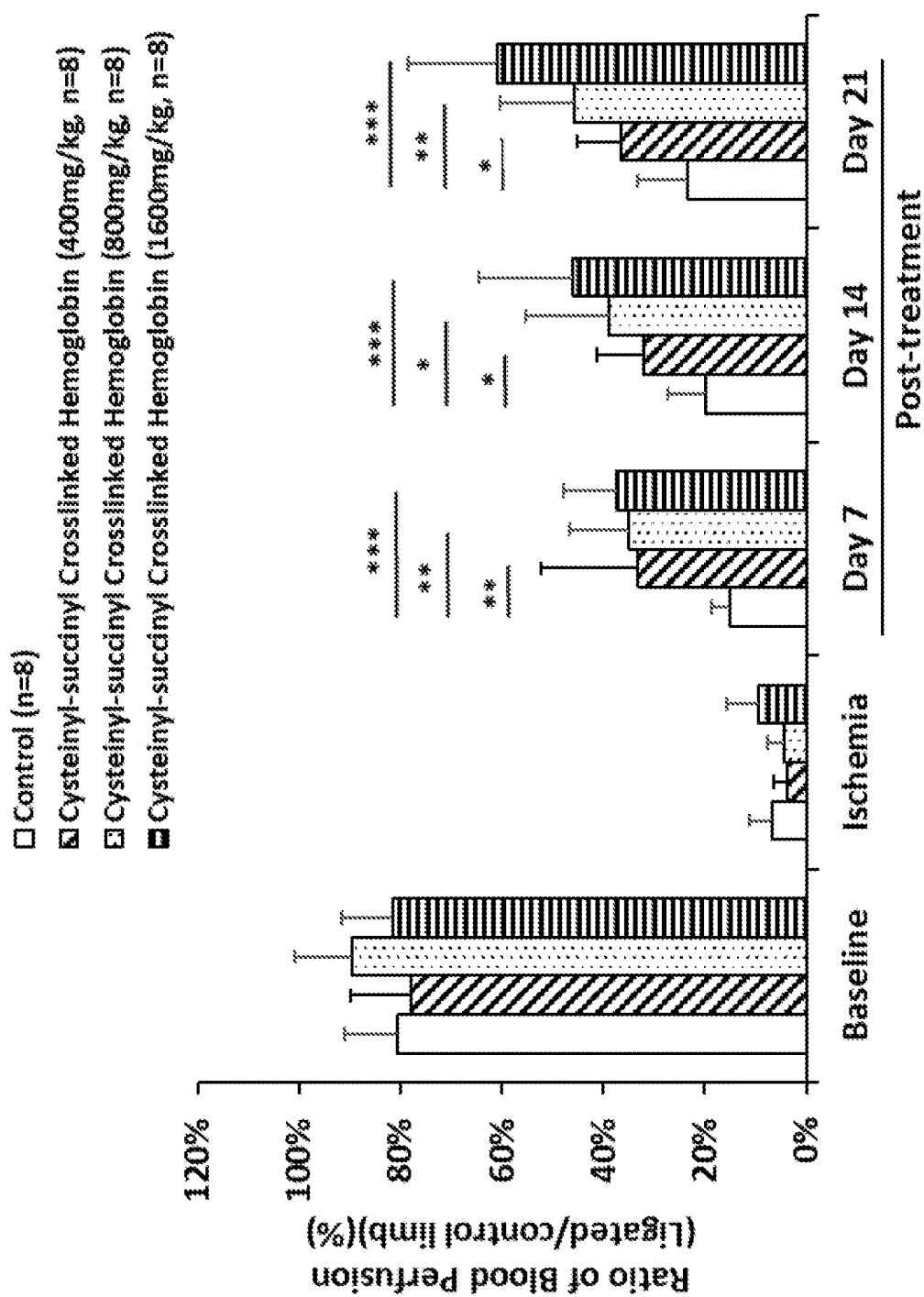
FIG. 18 shows a dose-dependent restoration of perfusion in ischemic limb following treatment with cysteinyl-succinyl crosslinked hemoglobin solution. Blood perfusion is measured by the Moor Serial Laser Doppler Imager before and after inducing limb ischemia, and at different time points up to 21 days following treatment with cysteinyl-succinyl crosslinked hemoglobin solution. A significant and dose-dependent restoration of perfusion is observed up to 21 days following treatment with cysteinyl-succinyl crosslinked hemoglobin solution (n=8 per group). Data are reported as mean±SD. *$p<0.05$, $p<0.01$, *$p<0.001$ vs negative control group.

As shown in FIG. 18, there was a significant improvement of ischemic limb blood flow in all group of mice receiving cysteinyl-succinyl crosslinked hemoglobin solution (Group 2-4) as compared with RA-buffer group (Group 1) from Day 7 post-treatment onward (400 mg/kg Hb, $p<0.01$; 800 mg/kg Hb, p<$0.01$; 1600 mg/kg Hb, ***$p<0.001$). At Day 21 post-treatment, mice treated with 400 mg/kg Hb (36.5±8.5%, *$p<0.05$), 800 mg/kg Hb (45.7±14.7%, $p<0.01$) and 1600 mg/kg Hb (61.0±15.2%, *$p<0.001$) showed higher significant blood flow than RA-buffer (23.5±9.7%).

Figure 19:
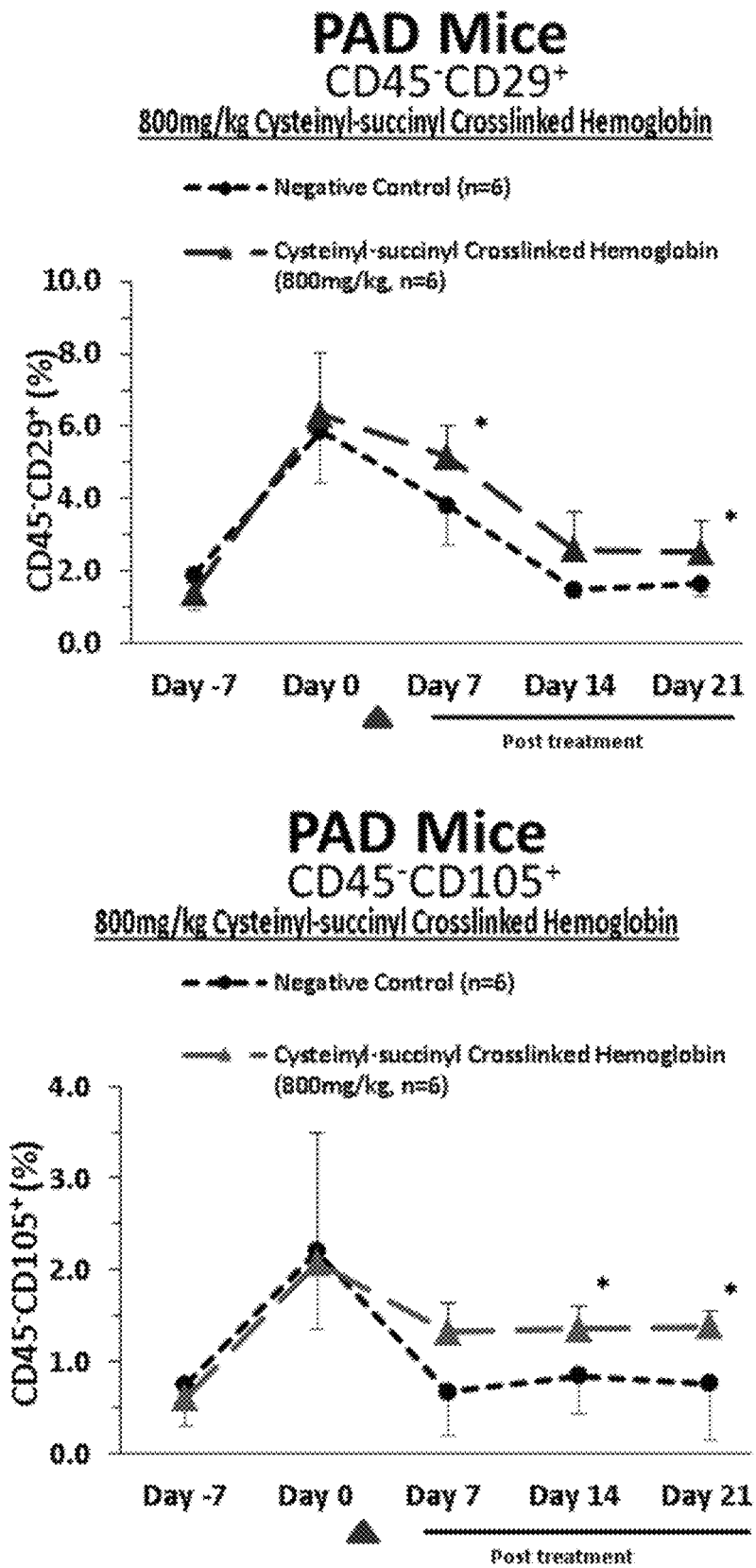
FIG. 19 depicts a selective activation of mesenchymal stem cell (MSC) populations in limb ischemia following treatment with cysteinyl-succinyl crosslinked hemoglobin solution. A significant and dose-dependent increase in circulating $CD45^-CD29^+$, $CD45^-CD105^+$, $CD45^-CD106^+$ MSC populations is observed after inducing limb ischemia and which sustained for a longer period of time compared with negative control. Data are reported as mean±SD. *$p<0.05$, $p<0.01$, *$p<0.001$ vs negative control group.
Figure 19:
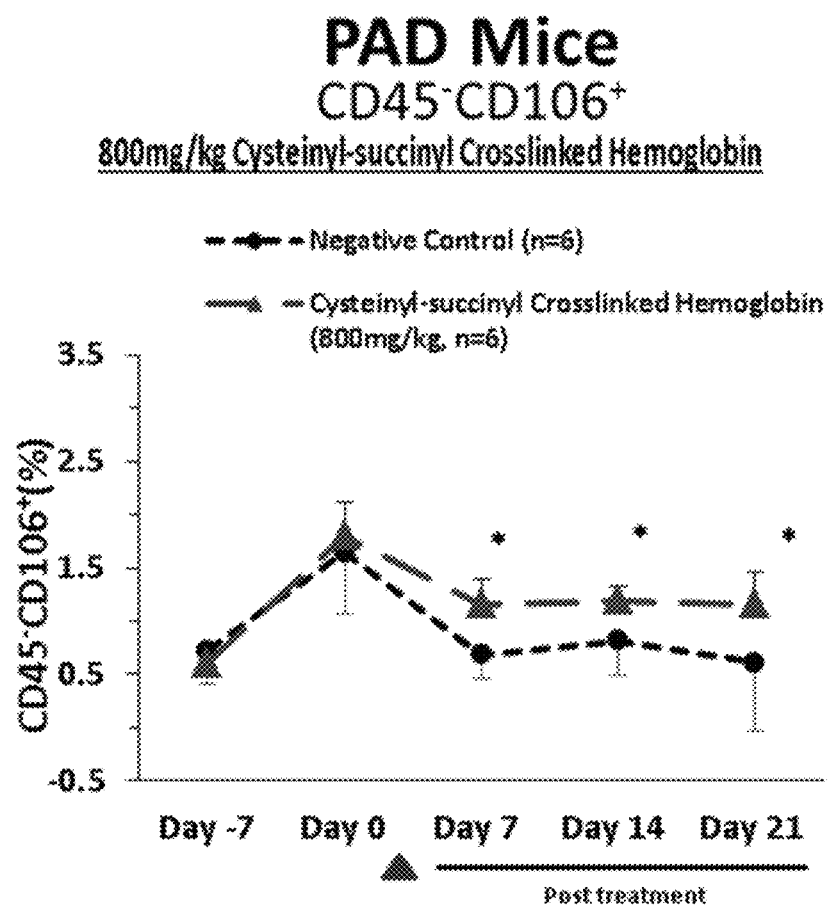
Figure 19:
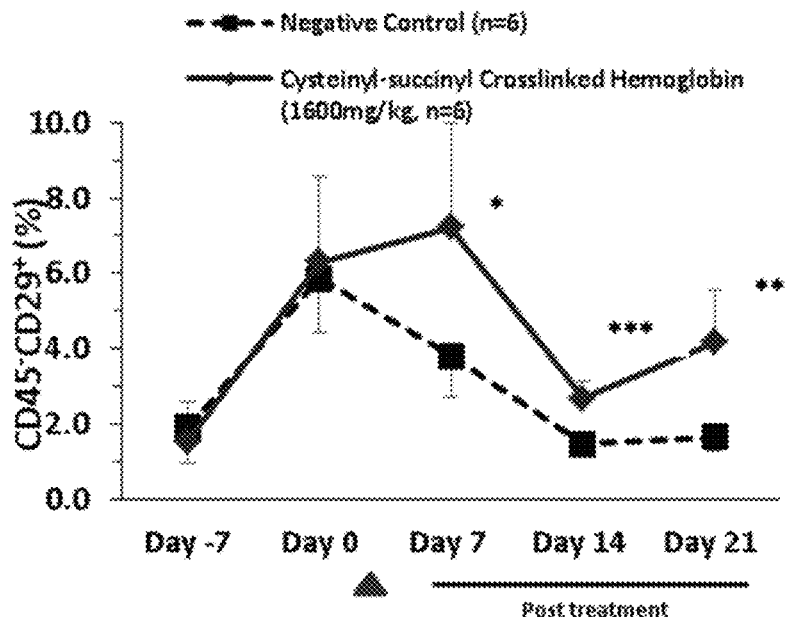
Figure 19:
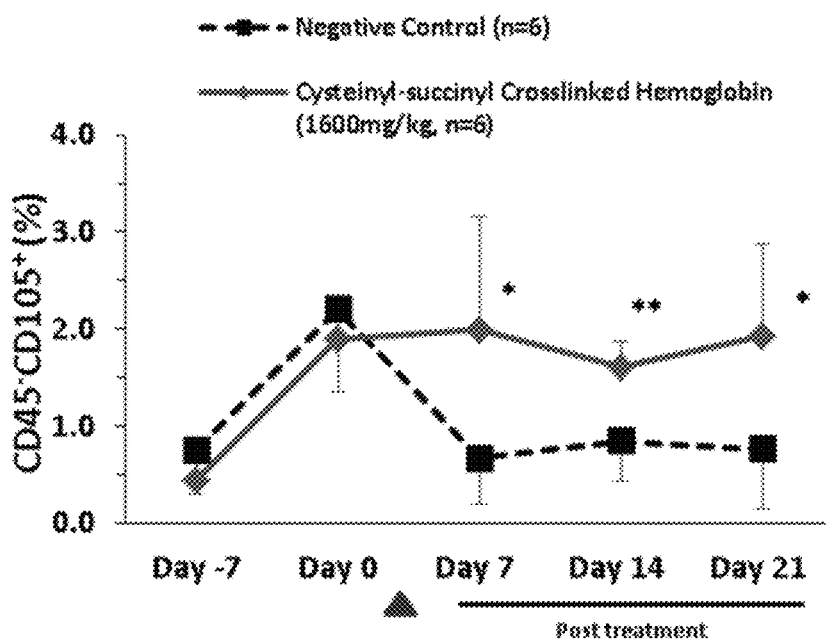
Figure 19:
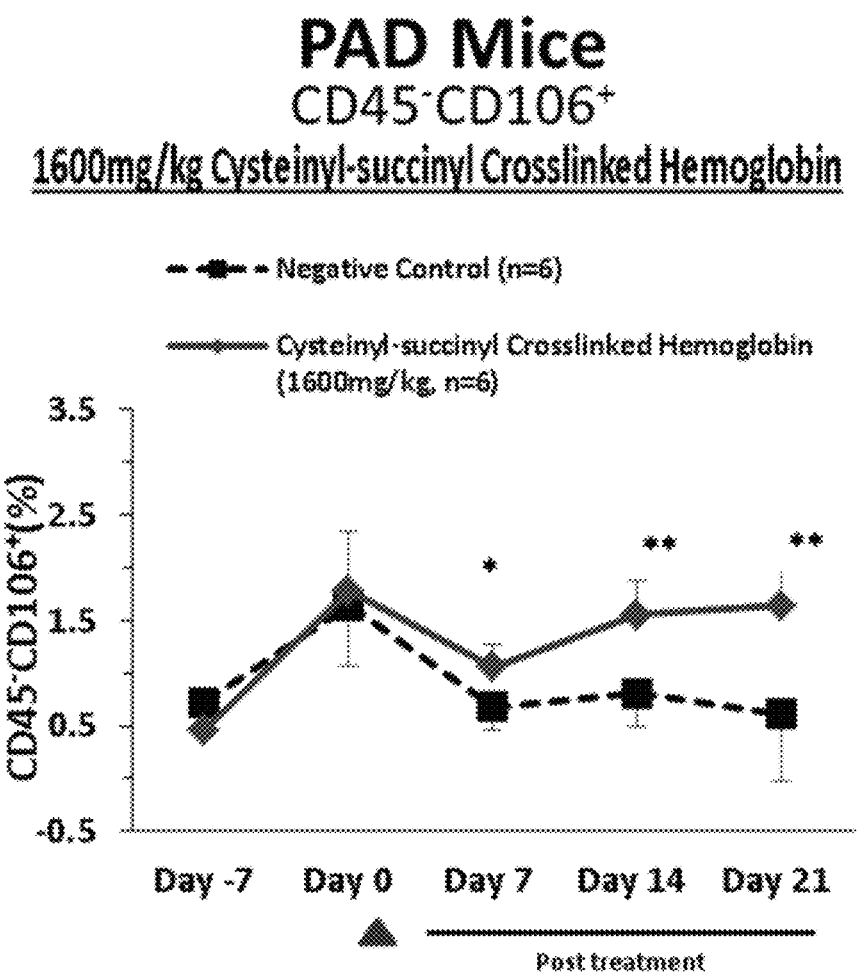

To gain mechanistic insights into the "sustained" improvement of Oxy-Hb and perfusion on Day 21, circulating mesenchymal stem cell populations were analyzed by flow cytometry at different time points post treatment. As shown in FIG. 19, results indicate an increase in $CD45^-CD29^+$, $CD45^-CD105^+$, $CD45^-CD106^+$ MSC populations were observed following induction of limb ischemia and which sustained for a longer period of time up to Day 21 comparing with negative control group. This was consistent with the observation of the significant increase in Oxy-Hb and perfusion at Day 21 post-treatment.

Collectively, the experimental data demonstrates that cysteinyl-succinyl crosslinked hemoglobin activated circulating mesenchymal stem cells and resulted in a functional restoration of perfusion and the delivery of oxygen in attenuated critical limb ischemia in mice.

Example 20: Treatment of Myocardial Ischemia-Reperfusion Injury in Rats

Cysteinyl-succinyl crosslinked hemoglobin was used as a cardiac protective agent to reduce the myocardial infarct size in a rat model of acute myocardial ischemia-reperfusion. Twelve rats were randomly divided into 2 groups as follows:
Group 1: Lactated Ringer's Solution (Control Group); and
Group 2: Cysteinyl-succinyl Crosslinked Hemoglobin Solution (100 mg Hb/kg of body weight).

Myocardial ischemia and reperfusion were established in a standard rat model. Briefly, anaesthesia was induced in Wistar rats using isoflurane. Animals were then placed on a heated rodent operating table and internal temperature was continuously monitored with a rectal probe. Animals underwent bladder catheterization to monitor urine output, right jugular cannulation to allow fluid infusion, left carotid cannulation for both continuous arterial pressure monitoring and blood withdrawal, and tracheostomy. After insertion of a peritoneal catheter through a key-hole laparotomy, anaesthesia was maintained with repeated bolus of thiopental sodium 5 mg/kg and analgesia was assured with buprenorphine 0.1 mg/kg sc. A fluid bolus of 10 ml/kg was provided before induction of mechanical ventilation (tidal volume 12 ml/kg, PEEP 3 cmH$_2$O, RR 80 bpm) and a continuous infusion of a 50-50 mix of Lactated Ringer's solution+glucose 2.5% (10 ml/kg/h) was used as maintenance.

At the end of the surgical phase, after a recovery period of 60 min post-instrumentation, a left-sided thoracotomy was performed between the fourth and fifth ribs. A snare was placed around the region of myocardium containing the left anterior descending (LAD) coronary artery and ischaemia induced by tightening it. The ischaemic phase lasted 40 min of acute ligature followed by 120 min of reperfusion. 100 mg/kg of the cysteinyl-succinyl crosslinked hemoglobin solution or Lactated Ringer's solution was infused at 20 mins post-ischaemia and continued until 20 mins post-reperfusion at a rate of 1.5 ml/kg/h. Heart rate, mean arterial blood pressure, and temperature were measured continuously and degree of myocardial infarction/injury was assessed histologically as infarction size as a proportion of area at risk.

Figure 20:
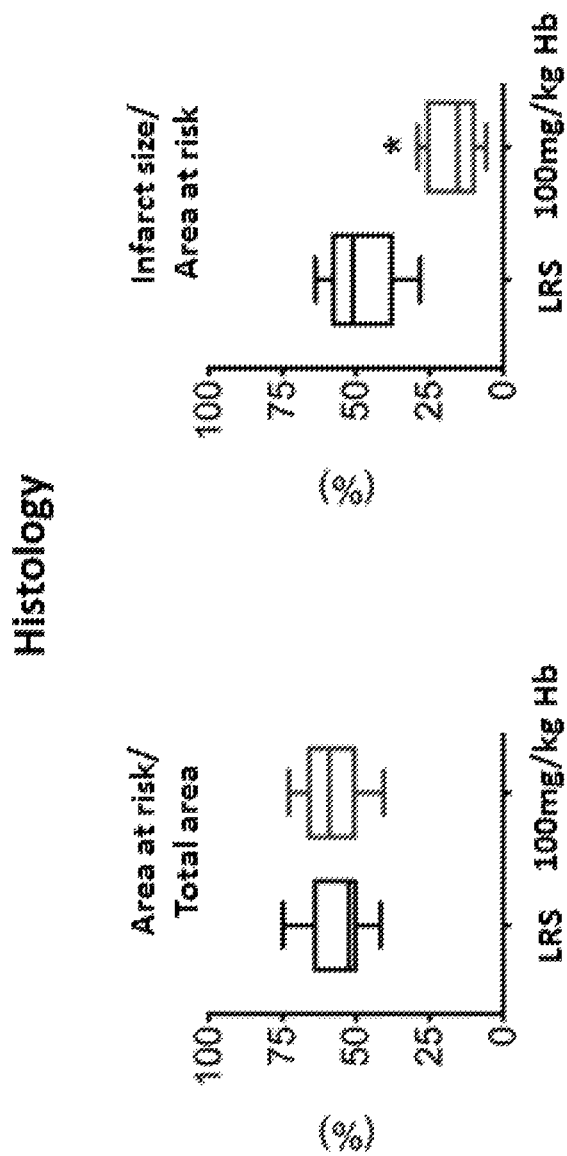
FIG. 20 shows a significant reduction of myocardial infraction area following treatment with cysteinyl-succinyl crosslinked hemoglobin solution. Histological analysis revealed a comparable area at risk is induced between the control and treatment groups following LAD ligation (Left graph). A significant reduction in the infarct area is observed in the groups receiving treatment with 100 mg/kg cysteinyl-succinyl crosslinked hemoglobin solution (Right graph).

As shown in FIG. 20, infusion of 100 mg/kg cysteinyl-succinyl crosslinked hemoglobin solution demonstrated a significant reduction in myocardial infarct size when compare to control group. Importantly, in this study when animals were administered intravenously with cysteinyl-succinyl crosslinked hemoglobin solution, there was no adverse effect on blood pressure and hemodynamic throughout the experiment, either during the ischemia and reperfusion period.

Example 21: Renal Protective Effect in Systemic Lupus Erythematosus Mouse Model Cysteinyl-succinyl crosslinked hemoglobin was used for the treatment of Systemic Lupus Erythematosus (SLE) in mice.

Figure 21:
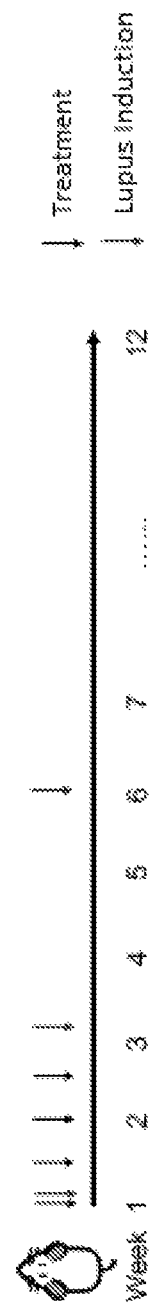
FIG. 21 is a schematic depiction of lupus induction and treatment in a C57 mouse model. Lupus nephritis is induced by bi-weekly injection of apoptotic cell nuclear extracts with Freud's adjuvant for a total of 3 times while treatment (800 mg/kg cysteinyl-succinyl crosslinked hemoglobin) is given twice per week for 2 weeks. Disease progression is continued for 12 weeks from the first induction for pathological analysis.

A chromatin-immunized lupus mouse model was used to examine the therapeutic effect of cysteinyl-succinyl crosslinked hemoglobin solution on lupus nephritis. Activated lymphocyte-derived DNA (ALD-DNA) was prepared from sorting-purified apoptotic immune cells. As shown in FIG. 21, murine lupus nephritis was induced in C57BL/6 mice immunized with ALD-DNA (100 g/mouse) dissolved in Freund's compete adjuvant on Day 1. Boost emulsion of ALD-DNA (50 g/mouse) with Freund's incomplete adjuvant was performed on Day 14 and 28. Cysteinyl-succinyl crosslinked hemoglobin was administrated intravenously at 800 mg/kg on Day 1, 4, 8, and 11 in a 2 week treatment period.

After 12-week disease progression, the mice were scarified and the kidneys were harvested, fixed and sectioned. Renal damage assessment was performed by staining the kidney tissue slides with hematoxylin and eosin (H&E) while glomerular immune complex deposition assessment was performed by immunofluorescence staining of immune complex deposition (IgM and IgG) using fluorochrome-labelled antibodies. The scoring system is shown as follows:
0=normal/no signal
1=mild cellular disruption/weak signal in less than 25% of glomeruli
2=moderate cellular disruption and appearance of balloon cells and vacuolation/moderate signal in greater than 50% of glomeruli
3=extensive cell disruption and vacuolation/extensive strong signal in greater than 50% of glomeruli. Glomerular activity index is assessed with the parameters below in a totality of score 0-15.
a) Cellular proliferation (0-3)
b) Leukocyte infiltration (0-3)
c) Fibrinoid necrosis or karyorrhexis (0-3)
d) Cellular crescents (0-3)
e) Hyaline thrombi, wire loops (0-3)

Figure 22:
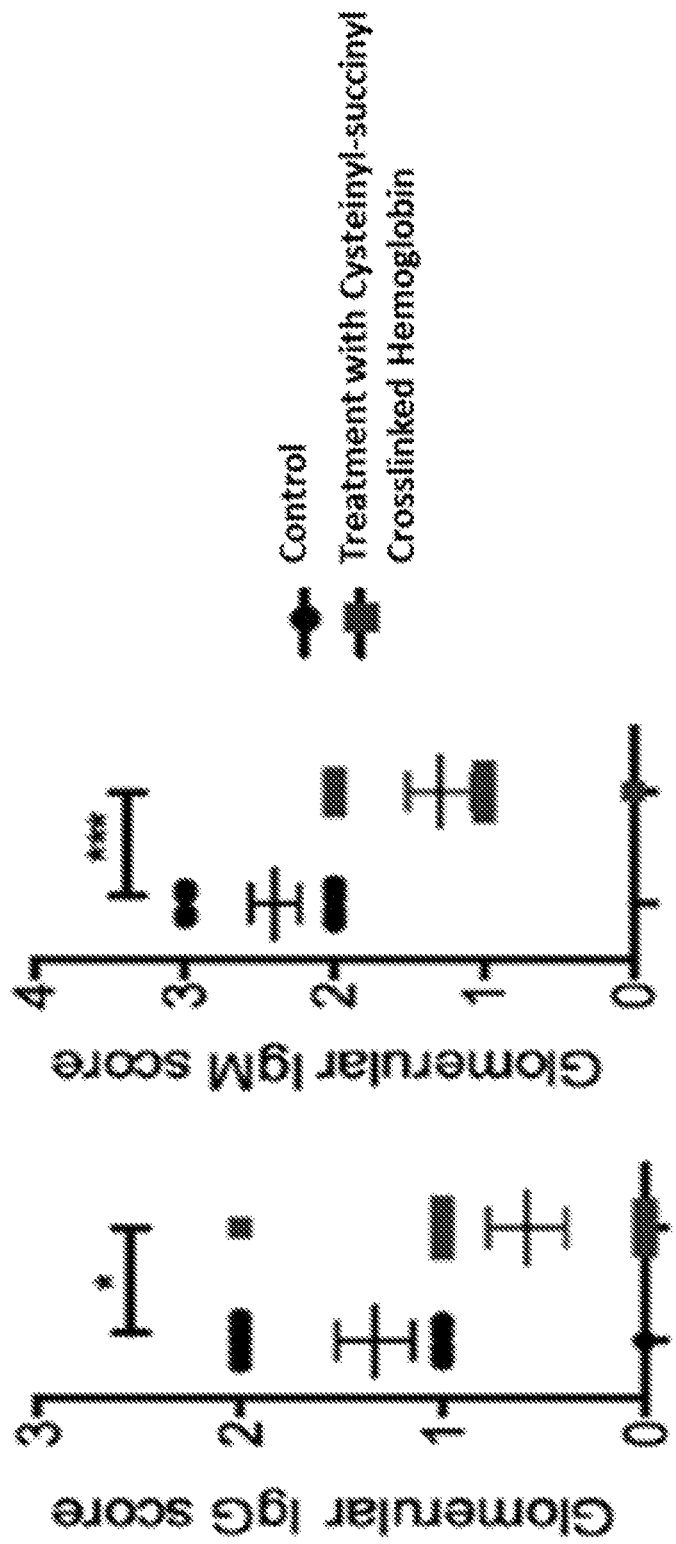
FIG. 22 shows a decreased immunoglobulin (Ig, score: 0-3) isotype M (IgM) and isotype G (IgG) deposition on glomerulus in kidneys. *$p<0.05$, ***$p<0.001$.
Figure 23:
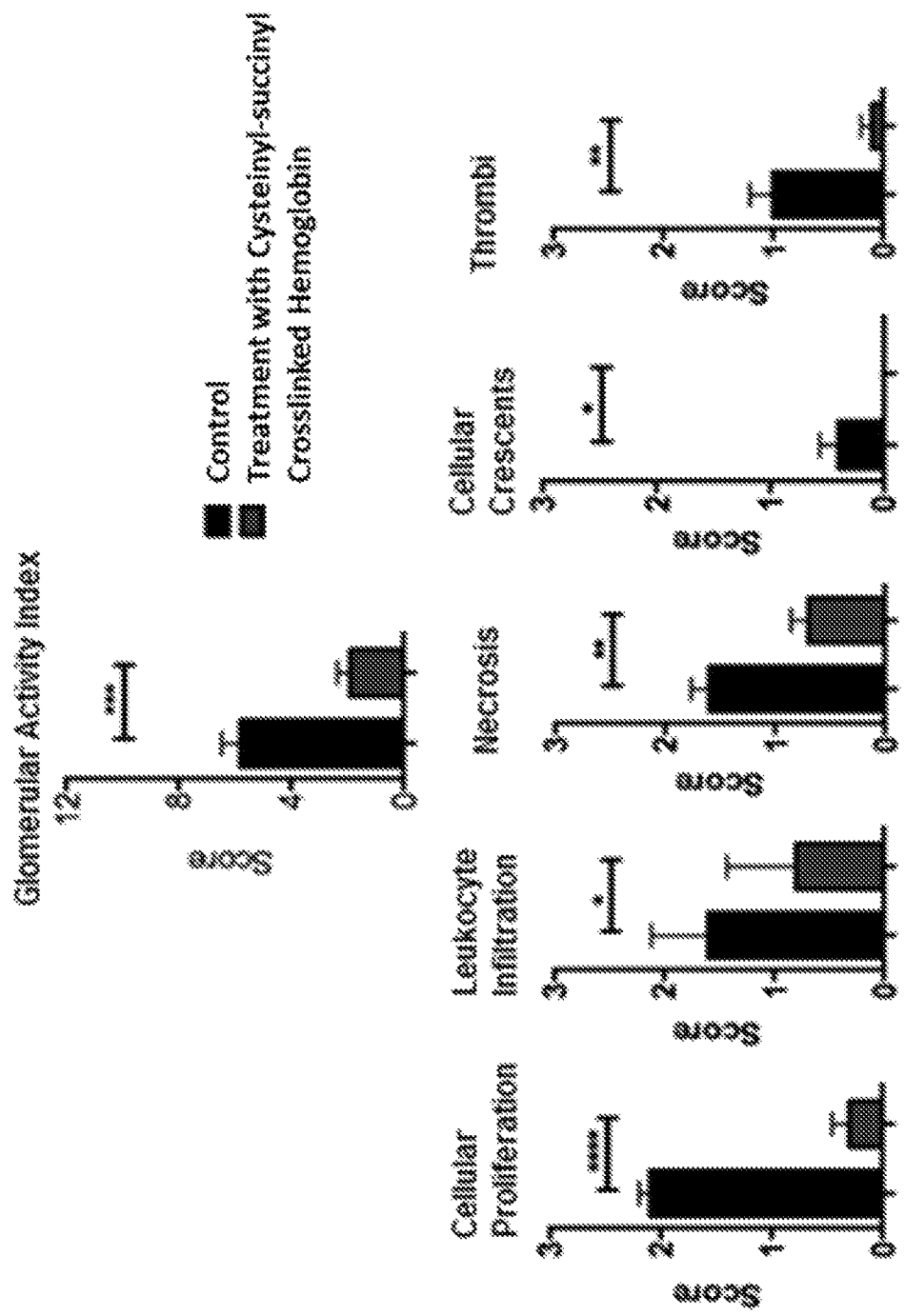
FIG. 23 shows lower glomerular activity index with significantly reduced cellular proliferation, leukocyte infiltration, fibrinoid necrosis/karyorrhexis, cellular crescents and hyaline thrombi, wire loops in the kidneys. *$p<0.05$, $p<0.01$, *$p<0.001$.

Significant reduction in glomerular IgG and IgM deposition was observed in the treatment with cysteinyl-succinyl crosslinked hemoglobin solution when compared to control (FIG. 22). Moreover, a significantly lower than control in total glomerular activity index was observed, showing less cellular proliferation, fibrinoid necrosis and cellular crescent in the kidneys treated with cysteinyl-succinyl crosslinked hemoglobin solution (FIG. 23).

In conclusion, cysteinyl-succinyl crosslinked hemoglobin significantly ameliorates the development of lupus nephritis in mice.

Example 22: Treatment of Severe Traumatic Brain Injury in Rat

Cysteinyl-succinyl crosslinked hemoglobin was used for the treatment of traumatic brain injury (TBI) produced by controlled cortical impact in rat model. The effect of treatment with cysteinyl-succinyl crosslinked hemoglobin solution administrated as a single dose on functional and histopathological outcomes following TBI was evaluated. In this study, 21 Sprague Dawley Rats were randomly assigned into 2 groups as follows:
Group 1: Saline Buffer (Negative Control); and
Group 2: Cysteinyl-succinyl Crosslinked Hemoglobin Solution (620 mg Hb/kg of body weight).

Each rat was implanted with a femoral vein catheter with BUTONVAB95BS (Instech) button about 14 days before the start of the experiment and housed in pairs in Opti-Rat cages at a 12:12 hour light/dark cycle with food and water offered ad libitum for at least 7 days. To induce severe traumatic brain injury by open-skull controlled cortical impact (CCI), rats received either 1.2 mg/kg sustained release buprenorphine (Buprenorphine SR™ Lab) plus 0.03 mg/kg regular buprenorphine (Vetergesic) or 1.2 mg/kg sustained release buprenorphine subcutaneously 30 min or 24 hours before, were anesthetized to perform surgical procedure. The skull was exposed by a single incision along the midline using a sterile scalpel-blade then, a 6 mm circular craniotomy was performed using a micro drill device (Harvard Apparatus, 72-6065) in the left parietal bone at the center of the coronal, sagittal and lambdoid sutures used as the outermost boundaries to expose the intact dura. Trephination site was then filled with sterile saline until ready for the impact. Exposed cortex with intact dura was subjected to controlled cortical impact injury. A controlled cortical impact was produced on the exposed cortex by the impactor actuator mounted on the Leica Impact One™ device with a 5.0 mm diameter impactor rod-tip, impacting the cortex at the velocity of 4.0 m/s, and the depth of the cortical deformation set at 3.00 mm with a dwell time of 200 ms to produce injury within the left parietal cortex.

At the end of CCI procedure, the wound was cleaned using sterile saline then, the skin wound was closed using single interrupted sutures and the rat was allowed to recover. No supplemental oxygen was given after TBI. One hour after CCI, the rats received a single infusion of either cysteinyl-succinyl crosslinked hemoglobin solution at 620 mg/kg (Group 2, n=10) or equivalent volume of saline (Group 1, n=11).

Neurological functions were assessed using a 21-point neuroscore at 4 hours and at Day 1, 3, and 7 following TBI and sensory-motor functions were also assessed by cylinder and horizontal ladder tests at Day 3 and 7, respectively. Brains were harvested on Day 7 post-TBI and processed for histochemical analysis.

Figure 24:
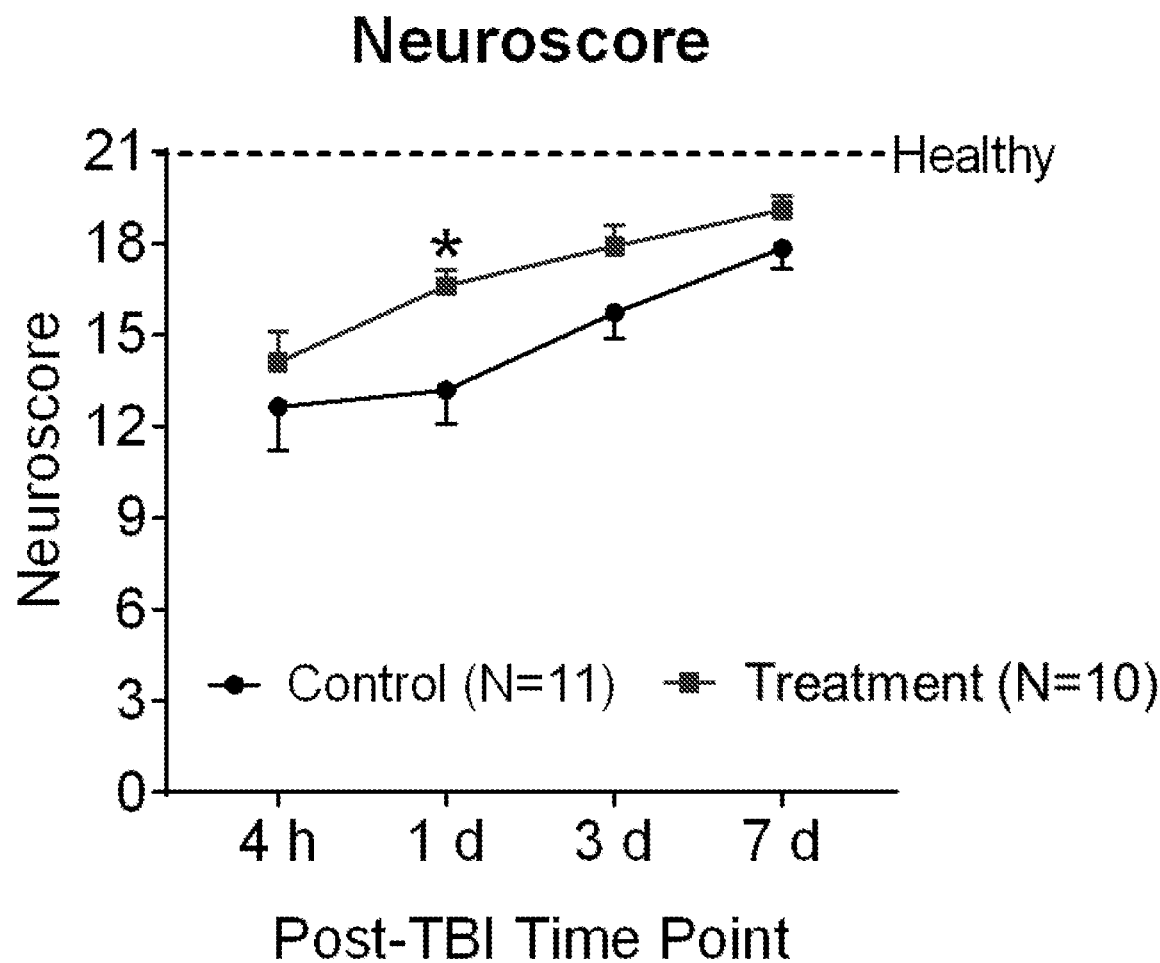
FIG. 24 shows an acute treatment with cysteinyl-succinyl crosslinked hemoglobin improved neurological score following TBI. The composite neuroscore is obtained using a battery of 8 neurological assessments at 4 hour, 1 day, 3 days and 7 days following TBI. Graph depicts effect of treatment with cysteinyl-succinyl crosslinked hemoglobin solution on neuroscore at different time points. Cysteinyl-succinyl crosslinked hemoglobin-treated TBI animals show significant increase in neuroscore 24 hours after the treatment (*$p<0.05$). Two-way repeated measures ANOVA followed by Sidak post hoc-test; data expressed as Mean±SEM.
Figure 25:
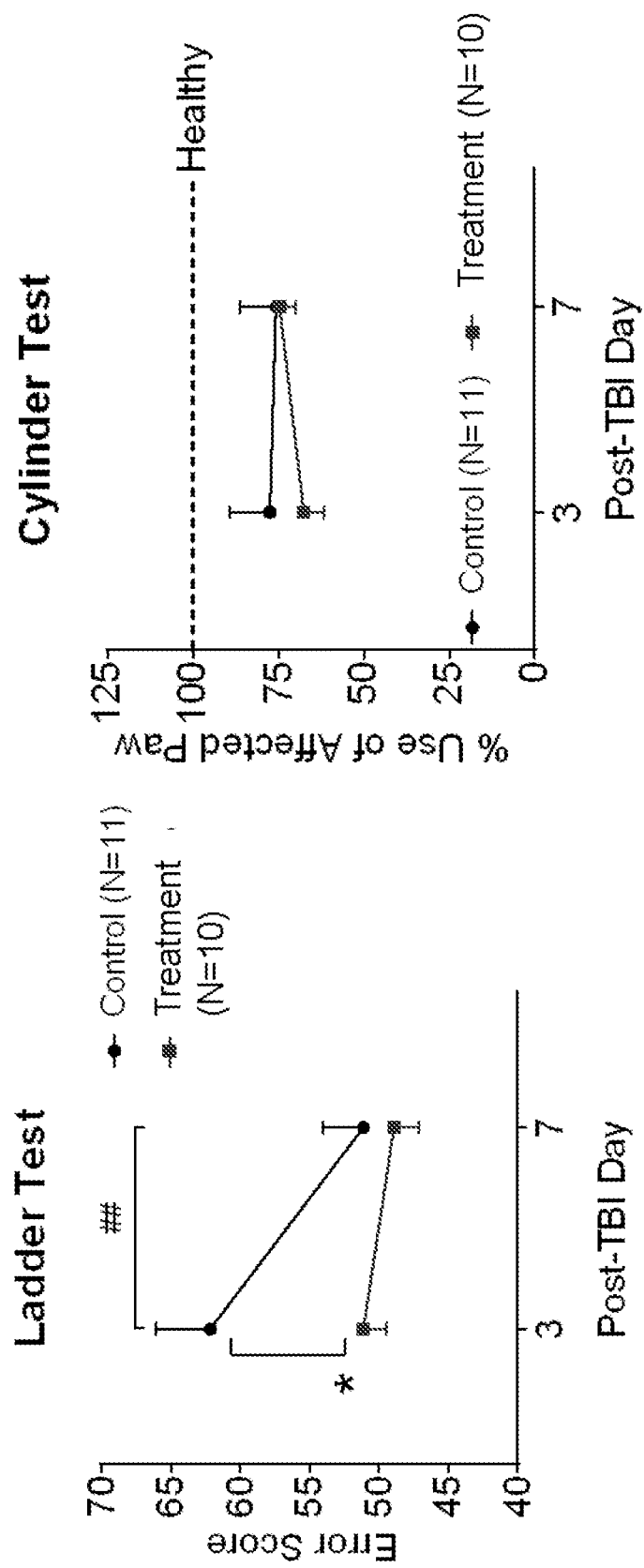
FIG. 25 shows an acute treatment with cysteinyl-succinyl crosslinked hemoglobin improved motor recovery following TBI. Efficacy of treatment with cysteinyl-succinyl crosslinked hemoglobin solution on motor functions at 1 h post-TBI is assessed using the horizontal ladder task and the cylinder test. The left graph represents the effect of treatment with cysteinyl-succinyl crosslinked hemoglobin on error score on the ladder test. Cysteinyl-succinyl crosslinked hemoglobin significantly improves the ladder test performance in TBI rats as compared to the control group on the Day 3 (*$p<0.05$) but not on Day 7. Only the error score of the control group on Day 7 is significantly lower than that on Day 3 (**$p<0.01$) while the treatment group reaches the same recovery level at Day 3. The right graph shows the degree of asymmetrical paw use during cylinder test conducted on Day 3 and Day 7 following TBI. No significant difference in the use of affected paw between control group and treatment group ($p>0.05$) has been found. Data expressed as Mean±SEM.

Single severe TBI induced neurological and motor deficits in 1-3 days followed by spontaneous recovery by Day 7 post-TBI in both treatment group (Group 2) and saline control group (Group 1). Interestingly, treatment with cysteinyl-succinyl crosslinked hemoglobin solution improved both neurological and motor functions to a significant degree, compared to the saline control group. The result shows that a single dose of 620 mg/kg cysteinyl-succinyl crosslinked hemoglobin solution, one hour after CCI resulted in a better neurological score at Day 1 (26% improvement in the neuroscore, *p<0.05), as depicted in FIG. 24. Concurrently, treatment with cysteinyl-succinyl crosslinked hemoglobin solution, one hour after CCI also significantly improved performance of TBI animals measured by the horizontal ladder test, as compared to the saline control group on Day 3 (18% reduction in ladder error score, *p<0.05). In contrast, the saline control group reached the same recovery level but only at Day 7 (*p<0.05, as compared to Day in the same group), indicating that the effect of the cysteinyl-succinyl crosslinked hemoglobin on accelerating functional recovery after TBI (FIG. 25A). However, such improvement was not seen the cylinder test (FIG. 25B), which accesses spontaneous forepaw use in explorative behavior with a clear ceiling.

Figure 26:
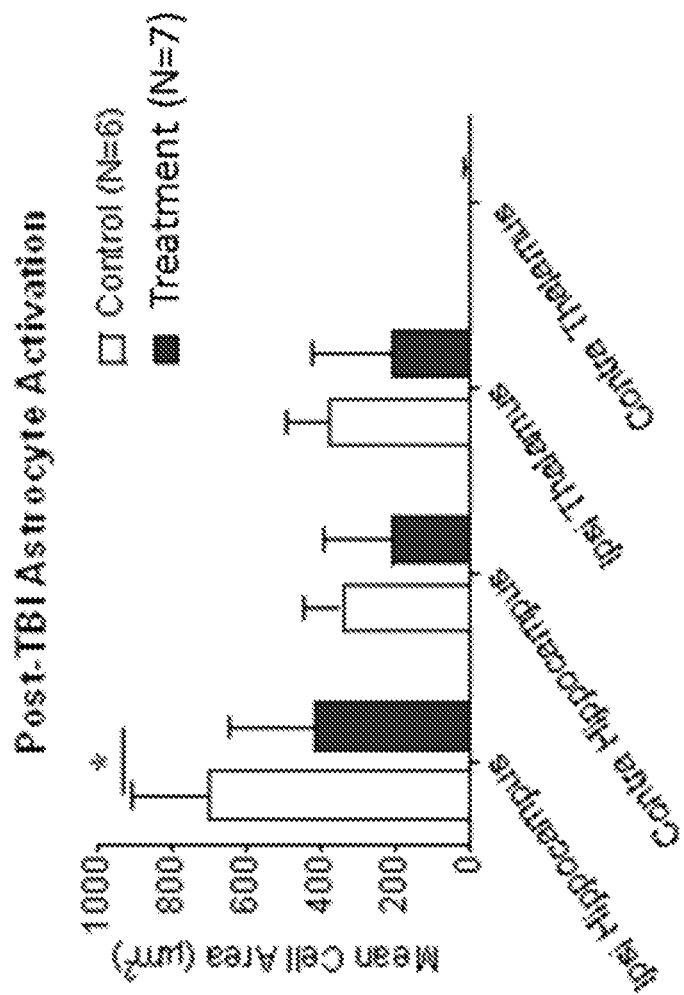
FIG. 26 shows the reduction of TBI-induced astrogliosis by treatment with cysteinyl-succinyl crosslinked hemoglobin solution. Effect of a single acute treatment with cysteinyl-succinyl crosslinked hemoglobin solution on astrocyte activation is assessed with GFAP immunofluorescence performed in brain tissue 7 days post-TBI. (A) Graph shows mean cell area of GFAP-positive astrocytes in both ipsilateral (Ipsi) and contralateral (Contra) hippocampus and thalamus. (*$p<0.05$), two-tailed t test; data expressed as Mean±SEM. (B) Representative 200× magnified images after background threshold using ImageJ of activated astrocytes from ipsilateral hippocampus (dental gyrus and CA region), ipsilateral thalamus and, contralateral hippocampus (CA region) for both control group (upper panel) and treatment group (lower panel). DG: Dentate gyrus, CA: Hippocampal CA region, Thal: Thalamus, i: Ipsilateral, c: Contralateral with respect to injury site.
Figure 26:
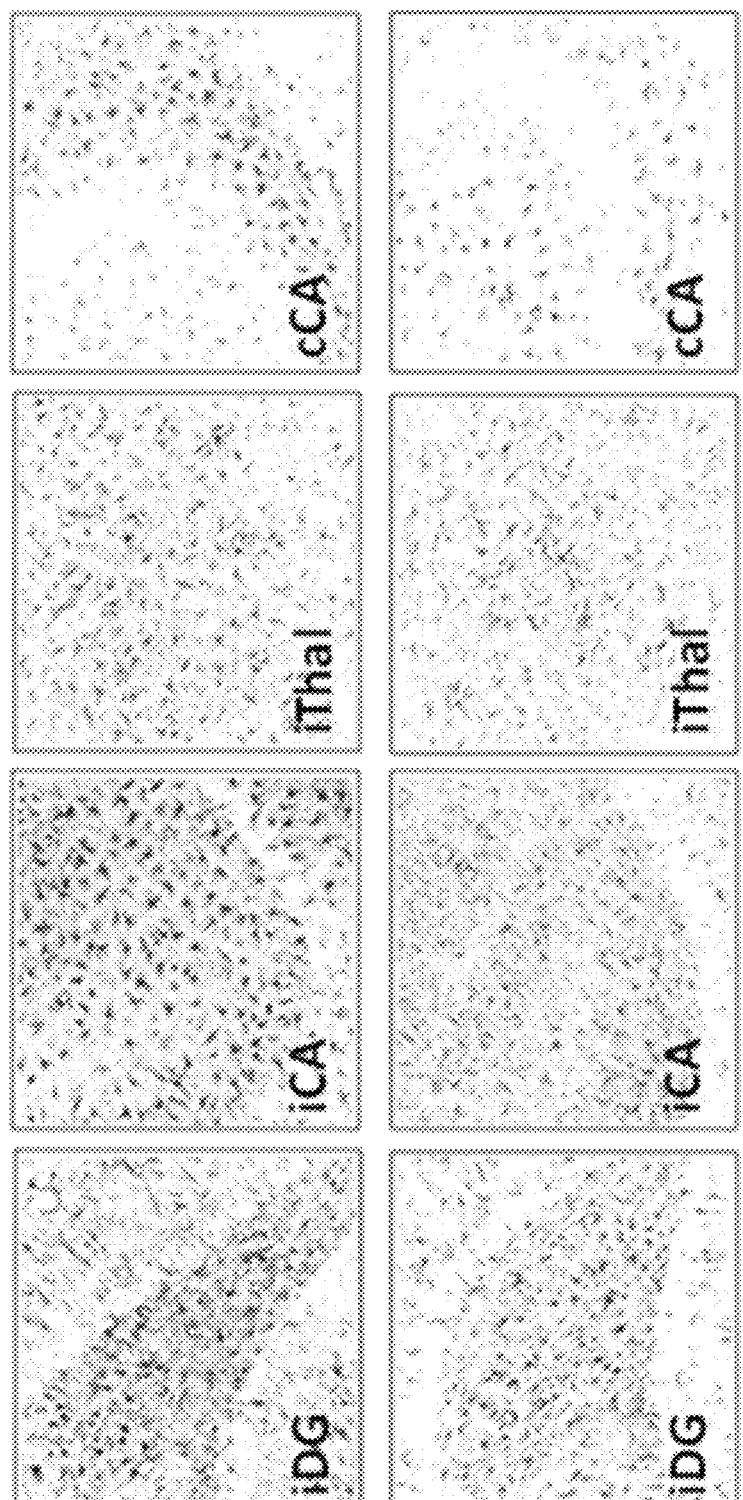

Besides a significant improvement in both neurological and motor functions observed in the TBI-induced rat model, rats treated with cysteinyl-succinyl crosslinked hemoglobin solution showed significant reduction in TBI-induced astrocyte activation under GFAP immunofluorescence analysis (*p<0.05; t-test), as depicted in FIG. 26.

Example 23: Cancer Treatment Studies: Tumor Inhibition in Triple-Negative Breast Cancer and Colorectal Cancer Both triple-negative breast cancer and colorectal cancer are associated with poor prognosis and a high mortality rate due to the formation of a solid tumor and an associated hypoxic environment. In searching for effective therapeutic options, some literature suggests the use of systemic oxygenation to inhibit the solid tumor growth and metastasis in various cancer models, by weakening the hypoxia-A2A adenosine receptors (A2aR)-driven immunosuppression in the tumor microenvironment. Therefore, the cysteinyl-succinyl crosslinked hemoglobin was tested for its role in inhibiting tumor growth in triple-negative breast cancer and colorectal cancer, respectively.

Example 23A: Inhibition of Tumor Growth in Triple-Negative Breast Cancer Xenograft Model A significant inhibition of tumor growth in TNBC 4T1 xenograft was observed after administration of cysteinyl-succinyl crosslinked hemoglobin solution. A murine triple-negative breast carcinoma xenograft (TNBC) model was employed. Murine TNBC 4T1 cells were cultured in DMEM supplemented with 10% FBS, 4 mM L-glutamine, 1 mM sodium pyruvate, 100 U/mL penicillin and 100 ug/mL streptomycin at 37° C. under 5% $CO_2$. Approximately $1 \times 10^5$ cancer cells (TNBC 4T1 cell line) were injected subcutaneously into four to six week-old female immune competent BALB/C mice. Once the tumor had grown for one week, tumor-bearing mice were randomized into two groups as follows:

Group 1: Saline Buffer (Control); and
Group 2: Cysteinyl-succinyl Crosslinked Hemoglobin Solution (400 mg Hb/kg of body weight).

For each group, 4-6 mice were given either saline or cysteinyl-succinyl crosslinked hemoglobin solution (400 mg/kg) once weekly for four weeks. Tumor volume was recorded every three days starting with the first day of treatment. The tumor volume was calculated using the modified ellipsoidal formula: Tumor Volume=$\frac{1}{2} \times LW^2$, where L and W represent the length and width of the tumor mass, measured by a digital caliper (Mitu-toyo Co, Tokyo, Japan) at each measurement. Results demonstrated that a suppression of tumor growth (22-51%) in TNBC 4T1 xenograft was observed in mice treated with cysteinyl-succinyl crosslinked hemoglobin solution at 6 days post $2^{nd}$ injection, compared to the control group, as depicted in Table 18.

TABLE 18

Percentage Change of the Normalized Tumor Volume Against the Control Group for the Syngeneic 4T1 Model.

| Measurement Time | % Change of the Normalized Tumor Volume against the Control Group | | | |
| --- | --- | --- | --- | --- |
| | Experiment 1 | Experiment 2 | Experiment 3 | Experiment 4 |
| 6 Day Post $1^{st}$ Injection | −39.6% | 4.2% | −17.0% | −25.9% |
| 6 Day Post $2^{nd}$ Injection | −51.2% | −23.4% | −49.1% | −22.4% |

Example 23B: Inhibition of Tumor Growth in Colorectal Cancer Xenograft Model

A significant inhibition of tumor growth in CT26 xenograft was observed after administration of cysteinyl-succinyl crosslinked hemoglobin solution, as shown in Table 13. A murine colorectal carcinoma xenograft (TNBC) model was employed. Murine CT26 cells were cultured in RPMI-1640 supplemented with 10% FBS, 100 U/mL penicillin and 100 ug/mL streptomycin at 37° C. under 5% $CO_2$. Approximately $1 \times 10^5$ cancer cells (CT26 cell line) were injected subcutaneously into four to six week-old female immune competent BALB/C mice. When the tumor grew for one week, tumor-bearing mice were randomized into two groups as follows:

Group 1: Saline Buffer (Control); and

Group 2: Cysteinyl-succinyl Crosslinked Hemoglobin Solution (400 mg Hb/kg of body weight)

For each group, 4-6 mice were given either saline or cysteinyl-succinyl crosslinked hemoglobin (400 mg/kg) once weekly for four weeks. Tumor volume was recorded every three days starting with the first day of treatment. The tumor volume was calculated using the modified ellipsoidal formula: Tumor Volume=½×LW², where L and W represent the length and width of the tumor mass, measured by a digital caliper (Mitu-toyo Co, Tokyo, Japan) at each measurement. Results demonstrated that a suppression of tumor growth (60%) in CT26 xenograft was observed in mice treated with cysteinyl-succinyl crosslinked hemoglobin solution at 6 days post $2^{nd}$ injection, compared to the control group, as depicted in Table 19.

TABLE 19

Percentage Change of the Normalized Tumor Volume Against the Control Group for the Syngeneic CT26 Model.

| Measurement Time | % Change of the Normalized Tumor Volume against the Control Group |
| --- | --- |
| 6 Day Post $1^{st}$ Injection | −60.77% |
| 6 Day Post $2^{nd}$ Injection | −65.77% |

What is claimed is:

1. A thiosuccinyl-crosslinked hemoglobin comprising a tetrameric hemoglobin and at least one thiosuccinyl crosslinking moiety of Formula 1:

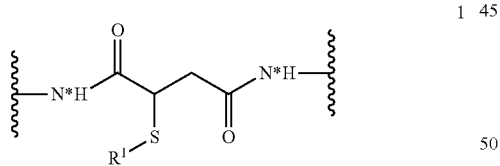

or a pharmaceutically acceptable salt or zwitterion thereof, wherein each N* independently represents a nitrogen selected from the group consisting of a nitrogen in a lysine residue side chain in the tetrameric hemoglobin and a nitrogen at a N-terminus in the tetrameric hemoglobin; and $R^1$ is alkyl, alkenyl, cycloalkyl, heterocycloalkyl, aryl, aralkyl, heteroaryl, or $-(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, $-(NR^4)S(O)_2OR^4$, and $-(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; $R^3$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S$ $(O)_2N(R^4)_2$, or —$(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

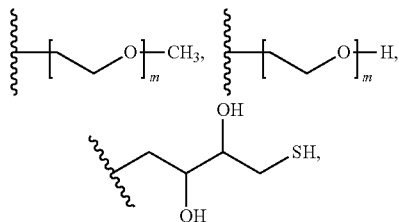

and $N^5$-(1-((carboxymethyl)amino)-1-oxo-3λ$^3$-propan-2-yl) glutamine or a pharmaceutically acceptable salt thereof, wherein m is a whole number selected from 1-1000, and wherein the thiosuccinyl-crosslinked hemoglobin is substantially pure.

2. The thiosuccinyl-crosslinked hemoglobin of claim 1, wherein $R^1$ is a moiety of Formula 2:

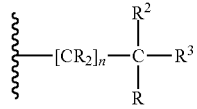

wherein n is a whole number selected from the group consisting of 0, 1, 2, 3, and 4;
R for each instance is independently selected from the group consisting of hydrogen, alkyl, aralkyl, cycloalkyl, heterocycloalkyl, aryl, and heteroaryl;
$R^2$ is hydrogen, alkyl, aralkyl, cycloalkyl, heterocycloalkyl, aryl, heteroaryl, —$N(R^4)_2$, —$NH(C=O)R^4$, or —$NH(C=O)N(R^4)_2$;
$R^3$ is hydrogen, alkyl, aralkyl, cycloalkyl, heterocycloalkyl, aryl, heteroaryl, —$CO_2R^4$, —$(C=O)NHR^4$, —$OR^4$, or —$N(R^4)_2$; and
$R^4$ for each instance is independently selected from the group consisting of hydrogen, alkyl, aralkyl, cycloalkyl, heterocycloalkyl, aryl, and heteroaryl;
or $R^1$ is a moiety selected from the group consisting of:

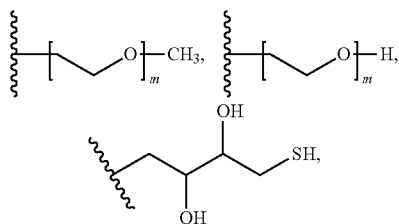

and $N^5$-(1-((carboxymethyl)amino)-1-oxo-3λ$^3$-propan-2-yl) glutamine or a pharmaceutically acceptable salt thereof, wherein m is a whole number selected from 1-1000.

3. The thiosuccinyl-crosslinked hemoglobin of claim 2, wherein n is 1 or 2; R is hydrogen; $R^2$ is —$NHR^4$, —NH$(C=O)R^4$, or —$NH(C=O)R^4N(R^4)_2$; and $R^3$ is hydrogen, —$OR^4$, —$CO_2R^4$, or —$(C=O)NHR^4$, wherein $R^4$ for each instance is independently selected from the group consisting of hydrogen and alkyl.

4. The thiosuccinyl-crosslinked hemoglobin of claim 1, wherein $R^1$ is selected from the group consisting of:

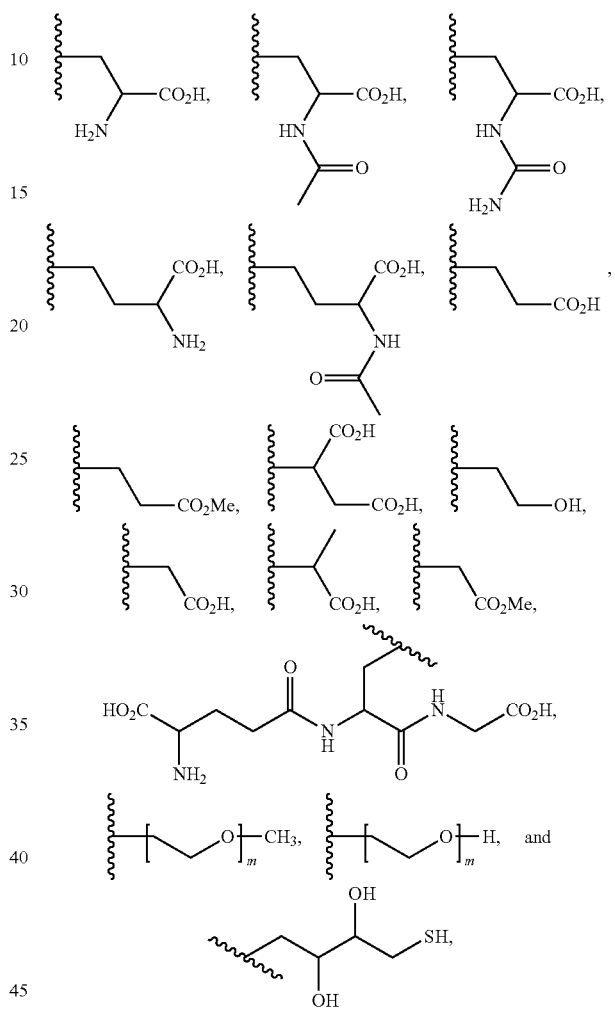

or a pharmaceutically acceptable salt or zwitterion thereof, wherein m is a whole number selected from 1-1000.

5. The thiosuccinyl-crosslinked hemoglobin of claim 1, wherein each N* independently represents a nitrogen selected from the group consisting of a nitrogen in a lysine residue side chain in a beta globin chain of the tetrameric hemoglobin and a nitrogen at a N-terminus in a beta globin chain of the tetrameric hemoglobin.

6. The thiosuccinyl-crosslinked hemoglobin of claim 1, wherein the thiosuccinyl-crosslinked hemoglobin comprises 1, 2, or 3 thiosuccinyl crosslinking moiety of Formula 1.

7. The thiosuccinyl-crosslinked hemoglobin of claim 1, wherein the at least one thiosuccinyl crosslinking moiety crosslinks two beta globin chains of the tetrameric hemoglobin.

8. The thiosuccinyl-crosslinked hemoglobin of claim 1, wherein the tetrameric hemoglobin is human hemoglobin, bovine hemoglobin, or porcine hemoglobin.

9. The thiosuccinyl-crosslinked hemoglobin of claim 1, wherein the thiosuccinyl-crosslinked hemoglobin is substantially stroma-free.

10. A pharmaceutical composition comprising at least one of the thiosuccinyl-crosslinked hemoglobin of claim 1 and at least one pharmaceutically acceptable excipient.

11. The pharmaceutical composition of claim 10, wherein the thiosuccinyl-crosslinked hemoglobin is present in the pharmaceutical composition at a weight percentage between 10-90%.

12. The pharmaceutical composition of claim 10, wherein the pharmaceutical composition comprises thiosuccinyl-crosslinked hemoglobin comprising 1, 2, or 3 thiosuccinyl crosslinking moieties of Formula 1; or a combination thereof.

13. A method for preparing the thiosuccinyl-crosslinked hemoglobin of claim 1 comprising the steps of:
contacting a tetrameric hemoglobin with a fumaryl crosslinking agent thereby forming a fumaryl-crosslinked hemoglobin; contacting the fumaryl-crosslinked hemoglobin with a thiol or a pharmaceutically acceptable salt or zwitterion thereof thereby forming the thiosuccinyl-crosslinked hemoglobin of claim 1.

14. The method of claim 13, wherein the fumaryl crosslinking agent is selected from the group consisting of bis-3,5-dibromosalicyl fumarate (DBSF), fumaryl chloride and bis(salicyl) fumarate.

15. The method of claim 13, wherein the thiol has the formula: R'SH or a pharmaceutically acceptable salt or zwitterion thereof, wherein $R^1$ is alkyl, alkenyl, cycloalkyl, heterocycloalkyl, aryl, aralkyl, heteroaryl, or —$(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $R^1$ is alkyl, alkenyl, cycloalkyl, heterocycloalkyl, aryl, aralkyl, heteroaryl, or —$(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —$(NR^4)(C=O)R^4$, —$(NR^4)(C=O)OR^4$, —$O(C=O)N(R^4)_2$, —$O(C=NR^4)N(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)_2N(R^4)_2$, —$(NR^4)S(O)_2N(R^4)_2$, —$(NR^4)S(O)_2OR^4$, and —$(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —$(NR^4)(C=O)R^4$, —$(NR^4)(C=O)OR^4$, —$O(C=O)N(R^4)_2$, —$O(C=NR^4)N(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)_2N(R^4)_2$, —$(NR^4)S(O)_2N(R^4)_2$, or —$(NR^4)S(O)_2OR^4$; $R^3$ is hydrogen, alkyl, aralkyl, cycloalkyl, heterocycloalkyl, aryl, heteroaryl, $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —$(NR^4)(C=O)R^4$, —$(NR^4)(C=O)OR^4$, —$O(C=O)N(R^4)_2$, —$O(C=NR^4)N(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)_2N(R^4)_2$, —$(NR^4)S(O)_2N(R^4)_2$, or —$(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

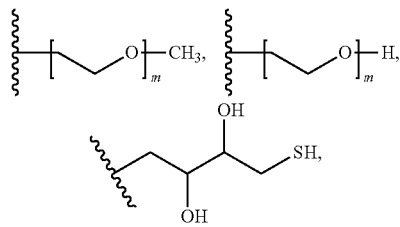

and $N^5$-(1-((carboxymethyl)amino)-1-oxo-3$\lambda^3$-propan-2-yl) glutamine or a pharmaceutically acceptable salt thereof, wherein m is a whole number selected from 1-1000.

16. The method of claim 15, wherein the thiol has the Formula 3:

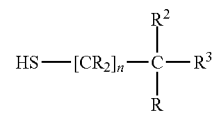

or a pharmaceutically acceptable salt or zwitterion thereof, wherein
n is an integer selected from the group consisting of 0, 1, 2, 3, and 4;
R for each instance is independently selected from the group consisting of hydrogen, alkyl, aralkyl, cycloalkyl, heterocycloalkyl, aryl, and heteroaryl;
$R^2$ is hydrogen, alkyl, aralkyl, cycloalkyl, heterocycloalkyl, aryl, heteroaryl, —$N(R^4)_2$, or —$NH(C=O)R^4$;
$R^3$ is hydrogen, alkyl, aralkyl, cycloalkyl, heterocycloalkyl, aryl, heteroaryl, —$CO_2R^4$, —$(C=O)NHR^4$, —$OR^4$, or —$N(R^4)_2$; and
$R^4$ for each instance is independently selected from the group consisting of hydrogen, alkyl, aralkyl, cycloalkyl, heterocycloalkyl, aryl, and heteroaryl; or the thiol is selected from the group consisting of dithiothreitol, $HS(CH_2CH_2O)_mCH_3$, $HS(CH_2CH_2O)_mH$, glutathione or a pharmaceutically acceptable salt thereof, wherein m is a whole number selected between 1-1000.

17. The method of claim 16, wherein n is 1 or 2; R is hydrogen; $R^2$ is —$NHR^4$, —$NH(C=O)R^4$, or —$NH(C=O)(NR^4)_2$; and $R^3$ is hydrogen, —$OR^4$, —$CO_2R^4$, or —$(C=O)NHR^4$, wherein $R^4$ for each instance is independently selected from the group consisting of hydrogen and alkyl.

18. The method of claim 13, wherein the thiol is selected from the group consisting of:

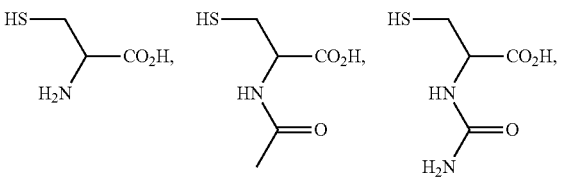

-continued

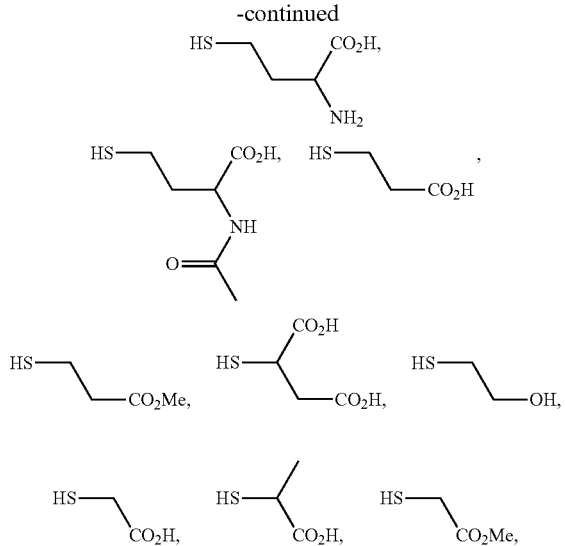

-continued

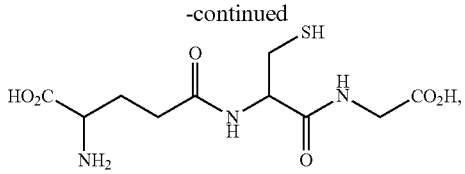

dithiothreitol, $HS(CH_2CH_2O)_mCH_3$, and $HS(CH_2CH_2O)_mH$ or a pharmaceutically acceptable salt or zwitterion thereof, wherein m is a whole number selected between 1-1000.

19. The method of claim 13, wherein the step of contacting the fumaryl-crosslinked hemoglobin with a thiol or a pharmaceutically acceptable salt or zwitterion thereof, the fumaryl-crosslinked hemoglobin and the thiol are present in a molar ratio of at least 1:1; 1:2; or 1:3.

20. The method of claim 19, wherein the fumaryl-crosslinked hemoglobin and the thiol are present in a molar ratio of greater than 1:3.

21. The method of claim 13, wherein the thiosuccinyl-crosslinked hemoglobin is in isolated form.

* * * * *